(12) United States Patent
Frazer et al.

(10) Patent No.: US 6,846,671 B2
(45) Date of Patent: Jan. 25, 2005

(54) METHOD AND POLYNUCLEOTIDES FOR DETERMINING TRANSLATIONAL EFFICIENCY OF A CODON

(75) Inventors: Ian Hector Frazer, St. Lucia (AU); Jian Zhou, deceased, late of Jindalee (AU); by Xiao Yi Sun, legal representative, Jindalee (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 09/900,345

(22) Filed: Jul. 6, 2001

(65) Prior Publication Data

US 2003/0031999 A1 Feb. 13, 2003

Related U.S. Application Data

(63) Continuation of application No. PCT/AU00/00008, filed on Jan. 7, 2000.

(30) Foreign Application Priority Data

Jan. 8, 1999 (AU) ................................................ PP8078

(51) Int. Cl.$^7$ ............................ C12N 5/10; C12N 1/00; C12N 15/52; C12N 15/62; C12N 15/63
(52) U.S. Cl. ..................... 435/325; 435/243; 435/320.1; 435/419; 536/23.2; 536/23.4
(58) Field of Search ............................ 435/320.1, 325, 435/419, 243; 536/23.4, 23.2

(56) References Cited

FOREIGN PATENT DOCUMENTS

WO        WO 86/05810 A1        10/1986

OTHER PUBLICATIONS

Bertling, "Use of Liposomes, Viral Capsids, and Nanoparticles as DNA Carriers," *Biotechnology and Applied Biochemistry*, 13:390–405 (1991).
Salmons, "Targeting of Retroviral Vectors for Gene Therapy," *Human Gene Therapy*, 4:129–141 (1993).
Shigekawa, "Electroporation of Eukaryotes and Prokaryotes: A General Approach to the Introduction of Macromolecules into Cells," *BioTechniques*, 6(8):742–751 (1988).
Calabretta, "The Laboratory–Clinic Interface—Prospects for gene–directed therapy with antisense oligodeoxynucleotides," *Cancer Treatment Reviews*, 19:169–179 (1993).
Mulligan, "The Basic Science of Gene Therapy," *Science*, 926:926–932 (May 14, 1993).
Sharp, "Codon usage patterns in *Escherichia coli, Bacillus subtilis, Saccharomyces cerevisiae, Schizosaccharomyces pombe, Drosophila melanogaster* and *Homo sapiens*; a review of the considerable within–species diversity," *Nucleic Acids Research*, Abstract, 16(17):8207–8211 (1988).
Rose, "A New Cationic Liposome Reagent Mediating Nearly Quantitative Transfection of Animal Cells," *BioTechniques*, 10(4):520–525 (1991).
Chen, "High–Efficiency Transformation of Mammalian Cells by Plasmid DNA," *Molecular and Cellular Biology*, 7:2745–2752 (Aug. 1987).
Barr, "Systemic Delivery of Recombinant Proteins by Genetically Modified Myoblasts," *Science*, 254:1507–1509 (Dec. 6, 1991).
Dhawan, "Systemic Delivery of Human Growth Hormone by Injection of Gentically Engineered Myoblasts," *Science*, 254:1509–1512 (Dec. 6, 1991).
Wolff, "Direct Gene Transfer into Mouse Muscle in Vivo," *Science*, 247:14651468 (Mar. 23, 1990).
Zhu, "Systemic Gene Expression After Intravenous DNA Delivery into Adult Mice," *Science*, 261:209–211 (Jul. 9, 1993).
Riordan, "Identification of the Cyctic Fibrosis Gene: Cloning and Characterization of Complementary DNA," *Science*, 245:1066–1073 (Sep. 8, 1989).
Miller, "Human gene therapy comes of age," *Nature*, 357:455–460 (Jun. 11, 1992).
Kurland, "Codon bias and gene expression," *FEBS Letters*, 285(2):165–169 (Jul. 1991); and.
Sharp, "Codon usage: mutational bias, translational selection, or both?", *Biochem. Soc. Trans.*, 21(4):835–841 (1993).

*Primary Examiner*—Terry McKelvey
(74) *Attorney, Agent, or Firm*—Akin Gump Strauss Hauer & Feld, LLP

(57) ABSTRACT

A method is disclosed for determining the translational efficiency of an individual codon in a cell. The method comprises introducing into the cell a synthetic construct comprising a reporter polynucleotide fused in frame with a tandem repeat of said individual codon, wherein said reporter polynucleotide encodes a reporter protein, and wherein said synthetic construct is operably linked to a regulatory polynucleotide and measuring expression of said reporter protein in said cell to determine the translational efficiency of said codon.

40 Claims, No Drawings

METHOD AND POLYNUCLEOTIDES FOR DETERMINING TRANSLATIONAL EFFICIENCY OF A CODON

CROSS-REFERENCE TO RELATED APPLICATIONS

This application is a continuation application of co-pending International Patent Application No. PCT/AU00/00008 filed Jan. 7, 2000, which designates the United States, and which claims priority of Australian Provisional Patent Application No. PP8078/99 filed Jan. 8, 1999.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

This invention relates generally to gene expression and in particular, to a method and polynucleotides for determining codon utilization in particular cells or tissues of an organism. More particularly, the method and polynucleotides of the invention are concerned with ascertaining codon preferences in cells or tissues for the purpose of modifying the translational efficiency of protein-encoding polynucleotides in those cells or tissues.

It is well known that a "triplet" codon of four possible nucleotide bases can exist in 64 variant forms. These forms provide the message for only 20 different amino acids (as well as translation initiation and termination) and this means that some amino acids can be encoded by more than one codon. Some amino acids have as many as six "redundant", alternative codons while some others have a single, required codon.

For reasons not completely understood, codon utilization is highly biased in that alternative codons are not at all uniformly present in the endogenous DNA of differing cell types. In this regard, there appears to exist a variable natural hierarchy of "preference" for certain codons between different cell types or between different organisms.

Codon usage patterns have been shown to correlate with relative abundance of isoaccepting transfer RNA (iso-tRNA) species, and with genes encoding proteins of high versus low abundance. Moreover, the present inventors recently discovered that the intracellular abundance of different iso-tRNAs varies in different cells or tissues of a single multi-cellular organism (see copending International Application No. PCT/AU98/00530).

The implications of codon preference phenomena on gene expression are manifest in that these phenomena can affect the translational efficiency of messenger RNA (mRNA) It is widely known in this regard that translation of "rare codons", for which the corresponding iso-tRNA is in relatively low abundance, may cause a ribosome to pause during translation which can lead to a failure to complete a nascent polypeptide chain and an uncoupling of transcription and translation.

A primary goal in recombinant research is to provide transgenic organisms with expression of a foreign gene in an amount sufficient to confer the desired phenotype to the organism. However, expression of the foreign gene may be severely impeded if a particular host cell of the organism or the organism itself has a low abundance of iso-tRNAs corresponding to one or more codons of the foreign gene. Accordingly, a major aim of investigators in this field is to first ascertain the codon preference for particular cells or tissues in which a foreign gene is to be expressed, and to subsequently alter the codon composition of the foreign gene for optimized expression in those cells or tissues.

Codon preference may be determined simply by analyzing the frequency at which codons are used by genes expressed in a particular cell or tissue or in a plurality of cells or tissues of a given organism. Codon frequency tables as well as suitable methods for determining frequency of codon usage in an organism are described, for example, in an article by Sharp et al (1988, *Nucleic Acids Res.* 16 8207–8211). The relative level of gene expression (e.g., detectable protein expression Vs no detectable protein expression) can provide an indirect measure of the relative abundance of specific iso-tRNAs expressed in different cells or tissues.

Alternatively, codon preference may be determined by measuring the relative intracellular abundance of different iso-tRNA species. For example, reference may be made to copending International Application No. PCT/AU98/00530 that describes a method that utilizes labeled oligonucleotides specific for different iso-tRNAs to probe an RNA extract prepared from a particular cell or tissue source.

The above methods provide useful indirect evidence for determining codon preference. However, such indirect evidence may not provide an accurate indication of the translational efficiency of a given codon. Accordingly, there is a need to provide a method that more directly ascertains the translational efficiency of a codon in a cell or tissue.

SUMMARY OF THE INVENTION

In one aspect of the invention, there is provided a method for determining the translational efficiency of an individual codon in a cell of a predetermined type, said method comprising:

introducing into a first cell of said predetermined type a synthetic construct comprising a reporter polynucleotide fused in frame with a tandem repeat of said individual codon, wherein said reporter polynucleotide encodes a reporter protein, and wherein said synthetic construct is operably linked to a regulatory polynucleotide; and measuring expression of said reporter protein in said cell of said predetermined type to determine the translational efficiency of said codon.

Preferably, the method further comprises comparing:

expression of said reporter protein in said first cell to which a synthetic construct comprising a tandem repeat of said individual codon was provided; and expression of said reporter protein in second cell of the same type as said first cell to which a synthetic construct comprising a tandem repeat of another individual codon was provided;

to thereby determine the relative translational efficiency of said individual codons in said cell of said predetermined type.

Suitably, the method further comprises comparing:

expression of said reporter protein in said first cell to which a synthetic construct comprising a tandem repeat of said individual codon was provided; and expression of said reporter protein in another cell of a different predetermined type than said first cell to which a synthetic construct comprising a tandem repeat of said individual codon was provided;

to thereby determine the translational efficiency of said individual codon in said first cell relative to said other cell.

Preferably, the method further comprises:

introducing the synthetic construct into a progenitor cell of said cell of said predetermined type; and producing said cell of said predetermined type from said progenitor cell;

wherein said cell of said predetermined type contains said synthetic construct.

Suitably, the method further comprises:

introducing the synthetic construct into a progenitor of said cell; and growing an organism or part thereof from said progenitor cell;

wherein said organism or part thereof comprises said cell containing said synthetic construct.

Suitably, the method further comprises:

introducing the synthetic construct into an organism or part thereof such that said synthetic construct is introduced into said cell of said predetermined type.

In another aspect, the invention resides in a synthetic construct comprising a reporter polynucleotide fused in frame with a tandem repeat of individual codons, wherein said reporter polynucleotide encodes a reporter protein, and wherein said synthetic construct is operably linked to a regulatory polynucleotide.

In yet another aspect of the invention, there is provided a method of constructing a synthetic polynucleotide from which a protein is selectively expressed in a target cell of an organism, relative to another cell of the organism, said method comprising:

selecting a first codon of a parent polynucleotide for replacement with a synonymous codon which has a higher translational efficiency in said target cell than in said other cell; and replacing said first codon with said synonymous codon to form said synthetic polynucleotide, wherein said first codon and said synonymous codon are selected by:

comparing translational efficiencies of individual codons in said target cell relative to said other cell using the method broadly described above; and selecting said first codon and said synonymous codon based on said comparison.

Preferably, said synonymous codon corresponds to a reporter construct from which the reporter protein is expressed in said target cell at a level that is at least 110%, preferably at least 200%, more preferably at least 500%, and most preferably at least 1000%, of that expressed from said reporter construct in said other cell In a further aspect, the invention provides a method of constructing a synthetic polynucleotide from which a protein is expressible in a target cell of an organism at a higher level than from a parent polynucleotide encoding said protein, said method comprising:

selecting a first codon of the parent polynucleotide for replacement with a synonymous codon which has a higher translational efficiency in said target cell than said first codon;

replacing said first codon with said synonymous codon to form said synthetic polynucleotide, wherein said first codon and said synonymous codon are selected by:

comparing translational efficiencies of different individual codons in said target cell using the method broadly described above; and selecting said first codon and said synonymous codon based on said comparison.

Suitably, said synonymous codon corresponds to a reporter construct from which the reporter protein is expressed in said target cell at a level that is at least 110%, preferably at least 200%, more preferably at least 500%, and most preferably at least 1000%, of that expressed from the different reporter construct corresponding to said first codon.

DETAILED DESCRIPTION OF THE INVENTION

1. Definitions

The articles "a" and "an" are used herein to refer to one or to more than one (i.e., to at least one) of the grammatical object of the article. By way of example, "an element" means one element or more than one element.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "expressible" is meant expression of a protein to a level sufficient to effect a particular function associated with the protein. By contrast, the terms "not expressible" and "not substantially expressible" as used interchangeably herein refers to (a) no expression of a protein, (b) expression of a protein to a level that is not sufficient to effect a particular function associated with the protein, (c) expression of a protein, which cannot be detected by a monoclonal antibody specific for the protein, or (d) expression of a protein, which is less that 1% of the level expressed in a wild-type cell that normally expresses the protein.

By "expressing said synthetic construct" is meant transcribing the synthetic construct such that mRNA is produced.

By "expression vector" is meant any autonomous genetic element capable of directing the synthesis of a protein encoded by the vector. Such expression vectors are known by practitioners in the art.

As used herein, the term "function" refers to a biological, enzymatic, or therapeutic function.

By "highly expressed genes" is meant genes that express high levels of mRNA, and preferably high level of protein, relative to other genes.

By "isoaccepting transfer RNA" or "iso-tRNA" is meant one or more transfer RNA molecules that differ in their anticodon nucleotide sequence but are specific for the same amino acid.

By "natural gene" is meant a gene that naturally encodes the protein. However, it is possible that the parent polynucleotide encodes a protein that is not naturally-occurring but has been engineered using recombinant techniques.

The term "non-cycling cell" as used herein refers to a cell that has withdrawn from the cell cycle and has entered the G0 state. In this state, it is known that transcription of endogenous genes and protein translation are at substantially reduced levels compared to phases of the cell cycle, namely G1, S, G2 and M. By contrast, the term "cycling cell" as used herein refers to a cell, which is in one of the above phases of the cell cycle.

By "obtained from" is meant that a sample such as, for example, a polynucleotide extract or polypeptide extract is isolated from, or derived from, a particular source of the host. For example, the extract can be obtained from a tissue or a biological fluid isolated directly from the host.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

By "operably linked" is meant that transcriptional and translational regulatory polynucleotides are positioned relative to a polypeptide-encoding polynucleotide in such a manner that the polynucleotide is transcribed and the polypeptide is translated.

By "pharmaceutically-acceptable carrier" is meant a solid or liquid filler, diluent or encapsulating substance that can be safely used in topical or systemic administration to a mammal.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

The term "polynucleotide" or "nucleic acid" as used herein designates mRNA, RNA, cRNA, cDNA or DNA. The term typically refers to oligonucleotides greater than 30 nucleotide residues in length.

By "primer" is meant an oligonucleotide which, when paired with a strand of DNA, is capable of initiating the synthesis of a primer extension product in the presence of a suitable polymerizing agent. The primer is preferably single-stranded for maximum efficiency in amplification but can alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotide residues, although it can contain fewer nucleotide residues. Primers can be large polynucleotides, such as from about 200 nucleotide residues to several kilobases or more. Primers can be selected to be "substantially complementary" to the sequence on the template to which it is designed to hybridize and serve as a site for the initiation of synthesis. By "substantially complementary", it is meant that the primer is sufficiently complementary to hybridize with a target polynucleotide. Preferably, the primer contains no mismatches with the template to which it is designed to hybridize but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridize therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another polynucleotide, often called the "target polynucleotide", through complementary base pairing. Probes can bind target polynucleotides lacking complete sequence complementarity with the probe, depending on the stringency of the hybridization conditions. Probes can be labeled directly or indirectly.

The terms "precursor cell or tissue" and "progenitor cell or tissue" as used herein refer to a cell or tissue that can gives rise to a particular cell or tissue in which protein expression is to be targeted or in which translational efficiency of a codon is to be determined.

By "recombinant polypeptide" is meant a polypeptide made using recombinant techniques, i.e., through the expression of a recombinant or synthetic polynucleotide.

"Stringency" as used herein, refers to the temperature and ionic strength conditions, and presence or absence of certain organic solvents, during hybridization. The higher the stringency, the higher will be the degree of complementarity between immobilized polynucleotides and the labeled polynucleotide.

"Stringent conditions" refers to temperature and ionic conditions under which only polynucleotides having a high frequency of complementary bases will hybridize. The stringency required is nucleotide sequence dependent and depends upon the various components present during hybridization. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridizes to a complementary probe.

The term "synthetic polynucleotide" as used herein refers to a polynucleotide formed in vitro by the manipulation of a polynucleotide into a form not normally found in nature. For example, the synthetic polynucleotide can be in the form of an expression vector. Generally, such expression vectors include transcriptional and translational regulatory polynucleotide operably linked to the polynucleotide.

The term "synonymous codon" as used herein refers to a codon having a different nucleotide sequence than another codon but encoding the same amino acid as that other codon.

By "translational efficiency" is meant the efficiency of a cell's protein synthesis machinery to incorporate the amino acid encoded by a codon into a nascent polypeptide chain. This efficiency can be evidenced, for example, by the rate at which the cell is able to synthesize the polypeptide from an RNA template comprising the codon, or by the amount of the polypeptide synthesized from such a template.

By "vector" is meant a polynucleotide molecule, preferably a DNA molecule derived, for example, from a plasmid, bacteriophage, or plant virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

2. Method of the Invention

The present invention is based, at least in part, on the discovery that different but synonymous stretches of identical codons fused respectively in frame with a reporter polynucleotide can give rise to different levels of reporter protein expressed within a given cell type. Not wishing to be bound by any particular theory, it is believed that a tandem series of identical codons causes a ribosome to pause during translation if the iso-tRNA corresponding to the identical codons is limiting. In this regard, it is known that ribosomal pausing leads to a failure to complete a nascent polypeptide chain and an uncoupling of transcription and translation. Accordingly, the levels of reporter protein expressed in the different cells or tissues are sensitive to the intracellular abundance of the iso-tRNA species corresponding to the identical codons and, therefore, provide a direct correlation of a cell's or tissue's preference for translating a given codon. This means, for example, that if the levels of the reporter protein obtained in a cell or tissue type to which a synthetic construct having a tandem series of identical first codons is provided are lower than the levels expressed in the same cell or tissue type to which a different synthetic construct having a tandem series of identical second codons is provided (i.e., wherein the first codons are different from, but synonymous with, the second codons), then it can be deduced that the cell or tissue has a higher preference for the second codon relative to the first codon with respect to translation. Put another way, the second codon has a higher translational efficiency compared to the first codon in the cell or tissue type.

With regard to differential protein expression between different cell or tissue types, it will be appreciated that if the levels of the reporter protein obtained in a target cell or tissue type to which a synthetic construct having a tandem series of identical codons is provided are lower than the levels expressed in the another cell or tissue type to which the same synthetic construct is provided, then it can be deduced that the target cell or tissue has a higher preference for the codon relative to the other cell or tissue with respect to translation. Put another way, the codon has a higher translational efficiency in the target cell or tissue relative to the other cell or tissue type.

As used herein, expression of a protein in a tissue refers alternatively to expression of the protein within a cell of the tissue or production of the protein within a cell and export of the protein from the cell to, for example, the extracellular matrix of a tissue.

Suitably, the tandem repeat comprises at least three identical codons. Preferably, the tandem repeat comprises four identical codons, more preferably five or seven identical codons and most preferably six identical codons.

The tandem repeat can be fused at a location adjacent to, or within, the reporter polynucleotide. The location is preferably selected such that the tandem repeat interferes with translation of at least a detectable portion of the reporter protein such that expression of the protein can be detected or assessed. Preferably, the tandem repeat is located immediately upstream (translationally) from the reporter polynucleotide.

It is of course possible that a tandem repeat of identical amino acid residues (e.g., an oligo-proline repeat) can render the reporter protein unstable. Typically, protein instability is detected when expression of the reporter gene is not detectable with any choice of isoaccepting codon specific for the amino acid corresponding to the tandem repeat. The inventors have found in this regard that protein instability can be alleviated by use of at least one spacer codon within the tandem repeat of identical codons, wherein the spacer codon encodes a neutral amino acid.

The at least one spacer codon can be placed adjacent to, or interposed between, some or all of the identical codons corresponding to the tandem repeat. For example, a suitable interposition for a penta-repeat of identical codons can be selected from the group consisting of: (a) I-S-I-S-I-S-I-S-I-S; (b) S-I-S-I-S-I-S-I-S-I; (c) I-S-I-S-I-I-S-I; (d) I-S-I-I-S-I-S-I; (e) I-S-I-S-I-I-I; (f) I-I-S-I-S-I-I; (g) I-I-I-S-I-S-I; (h) I-S-I-I-S-I-I; (i) I-I-S-I-I-S-I; (j) I-S-I-I-I-S-I; (k) I-S-I-I-I-I; (l) I-I-S-I-I-I; (m) I-I-I-S-I-I; and (n) I-I-I-I-S-I, wherein I corresponds to an identical codon of a tandem repeat and S corresponds to a spacer codon.

Preferably, a spacer codon is efficiently translated in the cell or tissue type relative to other synonymous codons. This is important so that translation of the spacer codon is not rate limiting. The neutral amino acid includes, but is not restricted to, alanine and glycine.

The reporter polynucleotide can encode any suitable protein for which expression can be detected directly or indirectly such as by suitable assay. Suitable reporter polynucleotides include, but are not restricted to, polynucleotides encoding β-galactosidase, firefly luciferase, alkaline phosphatase, chloramphenicol acetyltransferase (CAT), β-glucuronidase (GUS), herbicide resistance genes such as the bialophos resistance (BAR) gene that confers resistance to the herbicide BASTA, and green fluorescent protein (GFP). Assays for the activities associated with such proteins are known by those of skill in the art. Preferably, the reporter polynucleotide encodes GFP.

Persons of skill in the art will appreciate that reporter polynucleotides need not correspond to a full-length gene encoding a particular reporter protein. In this regard, the invention also contemplates reporter polynucleotide sub-sequences encoding desired portions of a parent reporter protein, wherein an activity or function of the parent protein is retained in said portions. A polynucleotide sub-sequence encodes a domain of the reporter protein having an activity associated therewith and preferably encodes at least 10, 20, 50, 100, 150, or 500 contiguous amino acid residues of the reporter protein.

The instant method is applicable to any suitable cell or tissue type and, hence, is not restricted to application to mammalian cells/tissues. Accordingly, the cell or tissue type can be of any animal or plant origin. The cell or tissue type can be of any suitable lineage. For example, a suitable cell can include a eukaryotic cell, and preferably a cell or cell line capable of being grown in vitro. Suitable cell lines can include, for example, CV-1 cells, COS cells, yeast or spodoptera cells. The invention also contemplates cells that can be prokaryotic in origin.

Suitable methods for isolating particular cells or tissues are known to those of skill in the art. For example, one can take advantage of one or more particular characteristics of a cell or tissue to specifically isolate the cell or tissue from a heterogeneous population. Such characteristics include, but are not limited to, anatomical location of a tissue, cell density, cell size, cell morphology, cellular metabolic activity, cell uptake of ions such as $Ca^{2+}$, $K^+$, and $H^+$ ions, cell uptake of compounds such as stains, markers expressed on the cell surface, protein fluorescence, and membrane potential. Suitable methods that can be used in this regard include surgical removal of tissue, flow cytometry techniques such as fluorescence-activated cell sorting (FACS), immunoaffinity separation (e.g., magnetic bead separation such as Dynabead™ separation), density separation (e.g., metrizamide, Percoll™, or Ficoll™ gradient centrifugation), and cell-type specific density separation.

In an alternate embodiment, progenitor cells or tissues can be used for initially introducing the synthetic construct. Any suitable progenitor cell or tissue can be used which gives rise to a particular cell or tissue of interest for which codon preference is to be ascertained. For example, a suitable progenitor cell can comprise an undifferentiated cell. In the case of a plant, a suitable progenitor cell and tissue can include a meristematic cell and a callus tissue, respectively.

In another embodiment, the synthetic construct can be introduced first into an organism or part thereof before subsequent expression of the construct in a particular cell or tissue type. Any suitable organism is contemplated by the invention including unicellular and as multi-cellular organisms. Exemplary multi-cellular organisms include plants and animals such as mammals (e.g., humans).

The invention further provides a synthetic construct comprising a reporter polynucleotide fused in frame with a tandem repeat of (e.g., 2, 3, 4, 5, 6, or 7 or more) identical codons, wherein said reporter polynucleotide encodes a reporter protein, and wherein said synthetic construct is operably linked to one or more regulatory polynucleotides.

The construction of the synthetic construct can be effected by any suitable technique. For example, in vitro mutagenesis methods can be employed, which are known to those of skill in the art. Suitable mutagenesis methods are described for example in the relevant sections of Ausubel, et al. (supra) and of Sambrook, et al., (supra) which are incorporated herein by reference. Alternatively, suitable methods for altering DNA are set forth, for example, in U.S. Pat. Nos. 4,184,917, 4,321,365 and 4,351,901, which are incorporated herein by reference. Instead of in vitro mutagenesis, the synthetic construct can be synthesized de novo using readily available machinery. Sequential synthesis of DNA is described, for example, in U.S. Pat. No 4,293,652, which is incorporated herein by reference. However, it should be noted that the present invention is not dependent on, and not directed to, any one particular technique for constructing the synthetic construct.

Regulatory polynucleotides which can be utilized to regulate expression of the synthetic construct include, but are not limited to, a promoter, an enhancer, and a transcriptional terminator. Such regulatory polynucleotides are known to those of skill in the art. The construct preferably comprises at least one promoter. Suitable promoters that can be utilized to induce expression of the polynucleotides of the invention include constitutive promoters and inducible promoters.

The step of introducing the synthetic construct into a particular cell or tissue type, or into a progenitor cell or tissue thereof, or into an organism or part thereof for subsequent introduction into a particular cell or tissue will differ depending on the intended use and or species, and may involve lipofection, electroporation, micro-projectile bombardment infection by Agrobacterium tumefaciens or A rhizogenes, or protoplast fusion. Such methods are known to those skilled in the art.

Alternatively, the step of introduction may involve non-viral and viral vectors, cationic liposomes, retroviruses and adenoviruses such as, for example, described in Mulligan, R. C., (1993 Science 260 926–932) which is incorporated herein by reference. Such methods may include:

A. Local application of the synthetic nucleic acid sequence by injection (Wolff et al., 1990, Science 247 1465–1468, which is incorporated herein by reference), surgical implantation, instillation or any other means. This method may also be used in combination with local application by injection, surgical implantation, instillation or any other means, of cells responsive to the reporter protein encoded by the synthetic construct. This method may also be used in combination with local application by injection, surgical implantation, instillation or any other means, of another factor or factors required for the activity of said reporter protein.

B. General systemic delivery by injection of DNA, (Calabretta et al., 1993, Cancer Treat. Rev. 19 169–179, which is incorporated herein by reference), or RNA, alone or in combination with liposomes (Zhu et al., 1993, Science 261 209–212, which is incorporated herein by reference), viral capsids or nanoparticles (Bertling et al., 1991, Biotech. Appl. Biochem. 13 390–405, which is incorporated herein by reference) or any other mediator of delivery. Improved targeting might be achieved by linking the synthetic construct to a targeting molecule (the so-called "magic bullet" approach employing for example, an antibody), or by local application by injection, surgical implantation or any other means, of another factor or factors required for the activity of the protein produced from said synthetic construct, or of cells responsive to said reporter protein.

C. Injection or implantation or delivery by any means, of cells that have been modified ex vivo by transfection (for example, in the presence of calcium phosphate: Chen et al., 1987, Mole. Cell Biochem. 7 2745–2752, or of cationic lipids and polyamines: Rose et al., 1991, BioTech. 10 520–525, which articles are incorporated herein by reference), infection, injection, electroporation (Shigekawa et al., 1988, BioTech. 6 742–751, which is incorporated herein by reference) or any other way so as to increase the expression of said synthetic construct in those cells. The modification may be mediated by plasmid, bacteriophage, cosmid, viral (such as adenoviral or retroviral; Mulligan, 1993, Science 260 926–932; Miller, 1992, Nature 357 455–460; Salmons et al., 1993, Hum. Gen. Ther. 4 129–141, which articles are incorporated herein by reference) or other vectors, or other agents of modification such as liposomes (Zhu et al., 1993, Science 261 209–212, which is incorporated herein by reference), viral capsids or nanoparticles (Bertling et al., 1991, Biotech. Appl. Biochem. 13 390–405, which is incorporated herein by reference), or any other mediator of modification. The use of cells as a delivery vehicle for genes or gene products has been described by Barr et al., 1991, Science 254 1507–1512 and by Dhawan et al., 1991, Science 254 1509–1512, which articles are incorporated herein by reference. Treated cells may be delivered in combination with any nutrient, growth factor, matrix or other agent that will promote their survival in the treated subject.

Advantageously, the translational efficiencies of different codons may be determined by comparing expression of the reporter protein in a given cell or tissue type or between different cell or tissue types. One of ordinary skill in the art will thereby be able to determine a "codon preference table" for one or more cells or tissues. Comparison of codon preference tables relating to different cell or tissue types may be used to identify codons for tailoring a synthetic polynucleotide to target expression of a protein to a particular cell or tissue, as described hereinafter. Comparison of codons within a codon preference table for a particular cell or tissue type can be used to identify codons for tailoring a synthetic polynucleotide to express a protein at higher or lower levels in that cell or tissue type than a parent polynucleotide, as described hereinafter.

The invention further contemplates cells or tissues containing therein the synthetic construct of the invention, or alternatively, cells or tissues produced from the method of the invention.

3. Synthetic Polynucleotides for Targeting Protein Expression to a Particular Cell or Tissue The invention also provides an improved method of constructing a synthetic polynucleotide from which a protein is selectively expressible in a target cell of an organism, relative to another cell of the organism. This method is based in part on the method disclosed in copending International application PCT/AU98/00530 (the entire contents of which are hereby incorporated by reference) in which a first codon of a parent polynucleotide is replaced with a synonymous codon which has a higher translational efficiency in said target cell than in said other cell. The improved method of the invention is characterized by selecting the first and synonymous codons by comparing translational efficiencies of individual codons in said target cell relative to said other cell using the method broadly described is Section 2.

3.1 Selection of Synonymous and First Codons

The present method preferably includes the step of selecting the codons such that the synonymous codon has a higher translational efficiency in said target cell or tissue ("cell or tissue" is sometimes referred to herein as "cell/tissue") relative to said one or more other cells or tissues.

A method for determining translational efficiencies of different codons in and between different cells or tissues is described in detail in Section 2. The translational efficiencies so determined can be used to identify which isocoding triplets are differentially translated between the different cells or tissues. In a typical scenario, there will be: (A) codons with higher translational efficiencies in a target cell/tissue relative to one or more other cells/tissues; (B) codons with higher translational efficiencies in the one or more other cells/tissues relative to the target cell/tissue; and (C) codons with about the same translational efficiencies in the target cell/tissue relative to the one or more other cells/tissues. Synonymous codons are selected such that they correspond to (A) codons. Preferably, a synonymous codon is selected such that it has the largest difference in translational efficiency in the target cell or tissue relative to the existing codon (sometimes referred to as a "first codon") that it replaces. Existing codons in a parent polynucleotide are preferably selected such that they do not have the same translational bias as the synonymous codons with respect to the target cell/tissue and the one or more other cell/tissue (i.e., existing codons should preferably not correspond to (A) codons). However, existing codons can have similar translational efficiencies in each of the target cell/tissue and the one or more other cells/tissues (i.e., existing codons can correspond to (C) codons. They can also have a translational bias opposite to that of the synonymous codons (i.e., existing codons can, and preferably do, correspond to (B) codons).

Suitably, a synonymous codon has a translational efficiency in the target cell/tissue that is at least 110%, preferably at least 200%, more preferably at least 500%, and still more preferably at least 1000%, of that in the other cell(s)/tissue(s). In the case of two or more synonymous codons having similar translational efficiencies in the target cell/tissue relative to the other cell(s)/tissue(s), it will be appreciated that any one of these codons can be used to replace the existing codon.

It is preferable but not necessary to replace all the existing codons of the parent polynucleotide with synonymous codons having higher translational efficiencies in the target cell/tissue compared to the other cells/tissues. Increased expression can be accomplished even with partial replacement. Suitably, the replacement step affects 5%, 10%, 15%, 20%, 25%, 30%, more preferably 35%, 40%, 50%, 60%, 70% or more of the existing codons of the parent polynucleotide.

The difference in level of protein expressed in the target cell/tissue from a synthetic polynucleotide relative to that expressed in the other cell(s)/tissue(s) depends on the percentage of existing codons replaced by synonymous codons, and the difference in translational efficiencies of the synonymous codons in the target cell/tissue relative to the other cell(s)/tissue(s). Put another way, the fewer such replacements, and/or the smaller the difference in translational efficiencies of the synonymous between the different cells/tissues, the smaller the difference in protein expression between the target cell/tissue and the other cell(s)/tissue(s) will be. Conversely, the more such replacements, and/or the greater the difference in translational efficiencies of the synonymous codons between the different cells/tissues, the greater the difference in protein expression between the target cell/tissue and the other cell(s)/tissue(s) will be. The inventors have found in this respect that a protein can be expressed from a synthetic polynucleotide in a target cell/tissue at levels greater than 10,000-fold over those expressed in another cell/tissue.

In a preferred embodiment, the synonymous codon is a codon which has a higher translational efficiency in the target cell or tissue relative to a precursor cell or tissue of the target cell or tissue.

In an alternate embodiment, the synonymous codon is a codon which has a higher translational efficiency in the target cell or tissue relative to a cell or tissue derived from said target cell or tissue.

The two codons can be selected by measuring translational efficiencies of different codons in the target cell or tissue relative to the one or more other cells or tissues and identifying the at least one existing codon and the synonymous codon based on this measurement.

Suitably, the synonymous codon corresponds to a reporter construct from which the reporter protein is expressed in said target cell at a level that is at least 110%, preferably at least 200%, more preferably at least 500%, and most preferably at least 1000%, of that expressed from the said reporter construct in said other cell.

3.2 Construction of Synthetic Polynucleotides

The step of replacing a synonymous codon for said first codon in a parent polynucleotide may be effected by any suitable technique. For example, in vitro mutagenesis methods may be employed as for example discussed in Section 2.

It is not necessary to replace all the first codons of the parent polynucleotide with synonymous codons each corresponding to a codon that has a higher translational efficiency in the target cell relative to said other cell. Increased expression may be accomplished even with partial replacement. Preferably, the replacing step affects 5%, 10%, 15%, 20%, 25%, 30%, more preferably 35%, 40%, 50%, 60%, 70% or more of the existing codons of the parent nucleic acid sequence.

The parent polynucleotide is preferably a natural gene.

The parent polynucleotide may be obtained from a plant or an animal. Alternatively, the parent polynucleotide may be obtained from any other eukaryotic organism or a prokaryotic organism. In a preferred embodiment, the parent polynucleotide is obtained from a pathogenic organism. In such a case, a natural host of the pathogenic organism is preferably a plant or animal. For example, the pathogenic organism may be a yeast, bacterium or virus. However, it will be understood that the parent polynucleotide need not be obtained from the organism in which a protein is to be expressed but may be obtained from any suitable source such as from another eukaryotic or prokaryotic organism.

Suitable proteins which may be used for selective expression in accordance with the invention include, but are not limited to the cystic fibrosis transmembrane conductance regulator (CFTR) protein, and adenosine deaminase (ADA). In the case of CFTR, a parent nucleic acid sequence encoding the CFTR protein which may be utilized to produce the synthetic nucleic acid sequence is described, for example, in Riordan et al (1989, Science 245 1066–1073), and in the GenBank database under Accession No. HUMCFTRM, which are incorporated herein by reference.

Regulatory polynucleotides which may be utilized to regulate expression of the synthetic polynucleotide include, but are not limited to, a promoter, an enhancer, and a transcriptional terminator. Such regulatory polynucleotides are known to those of skill in the art. The construct preferably comprises at least one promoter. Suitable promoters that can be utilized to induce expression of the synthetic polynucleotides of the invention include constitutive promoters and inducible promoters.

Synthetic polynucleotides according to the invention may be operably linked to one or more regulatory sequences in the form of an expression vector.

The invention also contemplates synthetic polynucleotides encoding one or more desired portions of the protein to be expressed. A polynucleotide encodes a domain of a protein having a function associated therewith, or which is otherwise detectable, and preferably encodes at least 10, 20, 50, 100, 150, or 500 contiguous amino acid residues of the protein.

4. Synthetic Polynucleotides for Enhanced Protein Expression in a Particular Cell or Tissue In contrast to differential protein expression between different cells/tissues, it will be appreciated that a synthetic polynucleotide may be tailored with synonymous codons such that expression of a protein in a target cell is enhanced. In this regard, the difference in level of protein expressed in the target cell/tissue from a synthetic polynucleotide relative to that expressed from a parent polynucleotide depends on the percentage of existing codons replaced by synonymous codons, and the difference in translational efficiencies between the existing codons and the synonymous codons in the target cell/tissue. Put another way, the fewer such replacements, and/or the smaller the difference in translational efficiencies between the synonymous and existing codons, the smaller the difference in protein expression between the synthetic polynucleotide and parent polynucleotide will be. Conversely, the more such replacements, and/or the greater the difference in translational efficiencies between the synonymous and existing codons, the greater the difference in protein expression between the synthetic polynucleotide and parent polynucleotide will be. The inventors have found in this respect that a protein can be expressed from a synthetic polynucleotide in a target cell/tissue at levels greater than 10,000-fold than from a parent polynucleotide.

Preferably, the at least one existing codon and the synonymous codon are selected such that said protein is expressed from said synthetic polynucleotide in said target cell or tissue at a level which is at least 110%, preferably at least 200%, more preferably at least 500%, and most preferably at least 1000%, of that expressed from said parent polynucleotide in said target cell or tissue.

The invention is further described with reference to the following non-limiting examples.

EXAMPLE 1

Construction of Expression Vectors for Determining Relative Codon Preferences in Mammalian Cells Synthetic gfp genes were constructed in which a single artificial start codon (ATG) followed by a stretch of five identical codons is fused in frame immediately upstream of a gfp coding sequence. A reverse oligonucleotide primer (SEQ ID NO:185; sequence complementary to the termination codon for GFP, is underlined), and a suite of forward oligonucleotide primers (SEQ ID NO: 126 through 184; the first codon of GFP, is underlined) were synthesized and used for PCR amplification of a humanized gfp gene (SEQ ID NO:124) (GIBCO) as template with Taq DNA polymerase (Amplification parameters: 95° C./30 sec; 52° C./30 sec; 72° C./1 min; 30 cycles). The amplified fragments have nucleic acid sequences and deduced amino acid sequences as shown in SEQ ID NO:1 through 124.

In summary, the synthetic fragments contain an artificial start codon followed by a tandem repeat of five identical codons specific for a given iso-tRNA species. The tandem repeat immediately precedes the second codon of the gfp gene. The synthetic fragments by SEQ ID NO, and encoded tandem repeat, are presented in the TABLE 1.

The amplified fragments were cloned between the EcoRI and KpnI sites of the mammalian expression vector pCDNA3 containing SV40 ori (Invitrogen) and the CMV promoter.

Transfection of COS-1 Cells

COS-1 cells were grown continuously in DMEM media supplemented with 10% fetal calf serum (FCS), glutamine, penicillin and streptomycin. Cells were passaged from a 150 cm² flask into multiple 25 cm² flasks. Cells were transfected using a QIAGEN Effectene™ transfection kit (and the manufacturer's instructions, incorporated herein by reference) when confluency of the cells was between 60–80%. Briefly, 1 µg of plasmid DNA was diluted into 10 µL of filtered TE buffer and 140 µL of QIAGEN™ Buffer EC. Eight microliters of QIAGEN™ Enhancer was added followed by vortexing and incubation at room temperature for 2–5 min. QIAGEN™ Effectene (10 µL) was added followed by vortexing for 10 seconds and a further incubation at room temperature for 10 min. The cells were washed once in 1×PBS followed by re-suspension in fresh media (1 mL). After 48 hrs, cells were harvested and washed in 1×PBA (phosphate buffered saline plus azide). Cells adhering to the flask were removed by scraping with a cell scraper. Cells were then filtered through a 70 µm filter before addition of 300 µL of 2% paraformaldehyde and 300 µL of 10×FCS. Cells were kept on ice in the dark until FACS analysis.

Synthetic gfp mRNA expression of transfected cells was tested by reverse transcriptase PCR. GFP protein expression was analyzed by confocal microscopy and flow cytometry.

Confocal Microscopy

Transfected COS-1 cells were examined using a Bio-Rad MRC-600 laser-scanning confocal microscope equipped with a krypton-argon laser and filter sets suitable for the detection of fluorescein and Texas red dyes (Bio-Rad KlyK2), and a Nikon 603 PlanApo™ numerical aperture 1.2 water-immersion objective. Dual-channel confocal images and video montages of the transfected cells can be suitably composed using ADOBE PhotoShop™.

Flow Cytometry

Transfected COS-1 cells were analyzed with a Becton Dickinson™ Flow cytometer Elite II. Omega Filters™ allowed detection of green fluorescence emission (EMI510/20—collects light from 490–530 nm) and yellow fluorescence emission (EM2 550/30—collects light form 525–580 nm) from the transfected cells.

Results

A series of 64 reporter constructs (see TABLE 1) was made and validated, in which the gfp gene is preceded in frame by a tandem repeat of 5 identical codons. Together, the series covers the entire set of isoaccepting codon triplets.

The series was transfected into a single cell line, and expression levels measured by flow cytometry (see TABLE 2). Overall, the expression level of the reporter gene constructs in the cell line varied over a range of 20-fold, according to the triplet used in the reporter construct. Repeated determinations on the same construct showed excellent inter-assay reproducibility ($r^2$=0.9). Variation in expression levels across the isoaccepting codons for a single amino acid ranged from 1.4-fold for valine to 13-fold for threonine, with a median of about 4-fold. Variation in expression between amino acids was of the same order of magnitude. The order of magnitude of the effect is defined as an average of 4 fold per amino acid if 5 copies are incorporated, compatible with an extreme in range of expression levels of up to $(1.6)^{200}=10^{86}$ over an average 200-amino acid residues protein. This figure is derived as:

$$[1+((4-1)(\text{range of reporter construct expression})/5(\text{no of triplets in the reporter construct}))]^{200(no\ of\ amino\ acid\ residues\ in\ the\ protein)}$$

and is more than sufficient to explain the observed differences in expression of mammalian genes according to codon usage.

The results presented in TABLE 2 also show that various codons in the undifferentiated epithelial cells (COS-1) have translational efficiencies at least two-fold higher or two-fold lower relative to those of their corresponding synonymous codons. Representative codons having at least a two-fold higher translational efficiency relative to at least one of their corresponding synonymous codons include aga (Arg), cgg (Arg), tgc (Cys), gga (Gly), ggc (Gly), ccg (Pro), cga (Pro), aca (Thr), acg (Thr), and act (Thr). Thus, these codons appear to be preferred for translation in the undifferentiated epithelial cells. By contrast, representative codons having at least a two-fold lower translational efficiency relative to at least one of their corresponding synonymous codons include agg (Arg), tgt (Cys), ggg (Gly), ggt (Gly), ccc (Pro), cct (Pro), and acc (Thr). These latter codons would therefore appear to be less preferred for translation in the undifferentiated epithelial cells. Accordingly, if higher protein expression is required within undifferentiated epithelial cells such as COS-1 cells, the preferred codons should be used to replace any existing codons of a parent polynucleotide encoding the protein that correspond to the less preferred codons. In this respect, a codon substitution algorithm for increasing protein expression in non-differentiated epithelial cells is presented in TABLE 3. However, if lower protein expression is required in non-differentiated epithelial cells, the less preferred codons should be used to replace any existing codons of the parent polynucleotide that correspond to the preferred codons.

The disclosure of every patent, patent application, and publication cited herein is hereby incorporated by reference in its entirety.

The present invention has been described in terms of particular embodiments found or proposed by the present inventors to comprise preferred modes for the practice of the invention. Those of skill in the art will appreciate that, in light of the present disclosure, numerous modifications and changes can be made in the particular embodiments exemplified without departing from the scope of the invention. All such modifications are intended to be included within the scope of the appended claims.

Table 1

Synthetic gfp constructs are tabulated by SEQ ID NO and by the codon corresponding to the tandem repeat of five identical codons immediately upstream of the gfp gene.

Table 2

Mean fluorescence intensities of up to four different samples of transiently transfected COS-1 cells are shown (Green mean 1–4). Synthetic gfp constructs are tabulated by SEQ ID NO and by the codon corresponding to the tandem repeat immediately upstream of the gfp gene.

Table 3

Input codons and output codons represent, respectively, synonymous codons and existing (i.e., "first") codons according to the invention. Change means an actual change of a codon.

TABLE 1

TABLES
Synthetic fragments and tandem repeats encoded thereby.

| SEQ ID NO | Tandem repeat |
| --- | --- |
| 1 | Ala(GCA) × 5 |
| 3 | Ala(GCC) × 5 |
| 5 | Ala(GCG) × 5 |
| 7 | Ala(GCT) × 5 |
| 9 | Arg(AGA) × 5 |
| 11 | Arg(AGG) × 5 |
| 13 | Arg(CGA) × 5 |
| 15 | Arg(CGC) × 5 |
| 17 | Arg(CGG) × 5 |
| 19 | Arg(CGT) × 5 |
| 21 | Asn(AAC) × 5 |
| 23 | Asn(AAT) × 5 |
| 25 | Asp(GAC) × 5 |
| 27 | Asp(GAT) × 5 |
| 29 | Cys(TGC) × 5 |
| 31 | Cys(TGT) × 5 |
| 33 | Gln(CAA) × 5 |
| 35 | Gln(CAG) × 5 |
| 37 | Gly(GAA) × 5 |
| 39 | Gly(GAG) × 5 |
| 41 | Gly(GGA) × 5 |
| 43 | Gly(GGC) × 5 |
| 45 | Gly(GGG) × 5 |
| 47 | Gly(GGT) × 5 |
| 49 | His(CAC) × 5 |
| 51 | His(CAT) × 5 |
| 53 | Ile(ATA) × 5 |
| 55 | Ile(ATC) × 5 |
| 57 | Ile(ATT) × 5 |
| 59 | Leu(CTA) × 5 |
| 61 | Leu(CTC) × 5 |
| 63 | Leu(CTG) × 5 |
| 65 | Leu(CTT) × 5 |
| 67 | Leu(TTA) × 5 |
| 69 | Leu(TTG) × 5 |

TABLE 1-continued

TABLES
Synthetic fragments and tandem repeats encoded thereby.

| SEQ ID NO | Tandem repeat |
|---|---|
| 71 | Lys(AAA) × 5 |
| 73 | Lys(AAG) × 5 |
| 75 | Phe(TTT) × 5 |
| 77 | Phe(TTC) × 5 |
| 79 | Pro(CCC) × 5 |
| 81 | Pro(CCG) × 5 |
| 83 | Pro(CCT) × 5 |
| 85 | Pro(CGA) × 5 |
| 87 | Ser(AGC) × 5 |
| 89 | Ser(AGT) × 5 |
| 91 | Ser(TCA) × 5 |
| 93 | Ser(TCC) × 5 |
| 95 | Ser(TCG) × 5 |
| 97 | Ser(TCT) × 5 |
| 99 | Thr(ACA) × 5 |
| 101 | Thr(ACC) × 5 |
| 103 | Thr(ACG) × 5 |
| 105 | Thr(ACT) × 5 |
| 107 | Trp(TGG) × 5 |
| 109 | Tyr(TAT) × 5 |
| 111 | Tyr(TAG) × 5 |
| 113 | Val(GTA) × 5 |
| 115 | Val(GTC) × 5 |
| 117 | Val(GTG) × 5 |
| 119 | Val(GTT) × 5 |
| 121 | Stop(TAA) × 5 |
| 122 | Stop(TAG) × 5 |
| 123 | Stop(TGA) × 5 |
| 124 | control |

TABLE 2

GFP protein expression in transiently transfected COS-1 cells

| SEQ ID NO | Codon | [DNA] (µg/mL) | Green mean 1 | Green mean 2 | Green mean 3 | Green mean 4 | Average |
|---|---|---|---|---|---|---|---|
| 1 | Ala(GCA) | 1.07 | 45.70 | 54.40 | | | 50.05 |
| 3 | Ala(GCC) | 1.10 | 43.70 | 50.00 | | | 46.85 |
| 5 | Ala(GCG) | 0.03 | 28.50 | 42.40 | | | 35.45 |
| 7 | Ala(GCT) | 0.56 | 11.60 | 48.30 | | | 29.95 |
| 9 | Arg(AGA) | 0.90 | 29.00 | 33.00 | | | 31.00 |
| 11 | Arg(AGG) | 0.34 | 7.35 | 2.88 | | | 5.12 |
| 13 | Arg(CGA) | 1.00 | 18.30 | 14.20 | | | 16.25 |
| 15 | Arg(CGC) | 0.86 | 14.60 | 16.00 | | | 15.30 |
| 17 | Arg(CGG) | 1.00 | 22.50 | 20.60 | | | 21.55 |
| 19 | Arg(CGT) | 0.68 | 21.70 | 32.20 | | | 26.95 |
| 21 | Asn(AAC) | 0.02 | | | | | |
| 23 | Asn(AAT) | 0.38 | 28.30 | 8.22 | | | 18.26 |
| 25 | Asp(GAC) | 0.46 | 24.90 | 17.80 | | | 21.35 |
| 27 | Asp(GAT) | 1.39 | 14.50 | 18.90 | | | 16.70 |
| 29 | Cys(TGC) | 0.68 | 21.90 | 16.10 | | | 19.00 |
| 31 | Cys(TGT) | 1.14 | 5.95 | 5.89 | | | 5.92 |
| 33 | Gln(CAA) | 0.28 | 26.50 | 43.50 | | | 35.00 |
| 35 | Gln(CAG) | 1.98 | 44.70 | 48.60 | | | 46.65 |
| 37 | Glu(GAA) | 0.60 | 10.30 | 22.70 | | | 16.50 |
| 39 | Glu(GAG) | 0.43 | 3.86 | | | | |
| 41 | Gly(GGA) | 0.33 | 28.80 | 36.30 | | | 32.55 |
| 43 | Gly(GGC) | 1.62 | 17.80 | 28.10 | | | 22.95 |
| 45 | Gly(GGG) | 1.15 | 6.43 | 4.96 | | | 5.70 |
| 47 | Gly(GGT) | 1.39 | 7.12 | 4.02 | | | 5.57 |
| 49 | His(CAC) | 1.62 | 29.90 | 39.70 | | | 34.80 |
| 51 | His(CAT) | 1.69 | 43.40 | 37.20 | | | 40.30 |
| 53 | Ile(ATA) | 0.69 | 2.76 | 3.98 | | | 3.37 |
| 55 | Ile(ATC) | 1.52 | 4.12 | 2.83 | | | 3.48 |
| 57 | Ile(ATT) | 1.77 | 3.19 | 3.16 | | | 3.18 |
| 59 | Leu(CTA) | 0.10 | 15.00 | 3.01 | 5.26 | 2.44 | 6.43 |
| 61 | Leu(CTC) | 1.74 | 2.70 | 2.92 | 2.56 | | 2.73 |
| 63 | Leu(CTG) | 0.41 | 2.80 | 7.51 | 2.63 | | 4.31 |
| 65 | Leu(CTT) | 1.43 | 3.17 | 3.56 | 2.70 | | 3.14 |
| 67 | Leu(TTA) | 0.62 | 3.85 | 3.91 | 2.66 | | 3.47 |
| 69 | Leu(TTG) | 0.70 | 2.87 | 4.63 | 2.85 | | 3.45 |
| 71 | Lys(AAA) | 0.10 | 11.90 | 8.24 | | | 10.07 |
| 73 | Lys(AAG) | 0.56 | 19.20 | 16.00 | | | 17.60 |
| 75 | Phe(TTT) | 2.28 | 2.67 | | | | |
| 77 | Phe(TTC) | 1.65 | 4.35 | | | | |
| 79 | Pro(CCC) | 0.40 | 12.00 | 8.95 | | | 10.48 |
| 81 | Pro(CCG) | 0.13 | 17.40 | 25.40 | | | 21.40 |
| 83 | Pro(CCT) | 0.40 | 10.60 | 9.89 | | | 10.25 |
| 85 | Pro(CGA) | 0.17 | 27.20 | 34.80 | | | 31.00 |
| 87 | Ser(AGC) | 0.03 | 62.40 | | | | |
| 89 | Ser(AGT) | 0.81 | 23.10 | | | | |
| 91 | Ser(TCA) | 0.08 | 30.70 | 37.20 | | | 33.95 |
| 93 | Ser(TCC) | 1.68 | 32.90 | | | | |
| 95 | Ser(TCG) | 1.58 | 60.00 | | | | |
| 97 | Ser(TCT) | 0.62 | 26.80 | 40.70 | | | 33.75 |
| 99 | Thr(ACA) | 1.70 | 37.80 | 39.90 | | | 38.85 |
| 101 | Thr(ACC) | 7.69 | 3.48 | 2.75 | | | 3.12 |
| 103 | Thr(ACG) | 1.06 | 36.10 | 44.10 | | | 40.10 |
| 105 | Thr(ACT) | 1.42 | 38.80 | 42.60 | | | 40.70 |
| 107 | Trp(TGG) | 1.19 | 5.21 | 4.29 | | | 4.75 |
| 109 | Tyr(TAT) | 0.02 | | | | | |
| 111 | Tyr(TAC) | 1.07 | 12.00 | 15.00 | | | 13.50 |
| 113 | Val(GTA) | 0.16 | 10.50 | 3.81 | | | 7.16 |
| 115 | Val(GTC) | 0.66 | 15.20 | 4.55 | 3.65 | 5.06 | 7.12 |
| 117 | Val(GTG) | 0.10 | 9.17 | 4.29 | 7.03 | 2.36 | 5.71 |
| 119 | Val(GTT) | 0.49 | 14.10 | 2.63 | 3.70 | 2.49 | 5.73 |
| 121 | stop (TAA) | 1.88 | 39.40 | 35.30 | | | 37.35 |
| 122 | stop (TAG) | 2.86 | 2.88 | 3.28 | | | 3.08 |
| 123 | stop (TGA) | 0.02 | | | | | |
| 124 GFP alone control | | 9.34 | 61.60 | 30.40 | 55.00 | | 39.09 |
| | | | 2.33 | 2.21 | 2.16 | 2.00 | 2.18 |

TABLE 3

Substitution algorithm used for high level expression in non-differentiated epithelial cells

| Input Codon | Output Codon | Amino Acid | Change |
|---|---|---|---|
| AAA | AAG | LYS | Yes |
| AAC | AAC | ASN | No |
| AAG | AAG | LYS | No |
| AAT | AAC | ASN | Yes |
| AAU | AAC | ASN | Yes |
| ACA | ACC | THR | Yes |
| ACC | ACC | THR | No |
| ACG | ACC | THR | Yes |
| ACT | ACC | THR | Yes |
| ACU | ACC | THR | Yes |
| AGA | AGG | ARG | Yes |
| AGC | AGC | SER | No |
| AGG | AGG | ARG | No |
| AGT | AGC | SER | Yes |
| AGU | AGC | SER | Yes |
| ATA | ATC | ILE | Yes |
| ATC | ATC | ILE | No |
| ATG | ATG | MET | No |
| ATT | ATC | ILE | Yes |
| AUA | ATC | ILE | Yes |
| AUC | ATC | ILE | No |
| AUG | ATG | MET | No |
| AUU | ATC | ILE | Yes |
| CAA | CAG | GLN | Yes |

TABLE 3-continued

Substitution algorithm used for high level expression in non-differentiated epithelial cells

| Input Codon | Output Codon | Amino Acid | Change |
|---|---|---|---|
| CAC | CAC | HIS | No |
| CAG | CAG | GLN | No |
| CAT | CAC | HIS | Yes |
| CAU | CAC | HIS | Yes |
| CCA | CCC | PRO | Yes |
| CCC | CCC | PRO | No |
| CCG | CCC | PRO | Yes |
| CCT | CCC | PRO | Yes |
| CCU | CCC | PRO | Yes |
| CGA | CGC | ARG | Yes |
| CGC | CGC | ARG | No |
| CGG | CGC | ARG | Yes |
| CGT | CGC | ARG | Yes |
| CGU | CGC | ARG | Yes |
| CTA | CTG | LEU | Yes |
| CTC | CTG | LEU | Yes |
| CTG | CTG | LEU | No |
| CTT | CTG | LEU | Yes |
| CUA | CTG | LEU | Yes |
| CUC | CTG | LEU | Yes |
| CUG | CTG | LEU | No |
| CUU | CTG | LEU | Yes |
| GAA | GAG | GLU | Yes |
| GAC | GAC | ASP | No |
| GAG | GAG | GLU | No |
| GAT | GAC | ASP | Yes |
| GAU | GAC | ASP | Yes |
| GCA | GCC | ALA | Yes |
| GCC | GCC | ALA | No |
| GCG | GCC | ALA | Yes |
| GCT | GCC | ALA | Yes |
| GCU | GCC | ALA | Yes |
| GGA | GGC | GLY | Yes |
| GGC | GGC | GLY | No |
| GGG | GGG | GLY | No |
| GGT | GGC | GLY | Yes |
| GGU | GGC | GLY | Yes |
| GTA | GTG | VAL | Yes |
| GTC | GTG | VAL | Yes |
| GTG | GTG | VAL | No |
| GTT | GTG | VAL | Yes |
| GUA | GTG | VAL | Yes |
| GUC | GTG | VAL | Yes |
| GUG | GTG | VAL | No |
| GUU | GTG | VAL | Yes |
| TAA | TAA | XXX | No |
| TAC | TAC | TYR | No |
| TAG | TAG | XXX | No |
| TAT | TAC | TYR | Yes |
| TCA | TCC | SER | Yes |
| TCC | TCC | SER | No |
| TCG | TCC | SER | Yes |
| TCT | TCC | SER | Yes |
| TGA | TGA | XXX | No |
| TGC | TGC | CYS | No |
| TGG | TGG | TRP | No |
| TGT | TGT | CYS | No |
| TTA | CTG | LEU | Yes |
| TTC | TTC | PHE | No |
| TTG | CTG | LEU | Yes |
| TTT | TTC | PHE | No |
| UAA | TAA | XXX | No |
| UAC | TAC | TYR | No |
| UAG | TAG | XXX | No |
| UAU | TAC | TYR | Yes |
| UCA | TCC | SER | Yes |
| UCC | TCC | SER | No |
| UCG | TCC | SER | Yes |
| UCU | TCC | SER | Yes |
| UGA | TGA | XXX | No |
| UGC | TGC | CYS | No |
| UGG | TGG | TRP | No |
| UGU | TGT | CYS | No |
| UUA | CTG | LEU | Yes |
| UUC | TTC | PHE | No |
| UUG | CTG | LEU | Yes |
| UUU | TTC | PHE | Yes |

What is claimed is:

1. A synthetic construct comprising a regulatory polynucleotide operably linked to a tandem repeat of a codon fused in frame with a reporter polynucleotide that encodes a reporter protein.

2. A vector comprising the synthetic construct of claim 1.

3. A cell comprising the synthetic construct of claim 1.

4. A cell comprising the vector of claim 2.

5. The construct of claim 1, wherein the tandem repeat comprises at least three copies of the codon.

6. The construct of claim 5, wherein the tandem repeat comprises five copies of the codon.

7. The construct of claim 5, wherein the tandem repeat comprises six copies of the codon.

8. The construct of claim 5, wherein the tandem repeat comprises seven copies of the codon.

9. The construct of claim 1, wherein the tandem repeat is fused at a location adjacent to, or within, the reporter polynucleotide.

10. The construct of claim 9, wherein the tandem repeat is fused immediately upstream of the reporter polynucleotide.

11. The construct of claim 1, wherein at least one spacer codon is located adjacent to a tandemly repeated codon.

12. The construct of claim 1, wherein at least one spacer codon is interposed between a pair of tandemly repeated codons.

13. The construct of claim 11, wherein the spacer codon is a neutral amino acid.

14. The construct of claim 12, wherein the spacer codon is a neutral amino acid.

15. The construct of claim 11, wherein the spacer codon is selected from alanine and glycine.

16. The construct of claim 12, wherein the spacer codon is selected from alanine and glycine.

17. The construct of claim 1, wherein the reporter protein is selected from the group consisting of β-galactosidase, firefly luciferase, alkaline phosphatase, chloramphenicol acetyl transferase, β-glucuronidase, green fluorescence protein and active portions thereof.

18. The construct of claim 1, wherein the reporter protein is encoded by a bialophos resistance gene that confers resistance to the herbicide BASTA.

19. The construct of claim 1, wherein the reporter protein is green fluorescence protein or an active portion thereof.

20. A synthetic construct system for determining the translational efficiencies of different codons, the system comprising a plurality of synthetic constructs, each comprising a regulatory polynucleotide operably linked to a tandem repeat of a codon fused in frame with a reporter polynucleotide that encodes a reporter protein, wherein the tandemly repeated codon of a first construct is different than the tandemly repeated codon of a second construct.

21. The system of claim 20, wherein the tandemly repeated codons of the first and second constructs encode the same amino acid.

22. The system of claim 20, wherein the tandemly repeated codons of the first and second constructs encode different amino acids.

23. The system of claim 21, comprising a set of synthetic constructs, the number of synthetic constructs of the set being equal to the number of synonymous codons that encode a first amino acid, wherein the tandemly repeated codon of each synthetic construct of the set is a synonymous codon that encodes the first amino acid and wherein different synthetic constructs of the set comprise different tandemly repeated codons.

24. The system of claim 21, comprising a first set of synthetic constructs and a second set of synthetic constructs, the number of synthetic constructs of the first set being equal to the number of synonymous codons that encode a first amino acid, the number of synthetic constructs of the second set being equal to the number of synonymous codons that encode a second amino acid, wherein the tandemly repeated codon of each synthetic construct of the first set is a synonymous codon that encodes the first amino acid, wherein the tandemly repeated codon of each synthetic construct of the second set is a synonymous codon that encodes the second amino acid and wherein different synthetic constructs of the first or second sets comprise different tandemly repeated codons.

25. The system of claim 20, wherein the tandem repeat of each of the synthetic constructs comprises at least three copies of the corresponding codon.

26. The system of claim 25, wherein the tandem repeat of each of the synthetic constructs comprises five copies of the corresponding codon.

27. The system of claim 25, wherein the tandem repeat of each of the synthetic constructs comprises six copies of the corresponding codon.

28. The system of claim 25, wherein the tandem repeat of each of the synthetic constructs comprises seven copies of the corresponding codon.

29. The system of claim 20, wherein the tandem repeat is fused at a location adjacent to, or within, the reporter polynucleotide.

30. The system of claim 29, wherein the tandem repeat is fused immediately upstream of the reporter polynucleotide.

31. The system of claim 20, wherein at least one spacer codon is located adjacent to a tandemly repeated codon.

32. The system of claim 20, wherein at least one spacer codon is interposed between a pair of tandemly repeated codons.

33. The system of claim 31, wherein the spacer codon is a neutral amino acid.

34. The system of claim 32, wherein the spacer codon is a neutral amino acid.

35. The system of claim 31, wherein the spacer codon is selected from alanine and glycine.

36. The system of claim 32, wherein the spacer codon is selected from alanine and glycine.

37. The system of claim 20, wherein the reporter protein is selected from the group consisting of β-galactosidase, firefly luciferase, alkaline phosphatase, chloramphenicol acetyl transferase, β-glucuronidase, green fluorescence protein and active portions thereof.

38. The system of claim 20, wherein the reporter protein is encoded by a bialophos resistance gene that confers resistance to the herbicide BASTA.

39. The system of claim 20, wherein the reporter protein is green fluorescence protein or an active portion thereof.

40. The construct of claim 1, wherein there are five tandemly repeated codons, the tandemly repeated codons are located immediately upstream of the reporter polynucleotide, at least one spacer codon is interspersed between a pair of tandemly repeated codons and the spacer codon is alanine.

* * * * *

SEQUENCE LISTING

<160> NUMBER OF SEQ ID NOS: 185

<210> SEQ ID NO 1
<211> LENGTH: 732
<212> TYPE: DNA
<213> ORGANISM: Artificial Sequence
<220> FEATURE:
<223> OTHER INFORMATION: Description of Artificial Sequence: Ala(GCA)
      5GFP
<220> FEATURE:
<221> NAME/KEY: CDS
<222> LOCATION: (1)..(732)

<400> SEQUENCE: 1

```
atg gca gca gca gca gca agc aag ggc gag gaa ctg ttc act ggc gtg      48
Met Ala Ala Ala Ala Ala Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30
```

```
tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
        35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys <210> SEQ ID NO 2
<211> LENGTH: 243
<212> TYPE: PRT
<213> ORGANISM: Artificial Sequence
<220> FEATURE:
<223> OTHER INFORMATION: Description of Artificial Sequence: Ala(GCA)
      5GFP

<400> SEQUENCE: 2

Met Ala Ala Ala Ala Ser Lys Gly Glu Glu Leu Phe Thr Gly Val
 1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
 50                  55                  60
```

```
Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 3
<211> LENGTH: 732
<212> TYPE: DNA
<213> ORGANISM: Artificial Sequence
<220> FEATURE:
<223> OTHER INFORMATION: Description of Artificial Sequence: Ala(GCC)
      5GFP
<220> FEATURE:
<221> NAME/KEY: CDS
<222> LOCATION: (1)..(732)

<400> SEQUENCE: 3 atg gcc gcc gcc gcc gcc agc aag ggc gag gaa ctg ttc act ggc gtg      48
Met Ala Ala Ala Ala Ala Ser Lys Gly Glu Glu Leu Phe Thr Gly Val
  1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
```

```
gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 4
<211> LENGTH: 243
<212> TYPE: PRT
<213> ORGANISM: Artificial Sequence
<220> FEATURE:
<223> OTHER INFORMATION: Description of Artificial Sequence: Ala(GCC)
      5GFP

<400> SEQUENCE: 4

```
Met Ala Ala Ala Ala Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190
```

```
Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys

<210> SEQ ID NO 5
<211> LENGTH: 732
<212> TYPE: DNA
<213> ORGANISM: Artificial Sequence
<220> FEATURE:
<223> OTHER INFORMATION: Description of Artificial Sequence: Ala(GCG)
      5GFP
<220> FEATURE:
<221> NAME/KEY: CDS
<222> LOCATION: (1)..(732)

<400> SEQUENCE: 5
```

| | | | | | | | | | | | | | | | | |
|---|---|---|---|---|---|---|---|---|---|---|---|---|---|---|---|---|
| atg | gcg | gcg | gcg | gcg | gcg | agc | aag | ggc | gag | gaa | ctg | ttc | act | ggc | gtg | 48 |
| Met | Ala | Ala | Ala | Ala | Ala | Ser | Lys | Gly | Glu | Glu | Leu | Phe | Thr | Gly | Val | |
| 1 | | | | 5 | | | | | 10 | | | | | 15 | | |
| gtc | cca | att | ctc | gtg | gaa | ctg | gat | ggc | gat | gtg | aat | ggg | cac | aaa | ttt | 96 |
| Val | Pro | Ile | Leu | Val | Glu | Leu | Asp | Gly | Asp | Val | Asn | Gly | His | Lys | Phe | |
| | | | 20 | | | | | 25 | | | | | 30 | | | |
| tct | gtc | agc | gga | gag | ggt | gaa | ggt | gat | gcc | aca | tac | gga | aag | ctc | acc | 144 |
| Ser | Val | Ser | Gly | Glu | Gly | Glu | Gly | Asp | Ala | Thr | Tyr | Gly | Lys | Leu | Thr | |
| | | 35 | | | | | 40 | | | | | 45 | | | | |
| ctg | aaa | ttc | atc | tgc | acc | act | gga | aag | ctc | cct | gtg | cca | tgg | cca | aca | 192 |
| Leu | Lys | Phe | Ile | Cys | Thr | Thr | Gly | Lys | Leu | Pro | Val | Pro | Trp | Pro | Thr | |
| 50 | | | | | 55 | | | | | 60 | | | | | | |
| ctg | gtc | act | acc | ttc | tct | tat | ggc | gtg | cag | tgc | ttt | tcc | aga | tac | cca | 240 |
| Leu | Val | Thr | Thr | Phe | Ser | Tyr | Gly | Val | Gln | Cys | Phe | Ser | Arg | Tyr | Pro | |
| 65 | | | | | 70 | | | | | 75 | | | | | 80 | |
| gac | cat | atg | aag | cag | cat | gac | ttt | ttc | aag | agc | gcc | atg | ccc | gag | ggc | 288 |
| Asp | His | Met | Lys | Gln | His | Asp | Phe | Phe | Lys | Ser | Ala | Met | Pro | Glu | Gly | |
| | | | | 85 | | | | | 90 | | | | | 95 | | |
| tat | gtg | cag | gag | aga | acc | atc | ttt | ttc | aaa | gat | gac | ggg | aac | tac | aag | 336 |
| Tyr | Val | Gln | Glu | Arg | Thr | Ile | Phe | Phe | Lys | Asp | Asp | Gly | Asn | Tyr | Lys | |
| | | | 100 | | | | | 105 | | | | | 110 | | | |
| acc | cgc | gct | gaa | gtc | aag | ttc | gaa | ggt | gac | acc | ctg | gtg | aat | aga | atc | 384 |
| Thr | Arg | Ala | Glu | Val | Lys | Phe | Glu | Gly | Asp | Thr | Leu | Val | Asn | Arg | Ile | |
| | | 115 | | | | | 120 | | | | | 125 | | | | |
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| 130 | | | | | 135 | | | | | 140 | | | | | | |
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | | 150 | | | | | 155 | | | | | 160 | |
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | | 180 | | | | | 185 | | | | | 190 | | | |
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |
| | | 195 | | | | | 200 | | | | | 205 | | | | |
| cag | tct | gcc | ctg | tct | aaa | gat | ccc | aac | gaa | aag | aga | gac | cac | atg | gtc | 672 |

```
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 6
<211> LENGTH: 243
<212> TYPE: PRT
<213> ORGANISM: Artificial Sequence
<220> FEATURE:
<223> OTHER INFORMATION: Description of Artificial Sequence: Ala(GCG)
      5GFP

<400> SEQUENCE: 6

```
Met Ala Ala Ala Ala Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 7
<211> LENGTH: 732
<212> TYPE: DNA
<213> ORGANISM: Artificial Sequence
<220> FEATURE:
<223> OTHER INFORMATION: Description of Artificial Sequence: Ala(GCT)
      5GFP
<220> FEATURE:
<221> NAME/KEY: CDS
<222> LOCATION: (1)..(732)

<400> SEQUENCE: 7

```
atg gct gct gct gct gct agc aag ggc gag gaa ctg ttc act ggc gtg       48
Met Ala Ala Ala Ala Ala Ser Lys Gly Glu Glu Leu Phe Thr Gly Val
1               5                   10                  15 gtc cca att ctc gtg gaa ctg gat ggc gat gtg aat ggg cac aaa ttt       96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc      144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca      192
Leu Lys Phe Ile Cys Thr Thr Gly Lys Leu Pro Val Pro Trp Pro Thr
    50                  55                  60 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
                100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
            115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 8
<211> LENGTH: 243
<212> TYPE: PRT
<213> ORGANISM: Artificial Sequence
<220> FEATURE:
<223> OTHER INFORMATION: Description of Artificial Sequence: Ala(GCT)
5GFP

<400> SEQUENCE: 8

```
Met Ala Ala Ala Ala Ala Ser Lys Gly Glu Glu Leu Phe Thr Gly Val
1               5                   10                  15
```

```
Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 9
<211> LENGTH: 732
<212> TYPE: DNA
<213> ORGANISM: Artificial Sequence
<220> FEATURE:
<223> OTHER INFORMATION: Description of Artificial Sequence: Arg(AGA)
      5GFP
<220> FEATURE:
<221> NAME/KEY: CDS
<222> LOCATION: (1)..(732)

<400> SEQUENCE: 9 atg aga aga aga aga aga agc aag ggc gag gaa ctg ttc act ggc gtg    48
Met Arg Arg Arg Arg Arg Ser Lys Gly Glu Glu Leu Phe Thr Gly Val
1               5                   10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
            20                  25                  30 tct gtc agc gga gag ggt gaa ggt gat gcc aca tac gga aag ctc acc   144
Ser Val Ser Gly Glu Gly Glu Gly Asp Ala Thr Tyr Gly Lys Leu Thr
        35                  40                  45 ctg aaa ttc atc tgc acc act gga aag ctc cct gtg cca tgg cca aca   192
Leu Lys Phe Ile Cys Thr Thr Gly Lys Leu Pro Val Pro Trp Pro Thr
    50                  55                  60 ctg gtc act acc ttc tct tat ggc gtg cag tgc ttt tcc aga tac cca   240
Leu Val Thr Thr Phe Ser Tyr Gly Val Gln Cys Phe Ser Arg Tyr Pro
65                  70                  75                  80
```

```
gac cat atg aag cag cat gac ttt ttc aag agc gcc atg ccc gag ggc    288
Asp His Met Lys Gln His Asp Phe Phe Lys Ser Ala Met Pro Glu Gly
            85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
        100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
    115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                   732
Leu Tyr Lys <210> SEQ ID NO 10
<211> LENGTH: 243
<212> TYPE: PRT
<213> ORGANISM: Artificial Sequence
<220> FEATURE:
<223> OTHER INFORMATION: Description of Artificial Sequence: Arg(AGA)
      5GFP

<400> SEQUENCE: 10

Met Arg Arg Arg Arg Ser Lys Gly Glu Glu Leu Phe Thr Gly Val
  1               5                  10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
```

-continued

```
                130                 135                 140
Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 11
<211> LENGTH: 732
<212> TYPE: DNA
<213> ORGANISM: Artificial Sequence
<220> FEATURE:
<223> OTHER INFORMATION: Description of Artificial Sequence: Arg(AGG)
      5GFP
<220> FEATURE:
<221> NAME/KEY: CDS
<222> LOCATION: (1)..(732)

<400> SEQUENCE: 11 atg agg agg agg agg agg agc aag ggc gag gaa ctg ttc act ggc gtg      48
Met Arg Arg Arg Arg Arg Ser Lys Gly Glu Glu Leu Phe Thr Gly Val
  1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175
```

```
gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys
```

<210> SEQ ID NO 12
<211> LENGTH: 243
<212> TYPE: PRT
<213> ORGANISM: Artificial Sequence
<220> FEATURE:
<223> OTHER INFORMATION: Description of Artificial Sequence: Arg(AGG) 5GFP

<400> SEQUENCE: 12

```
Met Arg Arg Arg Arg Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

-continued

<210> SEQ ID NO 13
<211> LENGTH: 732
<212> TYPE: DNA
<213> ORGANISM: Artificial Sequence
<220> FEATURE:
<223> OTHER INFORMATION: Description of Artificial Sequence: Arg(CGA)
    5GFP
<220> FEATURE:
<221> NAME/KEY: CDS
<222> LOCATION: (1)..(732)

<400> SEQUENCE: 13

| | | | | | | | | | | | | | | | | |
|---|---|---|---|---|---|---|---|---|---|---|---|---|---|---|---|---|
| atg | cga | cga | cga | cga | cga | agc | aag | ggc | gag | gaa | ctg | ttc | act | ggc | gtg | 48 |
| Met | Arg | Arg | Arg | Arg | Arg | Ser | Lys | Gly | Glu | Glu | Leu | Phe | Thr | Gly | Val | |
| 1 | | | 5 | | | | | 10 | | | | | 15 | | | |
| gtc | cca | att | ctc | gtg | gaa | ctg | gat | ggc | gat | gtg | aat | ggg | cac | aaa | ttt | 96 |
| Val | Pro | Ile | Leu | Val | Glu | Leu | Asp | Gly | Asp | Val | Asn | Gly | His | Lys | Phe | |
| | | | 20 | | | | | 25 | | | | | 30 | | | |
| tct | gtc | agc | gga | gag | ggt | gaa | ggt | gat | gcc | aca | tac | gga | aag | ctc | acc | 144 |
| Ser | Val | Ser | Gly | Glu | Gly | Glu | Gly | Asp | Ala | Thr | Tyr | Gly | Lys | Leu | Thr | |
| | | 35 | | | | | 40 | | | | | 45 | | | | |
| ctg | aaa | ttc | atc | tgc | acc | act | gga | aag | ctc | cct | gtg | cca | tgg | cca | aca | 192 |
| Leu | Lys | Phe | Ile | Cys | Thr | Thr | Gly | Lys | Leu | Pro | Val | Pro | Trp | Pro | Thr | |
| 50 | | | | | 55 | | | | | 60 | | | | | | |
| ctg | gtc | act | acc | ttc | tct | tat | ggc | gtg | cag | tgc | ttt | tcc | aga | tac | cca | 240 |
| Leu | Val | Thr | Thr | Phe | Ser | Tyr | Gly | Val | Gln | Cys | Phe | Ser | Arg | Tyr | Pro | |
| 65 | | | | | 70 | | | | | 75 | | | | | 80 | |
| gac | cat | atg | aag | cag | cat | gac | ttt | ttc | aag | agc | gcc | atg | ccc | gag | ggc | 288 |
| Asp | His | Met | Lys | Gln | His | Asp | Phe | Phe | Lys | Ser | Ala | Met | Pro | Glu | Gly | |
| | | | | 85 | | | | | 90 | | | | | 95 | | |
| tat | gtg | cag | gag | aga | acc | atc | ttt | ttc | aaa | gat | gac | ggg | aac | tac | aag | 336 |
| Tyr | Val | Gln | Glu | Arg | Thr | Ile | Phe | Phe | Lys | Asp | Asp | Gly | Asn | Tyr | Lys | |
| | | | 100 | | | | | 105 | | | | | 110 | | | |
| acc | cgc | gct | gaa | gtc | aag | ttc | gaa | ggt | gac | acc | ctg | gtg | aat | aga | atc | 384 |
| Thr | Arg | Ala | Glu | Val | Lys | Phe | Glu | Gly | Asp | Thr | Leu | Val | Asn | Arg | Ile | |
| | | 115 | | | | | 120 | | | | | 125 | | | | |
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| 130 | | | | | 135 | | | | | 140 | | | | | | |
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | | 150 | | | | | 155 | | | | | 160 | |
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | | 180 | | | | | 185 | | | | | 190 | | | |
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |
| | | 195 | | | | | 200 | | | | | 205 | | | | |
| cag | tct | gcc | ctg | tct | aaa | gat | ccc | aac | gaa | aag | aga | gac | cac | atg | gtc | 672 |
| Gln | Ser | Ala | Leu | Ser | Lys | Asp | Pro | Asn | Glu | Lys | Arg | Asp | His | Met | Val | |
| 210 | | | | | 215 | | | | | 220 | | | | | | |
| ctg | ctg | gag | ttt | gtg | acc | gct | gct | ggg | atc | aca | cat | ggc | atg | gac | gag | 720 |
| Leu | Leu | Glu | Phe | Val | Thr | Ala | Ala | Gly | Ile | Thr | His | Gly | Met | Asp | Glu | |
| 225 | | | | | 230 | | | | | 235 | | | | | 240 | |
| ctg | tac | aag | tga | | | | | | | | | | | | | 732 |
| Leu | Tyr | Lys | | | | | | | | | | | | | | |

<210> SEQ ID NO 14
<211> LENGTH: 243

```
<212> TYPE: PRT
<213> ORGANISM: Artificial Sequence
<220> FEATURE:
<223> OTHER INFORMATION: Description of Artificial Sequence: Arg(CGA)
      5GFP

<400> SEQUENCE: 14

Met Arg Arg Arg Arg Ser Lys Gly Glu Glu Leu Phe Thr Gly Val
 1               5                  10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 15
<211> LENGTH: 732
<212> TYPE: DNA
<213> ORGANISM: Artificial Sequence
<220> FEATURE:
<223> OTHER INFORMATION: Description of Artificial Sequence: Arg(CGC)
      5GFP
<220> FEATURE:
<221> NAME/KEY: CDS
<222> LOCATION: (1)..(732)

<400> SEQUENCE: 15 atg cgc cgc cgc cgc cgc agc aag ggc gag gaa ctg ttc act ggc gtg    48
Met Arg Arg Arg Arg Arg Ser Lys Gly Glu Glu Leu Phe Thr Gly Val
 1               5                  10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
            20                  25                  30 tct gtc agc gga gag ggt gaa ggt gat gcc aca tac gga aag ctc acc   144
Ser Val Ser Gly Glu Gly Glu Gly Asp Ala Thr Tyr Gly Lys Leu Thr
```

```
                35                  40                  45
ctg aaa ttc atc tgc acc act gga aag ctc cct gtg cca tgg cca aca       192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc       624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc       672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag       720
Leu Leu Glu Phe Val Thr Ala Ala Gly Ile Thr His Gly Met Asp Glu
225                 230                 235                 240 ctg tac aag tga                                                       732
Leu Tyr Lys <210> SEQ ID NO 16
<211> LENGTH: 243
<212> TYPE: PRT
<213> ORGANISM: Artificial Sequence
<220> FEATURE:
<223> OTHER INFORMATION: Description of Artificial Sequence: Arg(CGC)
      5GFP

<400> SEQUENCE: 16

Met Arg Arg Arg Arg Ser Lys Gly Glu Glu Leu Phe Thr Gly Val
 1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80
```

```
Asp His Met Lys Gln His Asp Phe Phe Lys Ser Ala Met Pro Glu Gly
            85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
210                 215                 220

Leu Leu Glu Phe Val Thr Ala Ala Gly Ile Thr His Gly Met Asp Glu
225                 230                 235                 240

Leu Tyr Lys

<210> SEQ ID NO 17
<211> LENGTH: 732
<212> TYPE: DNA
<213> ORGANISM: Artificial Sequence
<220> FEATURE:
<223> OTHER INFORMATION: Description of Artificial Sequence: Arg(CGG)
      5GFP
<220> FEATURE:
<221> NAME/KEY: CDS
<222> LOCATION: (1)..(732)

<400> SEQUENCE: 17 atg cgg cgg cgg cgg cgg agc aag ggc gag gaa ctg ttc act ggc gtg      48
Met Arg Arg Arg Arg Arg Ser Lys Gly Glu Glu Leu Phe Thr Gly Val
1               5                   10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
                100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
            115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
```

-continued

```

Glu Leu Lys Gly Ile Asp Phe Lys Glu Asp Gly Asn Ile Leu Gly His
    130                 135                 140
aag ctg gaa tac aac tat aac tcc cac aat gtg tac atc atg gcc gac        480
Lys Leu Glu Tyr Asn Tyr Asn Ser His Asn Val Tyr Ile Met Ala Asp
145                 150                 155                 160
aag caa aag aat ggc atc aag gtc aac ttc aag atc aga cac aac att        528
Lys Gln Lys Asn Gly Ile Lys Val Asn Phe Lys Ile Arg His Asn Ile
                165                 170                 175
gag gat gga tcc gtg cag ctg gcc gac cat tat caa cag aac act cca        576
Glu Asp Gly Ser Val Gln Leu Ala Asp His Tyr Gln Gln Asn Thr Pro
            180                 185                 190
atc ggc gac ggc cct gtg ctc ctc cca gac aac cat tac ctg tcc acc        624
Ile Gly Asp Gly Pro Val Leu Leu Pro Asp Asn His Tyr Leu Ser Thr
        195                 200                 205
cag tct gcc ctg tct aaa gat ccc aac gaa aag aga gac cac atg gtc        672
Gln Ser Ala Leu Ser Lys Asp Pro Asn Glu Lys Arg Asp His Met Val
    210                 215                 220
ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240
ctg tac aag tga                                                        732
Leu Tyr Lys
```

```
<210> SEQ ID NO 18
<211> LENGTH: 243
<212> TYPE: PRT
<213> ORGANISM: Artificial Sequence
<220> FEATURE:
<223> OTHER INFORMATION: Description of Artificial Sequence: Arg(CGG)
      5GFP

<400> SEQUENCE: 18
```

```
Met Arg Arg Arg Arg Ser Lys Gly Glu Glu Leu Phe Thr Gly Val
  1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205
```

```
Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 19
<211> LENGTH: 732
<212> TYPE: DNA
<213> ORGANISM: Artificial Sequence
<220> FEATURE:
<223> OTHER INFORMATION: Description of Artificial Sequence: Arg(CGT)
      5GFP
<220> FEATURE:
<221> NAME/KEY: CDS
<222> LOCATION: (1)..(732)

<400> SEQUENCE: 19 atg cgt cgt cgt cgt cgt agc aag ggc gag gaa ctg ttc act ggc gtg       48
Met Arg Arg Arg Arg Arg Ser Lys Gly Glu Glu Leu Phe Thr Gly Val
  1               5                  10                  15 gtc cca att ctc gtg gaa ctg gat ggc gat gtg aat ggg cac aaa ttt       96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc      144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca      192
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220
```

```
      ctg ctg gag ttt gtg acc gct gct ggg atc aca cat ggc atg gac gag    720
      Leu Leu Glu Phe Val Thr Ala Ala Gly Ile Thr His Gly Met Asp Glu
      225                 230                 235                 240 ctg tac aag tga                                                    732
      Leu Tyr Lys <210> SEQ ID NO 20
<211> LENGTH: 243
<212> TYPE: PRT
<213> ORGANISM: Artificial Sequence
<220> FEATURE:
<223> OTHER INFORMATION: Description of Artificial Sequence: Arg(CGT)
      5GFP

<400> SEQUENCE: 20

Met Arg Arg Arg Arg Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 21
<211> LENGTH: 732
<212> TYPE: DNA
<213> ORGANISM: Artificial Sequence
<220> FEATURE:
<223> OTHER INFORMATION: Description of Artificial Sequence: Asn(AAC)
      5GFP
<220> FEATURE:
<221> NAME/KEY: CDS
<222> LOCATION: (1)..(732)

<400> SEQUENCE: 21
```

```
atg aac aac aac aac aac agc aag ggc gag gaa ctg ttc act ggc gtg         48
Met Asn Asn Asn Asn Asn Ser Lys Gly Glu Glu Leu Phe Thr Gly Val
 1               5                  10                  15 gtc cca att ctc gtg gaa ctg gat ggc gat gtg aat ggg cac aaa ttt         96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc        144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca        192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca        240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc        288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag        336
Tyr Val Gln Glu Arg Thr Ile Phe Phe Lys Asp Asp Gly Asn Tyr Lys
             100                 105                 110 acc cgc gct gaa gtc aag ttc gaa ggt gac acc ctg gtg aat aga atc        384
Thr Arg Ala Glu Val Lys Phe Glu Gly Asp Thr Leu Val Asn Arg Ile
         115                 120                 125 gag ctg aag ggc att gac ttt aag gag gat gga aac att ctc ggc cac        432
Glu Leu Lys Gly Ile Asp Phe Lys Glu Asp Gly Asn Ile Leu Gly His
 130                 135                 140 aag ctg gaa tac aac tat aac tcc cac aat gtg tac atc atg gcc gac        480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att        528
Lys Gln Lys Asn Gly Ile Lys Val Asn Phe Lys Ile Arg His Asn Ile
                 165                 170                 175 gag gat gga tcc gtg cag ctg gcc gac cat tat caa cag aac act cca        576
Glu Asp Gly Ser Val Gln Leu Ala Asp His Tyr Gln Gln Asn Thr Pro
             180                 185                 190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
         195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
 210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                        732
Leu Tyr Lys <210> SEQ ID NO 22
<211> LENGTH: 243
<212> TYPE: PRT
<213> ORGANISM: Artificial Sequence
<220> FEATURE:
<223> OTHER INFORMATION: Description of Artificial Sequence: Asn(AAC)
      5GFP

<400> SEQUENCE: 22

Met Asn Asn Asn Asn Asn Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30
```

-continued

```
Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
            130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys
```

<210> SEQ ID NO 23
<211> LENGTH: 732
<212> TYPE: DNA
<213> ORGANISM: Artificial Sequence
<220> FEATURE:
<223> OTHER INFORMATION: Description of Artificial Sequence: Asn(AAT) 5GFP
<220> FEATURE:
<221> NAME/KEY: CDS
<222> LOCATION: (1)..(732)

<400> SEQUENCE: 23

```
atg aat aat aat aat aat agc aag ggc gag gaa ctg ttc act ggc gtg     48
Met Asn Asn Asn Asn Asn Ser Lys Gly Glu Glu Leu Phe Thr Gly Val
  1               5                  10                  15 gtc cca att ctc gtg gaa ctg gat ggc gat gtg aat ggg cac aaa ttt     96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                 85                  90                  95
```

-continued

```
tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
        100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
    115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
            165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
        180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
    195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 24
<211> LENGTH: 243
<212> TYPE: PRT
<213> ORGANISM: Artificial Sequence
<220> FEATURE:
<223> OTHER INFORMATION: Description of Artificial Sequence: Asn(AAT) 5GFP

<400> SEQUENCE: 24

```
Met Asn Asn Asn Asn Ser Lys Gly Glu Glu Leu Phe Thr Gly Val
1               5                   10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
```

-continued

```
            145                 150                 155                 160
Lys Gln Lys Asn Gly Ile Lys Val Asn Phe Lys Ile Arg His Asn Ile
                165                 170                 175
Glu Asp Gly Ser Val Gln Leu Ala Asp His Tyr Gln Gln Asn Thr Pro
            180                 185                 190
Ile Gly Asp Gly Pro Val Leu Leu Pro Asp Asn His Tyr Leu Ser Thr
        195                 200                 205
Gln Ser Ala Leu Ser Lys Asp Pro Asn Glu Lys Arg Asp His Met Val
    210                 215                 220
Leu Leu Glu Phe Val Thr Ala Ala Gly Ile Thr His Gly Met Asp Glu
225                 230                 235                 240
Leu Tyr Lys

<210> SEQ ID NO 25
<211> LENGTH: 732
<212> TYPE: DNA
<213> ORGANISM: Artificial Sequence
<220> FEATURE:
<223> OTHER INFORMATION: Description of Artificial Sequence: Asp(GAC)
      5GFP
<220> FEATURE:
<221> NAME/KEY: CDS
<222> LOCATION: (1)..(732)

<400> SEQUENCE: 25 atg gac gac gac gac gac agc aag ggc gag gaa ctg ttc act ggc gtg       48
Met Asp Asp Asp Asp Asp Ser Lys Gly Glu Glu Leu Phe Thr Gly Val
 1               5                  10                  15 gtc cca att ctc gtg gaa ctg gat ggc gat gtg aat ggg cac aaa ttt       96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc      144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca      192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
                100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
            115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
        130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
```

-continued

```
              180                 185                 190
atc ggc gac ggc cct gtg ctc ctc cca gac aac cat tac ctg tcc acc        624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                        732
Leu Tyr Lys
```

<210> SEQ ID NO 26
<211> LENGTH: 243
<212> TYPE: PRT
<213> ORGANISM: Artificial Sequence
<220> FEATURE:
<223> OTHER INFORMATION: Description of Artificial Sequence: Asp(GAC) 5GFP

<400> SEQUENCE: 26

```
Met Asp Asp Asp Asp Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 27
<211> LENGTH: 732
<212> TYPE: DNA

```
<213> ORGANISM: Artificial Sequence
<220> FEATURE:
<223> OTHER INFORMATION: Description of Artificial Sequence: Asp(GAT)
      5GFP
<220> FEATURE:
<221> NAME/KEY: CDS
<222> LOCATION: (1)..(732)

<400> SEQUENCE: 27 atg gat gat gat gat gat agc aag ggc gag gaa ctg ttc act ggc gtg       48
Met Asp Asp Asp Asp Asp Ser Lys Gly Glu Glu Leu Phe Thr Gly Val
 1               5                  10                  15 gtc cca att ctc gtg gaa ctg gat ggc gat gtg aat ggg cac aaa ttt       96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc      144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca      192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 28
<211> LENGTH: 243
<212> TYPE: PRT
<213> ORGANISM: Artificial Sequence
<220> FEATURE:
```

-continued

<223> OTHER INFORMATION: Description of Artificial Sequence: Asp(GAT)
     5GFP

<400> SEQUENCE: 28

Met Asp Asp Asp Asp Ser Lys Gly Glu Glu Leu Phe Thr Gly Val
1               5                   10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
210                 215                 220

Leu Leu Glu Phe Val Thr Ala Ala Gly Ile Thr His Gly Met Asp Glu
225                 230                 235                 240

Leu Tyr Lys

<210> SEQ ID NO 29
<211> LENGTH: 732
<212> TYPE: DNA
<213> ORGANISM: Artificial Sequence
<220> FEATURE:
<223> OTHER INFORMATION: Description of Artificial Sequence: Cys(TGC)
     5GFP
<220> FEATURE:
<221> NAME/KEY: CDS
<222> LOCATION: (1)..(732)

<400> SEQUENCE: 29 atg tgc tgc tgc tgc agc aag ggc gag gaa ctg ttc act ggc gtg        48
Met Cys Cys Cys Cys Ser Lys Gly Glu Glu Leu Phe Thr Gly Val
1               5                   10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
            20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
        35                  40                  45 ctg aaa ttc atc tgc acc act gga aag ctc cct gtg cca tgg cca aca    192

```
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca         240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc         288
Asp His Met Lys Gln His Asp Phe Phe Lys Ser Ala Met Pro Glu Gly
                     85                  90                  95 tat gtg cag gag aga acc atc ttt ttc aaa gat gac ggg aac tac aag         336
Tyr Val Gln Glu Arg Thr Ile Phe Phe Lys Asp Asp Gly Asn Tyr Lys
                100                 105                 110 acc cgc gct gaa gtc aag ttc gaa ggt gac acc ctg gtg aat aga atc         384
Thr Arg Ala Glu Val Lys Phe Glu Gly Asp Thr Leu Val Asn Arg Ile
            115                 120                 125 gag ctg aag ggc att gac ttt aag gag gat gga aac att ctc ggc cac         432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac         480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att         528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca         576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc         624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc         672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag         720
Leu Leu Glu Phe Val Thr Ala Ala Gly Ile Thr His Gly Met Asp Glu
225                 230                 235                 240 ctg tac aag tga                                                         732
Leu Tyr Lys <210> SEQ ID NO 30
<211> LENGTH: 243
<212> TYPE: PRT
<213> ORGANISM: Artificial Sequence
<220> FEATURE:
<223> OTHER INFORMATION: Description of Artificial Sequence: Cys(TGC)
      5GFP

<400> SEQUENCE: 30

Met Cys Cys Cys Cys Ser Lys Gly Glu Glu Leu Phe Thr Gly Val
 1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                     85                  90                  95
```

```
Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 31
<211> LENGTH: 732
<212> TYPE: DNA
<213> ORGANISM: Artificial Sequence
<220> FEATURE:
<223> OTHER INFORMATION: Description of Artificial Sequence: Cys(TGT)
      5GFP
<220> FEATURE:
<221> NAME/KEY: CDS
<222> LOCATION: (1)..(732)

<400> SEQUENCE: 31 atg tgt tgt tgt tgt tgt agc aag ggc gag gaa ctg ttc act ggc gtg        48
Met Cys Cys Cys Cys Cys Ser Lys Gly Glu Glu Leu Phe Thr Gly Val
 1               5                  10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
    130                 135                 140
```

```
aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 32
<211> LENGTH: 243
<212> TYPE: PRT
<213> ORGANISM: Artificial Sequence
<220> FEATURE:
<223> OTHER INFORMATION: Description of Artificial Sequence: Cys(TGT) 5GFP

<400> SEQUENCE: 32

```
Met Cys Cys Cys Cys Ser Lys Gly Glu Glu Leu Phe Thr Gly Val
1               5                   10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220
```

```
Leu Leu Glu Phe Val Thr Ala Ala Gly Ile Thr His Gly Met Asp Glu
225                 230                 235                 240

Leu Tyr Lys

<210> SEQ ID NO 33
<211> LENGTH: 732
<212> TYPE: DNA
<213> ORGANISM: Artificial Sequence
<220> FEATURE:
<223> OTHER INFORMATION: Description of Artificial Sequence: Gln(CAA)
      5GFP
<220> FEATURE:
<221> NAME/KEY: CDS
<222> LOCATION: (1)..(732)

<400> SEQUENCE: 33 atg caa caa caa caa caa agc aag ggc gag gaa ctg ttc act ggc gtg     48
Met Gln Gln Gln Gln Gln Ser Lys Gly Glu Glu Leu Phe Thr Gly Val
 1               5                  10                  15 gtc cca att ctc gtg gaa ctg gat ggc gat gtg aat ggg cac aaa ttt     96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240
```

```
ctg tac aag tga                                                      732
Leu Tyr Lys <210> SEQ ID NO 34
<211> LENGTH: 243
<212> TYPE: PRT
<213> ORGANISM: Artificial Sequence
<220> FEATURE:
<223> OTHER INFORMATION: Description of Artificial Sequence: Gln(CAA)
      5GFP

<400> SEQUENCE: 34

Met Gln Gln Gln Gln Gln Ser Lys Gly Glu Glu Leu Phe Thr Gly Val
  1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 35
<211> LENGTH: 732
<212> TYPE: DNA
<213> ORGANISM: Artificial Sequence
<220> FEATURE:
<223> OTHER INFORMATION: Description of Artificial Sequence: Gln(CAG)
      5GFP
<220> FEATURE:
<221> NAME/KEY: CDS
<222> LOCATION: (1)..(732)

<400> SEQUENCE: 35 atg cag cag cag cag cag agc aag ggc gag gaa ctg ttc act ggc gtg    48
Met Gln Gln Gln Gln Gln Ser Lys Gly Glu Glu Leu Phe Thr Gly Val
  1               5                  10                  15
```

```
gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys
```

<210> SEQ ID NO 36
<211> LENGTH: 243
<212> TYPE: PRT
<213> ORGANISM: Artificial Sequence
<220> FEATURE:
<223> OTHER INFORMATION: Description of Artificial Sequence: Gln(CAG)
      5GFP

<400> SEQUENCE: 36

```
Met Gln Gln Gln Gln Gln Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45
```

```
Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
210                 215                 220

Leu Leu Glu Phe Val Thr Ala Ala Gly Ile Thr His Gly Met Asp Glu
225                 230                 235                 240

Leu Tyr Lys

<210> SEQ ID NO 37
<211> LENGTH: 732
<212> TYPE: DNA
<213> ORGANISM: Artificial Sequence
<220> FEATURE:
<223> OTHER INFORMATION: Description of Artificial Sequence: Glu(GAA)
      5GFP
<220> FEATURE:
<221> NAME/KEY: CDS
<222> LOCATION: (1)..(732)

<400> SEQUENCE: 37 atg gaa gaa gaa gaa gaa agc aag ggc gag gaa ctg ttc act ggc gtg     48
Met Glu Glu Glu Glu Glu Ser Lys Gly Glu Glu Leu Phe Thr Gly Val
 1               5                  10                  15 gtc cca att ctc gtg gaa ctg gat ggc gat gtg aat ggg cac aaa ttt     96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
```

```
acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 38
<211> LENGTH: 243
<212> TYPE: PRT
<213> ORGANISM: Artificial Sequence
<220> FEATURE:
<223> OTHER INFORMATION: Description of Artificial Sequence: Glu(GAA) 5GFP

<400> SEQUENCE: 38

```
Met Glu Glu Glu Glu Ser Lys Gly Glu Glu Leu Phe Thr Gly Val
 1               5                  10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
```

```
                    165                 170                 175
Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 39
<211> LENGTH: 732
<212> TYPE: DNA
<213> ORGANISM: Artificial Sequence
<220> FEATURE:
<223> OTHER INFORMATION: Description of Artificial Sequence: Glu(GAG)
      5GFP
<220> FEATURE:
<221> NAME/KEY: CDS
<222> LOCATION: (1)..(732)

<400> SEQUENCE: 39 atg gag gag gag gag gag agc aag ggc gag gaa ctg ttc act ggc gtg      48
Met Glu Glu Glu Glu Glu Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
```

```
                                                         -continued

Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                        732
Leu Tyr Lys <210> SEQ ID NO 40
<211> LENGTH: 243
<212> TYPE: PRT
<213> ORGANISM: Artificial Sequence
<220> FEATURE:
<223> OTHER INFORMATION: Description of Artificial Sequence: Glu(GAG)
      5GFP

<400> SEQUENCE: 40

Met Glu Glu Glu Glu Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
                180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 41
<211> LENGTH: 732
<212> TYPE: DNA
<213> ORGANISM: Artificial Sequence
<220> FEATURE:
<223> OTHER INFORMATION: Description of Artificial Sequence: Gly(GGA)
```

```
        5GFP
<220> FEATURE:
<221> NAME/KEY: CDS
<222> LOCATION: (1)..(732)

<400> SEQUENCE: 41 atg gga gga gga gga gga agc aag ggc gag gaa ctg ttc act ggc gtg        48
Met Gly Gly Gly Gly Gly Ser Lys Gly Glu Glu Leu Phe Thr Gly Val
1               5                   10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc       624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc       672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag       720
Leu Leu Glu Phe Val Thr Ala Ala Gly Ile Thr His Gly Met Asp Glu
225                 230                 235                 240 ctg tac aag tga                                                       732
Leu Tyr Lys <210> SEQ ID NO 42
<211> LENGTH: 243
<212> TYPE: PRT
<213> ORGANISM: Artificial Sequence
<220> FEATURE:
<223> OTHER INFORMATION: Description of Artificial Sequence: Gly(GGA)
      5GFP
```

<400> SEQUENCE: 42

```
Met Gly Gly Gly Gly Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
             100                 105                 110

Thr Arg Ala Glu Val Lys Phe Glu Gly Asp Thr Leu Val Asn Arg Ile
         115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                 165                 170                 175

Glu Asp Gly Ser Val Gln Leu Ala Asp His Tyr Gln Gln Asn Thr Pro
             180                 185                 190

Ile Gly Asp Gly Pro Val Leu Leu Pro Asp Asn His Tyr Leu Ser Thr
         195                 200                 205

Gln Ser Ala Leu Ser Lys Asp Pro Asn Glu Lys Arg Asp His Met Val
     210                 215                 220

Leu Leu Glu Phe Val Thr Ala Ala Gly Ile Thr His Gly Met Asp Glu
225                 230                 235                 240

Leu Tyr Lys
```

<210> SEQ ID NO 43
<211> LENGTH: 732
<212> TYPE: DNA
<213> ORGANISM: Artificial Sequence
<220> FEATURE:
<223> OTHER INFORMATION: Description of Artificial Sequence: Gly(GGC) 5GFP
<220> FEATURE:
<221> NAME/KEY: CDS
<222> LOCATION: (1)..(732)

<400> SEQUENCE: 43

```
atg ggc ggc ggc ggc agc aag ggc gag gaa ctg ttc act ggc gtg        48
Met Gly Gly Gly Gly Ser Lys Gly Glu Glu Leu Phe Thr Gly Val
 1               5                  10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc   144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca   192
Leu Lys Phe Ile Cys Thr Thr Gly Lys Leu Pro Val Pro Trp Pro Thr
 50                  55                  60
```

```
ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc       624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc       672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag       720
Leu Leu Glu Phe Val Thr Ala Ala Gly Ile Thr His Gly Met Asp Glu
225                 230                 235                 240 ctg tac aag tga                                                       732
Leu Tyr Lys <210> SEQ ID NO 44
<211> LENGTH: 243
<212> TYPE: PRT
<213> ORGANISM: Artificial Sequence
<220> FEATURE:
<223> OTHER INFORMATION: Description of Artificial Sequence: Gly(GGC)
      5GFP

<400> SEQUENCE: 44

Met Gly Gly Gly Gly Ser Lys Gly Glu Glu Leu Phe Thr Gly Val
 1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110
```

```
Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 45
<211> LENGTH: 732
<212> TYPE: DNA
<213> ORGANISM: Artificial Sequence
<220> FEATURE:
<223> OTHER INFORMATION: Description of Artificial Sequence: Gly(GGG)
      5GFP
<220> FEATURE:
<221> NAME/KEY: CDS
<222> LOCATION: (1)..(732)

<400> SEQUENCE: 45 atg ggg ggg ggg ggg ggg agc aag ggc gag gaa ctg ttc act ggc gtg      48
Met Gly Gly Gly Gly Gly Ser Lys Gly Glu Glu Leu Phe Thr Gly Val
1               5                   10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160
```

```
aag caa aag aat ggc atc aag gtc aac ttc aag atc aga cac aac att    528
Lys Gln Lys Asn Gly Ile Lys Val Asn Phe Lys Ile Arg His Asn Ile
            165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
        180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
    195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys <210> SEQ ID NO 46
<211> LENGTH: 243
<212> TYPE: PRT
<213> ORGANISM: Artificial Sequence
<220> FEATURE:
<223> OTHER INFORMATION: Description of Artificial Sequence: Gly(GGG)
      5GFP

<400> SEQUENCE: 46

Met Gly Gly Gly Gly Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240
```

Leu Tyr Lys

<210> SEQ ID NO 47
<211> LENGTH: 732
<212> TYPE: DNA
<213> ORGANISM: Artificial Sequence
<220> FEATURE:
<223> OTHER INFORMATION: Description of Artificial Sequence: Gly(GGT) 5GFP
<220> FEATURE:
<221> NAME/KEY: CDS
<222> LOCATION: (1)..(732)

<400> SEQUENCE: 47

| | | | | | | | | | | | | | | | | |
|---|---|---|---|---|---|---|---|---|---|---|---|---|---|---|---|---|
| atg | ggt | ggt | ggt | ggt | ggt | agc | aag | ggc | gag | gaa | ctg | ttc | act | ggc | gtg | 48 |
| Met | Gly | Gly | Gly | Gly | Gly | Ser | Lys | Gly | Glu | Glu | Leu | Phe | Thr | Gly | Val | |
| 1 | | | | 5 | | | | | 10 | | | | | 15 | | |
| gtc | cca | att | ctc | gtg | gaa | ctg | gat | ggc | gat | gtg | aat | ggg | cac | aaa | ttt | 96 |
| Val | Pro | Ile | Leu | Val | Glu | Leu | Asp | Gly | Asp | Val | Asn | Gly | His | Lys | Phe | |
| | | | 20 | | | | | 25 | | | | | 30 | | | |
| tct | gtc | agc | gga | gag | ggt | gaa | ggt | gat | gcc | aca | tac | gga | aag | ctc | acc | 144 |
| Ser | Val | Ser | Gly | Glu | Gly | Glu | Gly | Asp | Ala | Thr | Tyr | Gly | Lys | Leu | Thr | |
| | | 35 | | | | | 40 | | | | | 45 | | | | |
| ctg | aaa | ttc | atc | tgc | acc | act | gga | aag | ctc | cct | gtg | cca | tgg | cca | aca | 192 |
| Leu | Lys | Phe | Ile | Cys | Thr | Thr | Gly | Lys | Leu | Pro | Val | Pro | Trp | Pro | Thr | |
| | 50 | | | | | 55 | | | | | 60 | | | | | |
| ctg | gtc | act | acc | ttc | tct | tat | ggc | gtg | cag | tgc | ttt | tcc | aga | tac | cca | 240 |
| Leu | Val | Thr | Thr | Phe | Ser | Tyr | Gly | Val | Gln | Cys | Phe | Ser | Arg | Tyr | Pro | |
| 65 | | | | | 70 | | | | | 75 | | | | | 80 | |
| gac | cat | atg | aag | cag | cat | gac | ttt | ttc | aag | agc | gcc | atg | ccc | gag | ggc | 288 |
| Asp | His | Met | Lys | Gln | His | Asp | Phe | Phe | Lys | Ser | Ala | Met | Pro | Glu | Gly | |
| | | | | 85 | | | | | 90 | | | | | 95 | | |
| tat | gtg | cag | gag | aga | acc | atc | ttt | ttc | aaa | gat | gac | ggg | aac | tac | aag | 336 |
| Tyr | Val | Gln | Glu | Arg | Thr | Ile | Phe | Phe | Lys | Asp | Asp | Gly | Asn | Tyr | Lys | |
| | | | 100 | | | | | 105 | | | | | 110 | | | |
| acc | cgc | gct | gaa | gtc | aag | ttc | gaa | ggt | gac | acc | ctg | gtg | aat | aga | atc | 384 |
| Thr | Arg | Ala | Glu | Val | Lys | Phe | Glu | Gly | Asp | Thr | Leu | Val | Asn | Arg | Ile | |
| | | 115 | | | | | 120 | | | | | 125 | | | | |
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| | 130 | | | | | 135 | | | | | 140 | | | | | |
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | | 150 | | | | | 155 | | | | | 160 | |
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | | 180 | | | | | 185 | | | | | 190 | | | |
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |
| | | 195 | | | | | 200 | | | | | 205 | | | | |
| cag | tct | gcc | ctg | tct | aaa | gat | ccc | aac | gaa | aag | aga | gac | cac | atg | gtc | 672 |
| Gln | Ser | Ala | Leu | Ser | Lys | Asp | Pro | Asn | Glu | Lys | Arg | Asp | His | Met | Val | |
| | 210 | | | | | 215 | | | | | 220 | | | | | |
| ctg | ctg | gag | ttt | gtg | acc | gct | gct | ggg | atc | aca | cat | ggc | atg | gac | gag | 720 |
| Leu | Leu | Glu | Phe | Val | Thr | Ala | Ala | Gly | Ile | Thr | His | Gly | Met | Asp | Glu | |
| 225 | | | | | 230 | | | | | 235 | | | | | 240 | |
| ctg | tac | aag | tga | | | | | | | | | | | | | 732 |
| Leu | Tyr | Lys | | | | | | | | | | | | | | |

<210> SEQ ID NO 48
<211> LENGTH: 243
<212> TYPE: PRT
<213> ORGANISM: Artificial Sequence
<220> FEATURE:
<223> OTHER INFORMATION: Description of Artificial Sequence: Gly(GGT) 5GFP

<400> SEQUENCE: 48

```
Met Gly Gly Gly Gly Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 49
<211> LENGTH: 732
<212> TYPE: DNA
<213> ORGANISM: Artificial Sequence
<220> FEATURE:
<223> OTHER INFORMATION: Description of Artificial Sequence: His(CAC) 5GFP
<220> FEATURE:
<221> NAME/KEY: CDS
<222> LOCATION: (1)..(732)

<400> SEQUENCE: 49

```
atg cac cac cac cac cac agc aag ggc gag gaa ctg ttc act ggc gtg      48
Met His His His His His Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
```

```
                    20                  25                  30
tct gtc agc gga gag ggt gaa ggt gat gcc aca tac gga aag ctc acc      144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca      192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                       732
Leu Tyr Lys <210> SEQ ID NO 50
<211> LENGTH: 243
<212> TYPE: PRT
<213> ORGANISM: Artificial Sequence
<220> FEATURE:
<223> OTHER INFORMATION: Description of Artificial Sequence: His(CAC)
      5GFP

<400> SEQUENCE: 50

Met His His His His Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
 50                  55                  60
```

```
Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 51
<211> LENGTH: 732
<212> TYPE: DNA
<213> ORGANISM: Artificial Sequence
<220> FEATURE:
<223> OTHER INFORMATION: Description of Artificial Sequence: His(CAT)
      5GFP
<220> FEATURE:
<221> NAME/KEY: CDS
<222> LOCATION: (1)..(732)

<400> SEQUENCE: 51 atg cat cat cat cat cat agc aag ggc gag gaa ctg ttc act ggc gtg      48
Met His His His His His Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
```

-continued

```
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 52
<211> LENGTH: 243
<212> TYPE: PRT
<213> ORGANISM: Artificial Sequence
<220> FEATURE:
<223> OTHER INFORMATION: Description of Artificial Sequence: His(CAT)
      5GFP

<400> SEQUENCE: 52

Met His His His His Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
```

-continued

```
                    180                 185                 190
Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 53
<211> LENGTH: 732
<212> TYPE: DNA
<213> ORGANISM: Artificial Sequence
<220> FEATURE:
<223> OTHER INFORMATION: Description of Artificial Sequence: Ile(ATA)
      5GFP
<220> FEATURE:
<221> NAME/KEY: CDS
<222> LOCATION: (1)..(732)

<400> SEQUENCE: 53 atg ata ata ata ata ata agc aag ggc gag gaa ctg ttc act ggc gtg      48
Met Ile Ile Ile Ile Ile Ser Lys Gly Glu Glu Leu Phe Thr Gly Val
1               5                   10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
            20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
        35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
    50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205
```

```
cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 54
<211> LENGTH: 243
<212> TYPE: PRT
<213> ORGANISM: Artificial Sequence
<220> FEATURE:
<223> OTHER INFORMATION: Description of Artificial Sequence: Ile(ATA)
      5GFP

<400> SEQUENCE: 54

Met Ile Ile Ile Ile Ile Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 55
<211> LENGTH: 732
<212> TYPE: DNA
<213> ORGANISM: Artificial Sequence
<220> FEATURE:
<223> OTHER INFORMATION: Description of Artificial Sequence: Ile(ATC)
      5GFP
<220> FEATURE:
<221> NAME/KEY: CDS
```

<222> LOCATION: (1)..(732)

<400> SEQUENCE: 55

```
atg atc atc atc atc atc agc aag ggc gag gaa ctg ttc act ggc gtg        48
Met Ile Ile Ile Ile Ile Ser Lys Gly Glu Glu Leu Phe Thr Gly Val
 1               5                  10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc       624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc       672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag       720
Leu Leu Glu Phe Val Thr Ala Ala Gly Ile Thr His Gly Met Asp Glu
225                 230                 235                 240 ctg tac aag tga                                                       732
Leu Tyr Lys
```

<210> SEQ ID NO 56
<211> LENGTH: 243
<212> TYPE: PRT
<213> ORGANISM: Artificial Sequence
<220> FEATURE:
<223> OTHER INFORMATION: Description of Artificial Sequence: Ile(ATC) 5GFP

<400> SEQUENCE: 56

Met Ile Ile Ile Ile Ile Ser Lys Gly Glu Glu Leu Phe Thr Gly Val

```
                1               5              10              15
            Val Pro Ile Leu Val Glu Leu Asp Gly Asp Val Asn Gly His Lys Phe
                         20                  25                  30

Ser Val Ser Gly Glu Gly Glu Gly Asp Ala Thr Tyr Gly Lys Leu Thr
                         35                  40                  45

Leu Lys Phe Ile Cys Thr Thr Gly Lys Leu Pro Val Pro Trp Pro Thr
                         50                  55                  60

Leu Val Thr Thr Phe Ser Tyr Gly Val Gln Cys Phe Ser Arg Tyr Pro
             65                  70                  75                  80

Asp His Met Lys Gln His Asp Phe Phe Lys Ser Ala Met Pro Glu Gly
                             85                  90                  95

Tyr Val Gln Glu Arg Thr Ile Phe Phe Lys Asp Asp Gly Asn Tyr Lys
                            100                 105                 110

Thr Arg Ala Glu Val Lys Phe Glu Gly Asp Thr Leu Val Asn Arg Ile
                        115                 120                 125

Glu Leu Lys Gly Ile Asp Phe Lys Glu Asp Gly Asn Ile Leu Gly His
                        130                 135                 140

Lys Leu Glu Tyr Asn Tyr Asn Ser His Asn Val Tyr Ile Met Ala Asp
            145                 150                 155                 160

Lys Gln Lys Asn Gly Ile Lys Val Asn Phe Lys Ile Arg His Asn Ile
                            165                 170                 175

Glu Asp Gly Ser Val Gln Leu Ala Asp His Tyr Gln Gln Asn Thr Pro
                        180                 185                 190

Ile Gly Asp Gly Pro Val Leu Leu Pro Asp Asn His Tyr Leu Ser Thr
                        195                 200                 205

Gln Ser Ala Leu Ser Lys Asp Pro Asn Glu Lys Arg Asp His Met Val
                        210                 215                 220

Leu Leu Glu Phe Val Thr Ala Ala Gly Ile Thr His Gly Met Asp Glu
            225                 230                 235                 240

Leu Tyr Lys

<210> SEQ ID NO 57
<211> LENGTH: 732
<212> TYPE: DNA
<213> ORGANISM: Artificial Sequence
<220> FEATURE:
<223> OTHER INFORMATION: Description of Artificial Sequence: Ile(ATT)
      5GFP
<220> FEATURE:
<221> NAME/KEY: CDS
<222> LOCATION: (1)..(732)

<400> SEQUENCE: 57 atg att att att att att agc aag ggc gag gaa ctg ttc act ggc gtg     48
Met Ile Ile Ile Ile Ile Ser Lys Gly Glu Glu Leu Phe Thr Gly Val
  1               5                  10                  15 gtc cca att ctc gtg gaa ctg gat ggc gat gtg aat ggg cac aaa ttt     96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
 65                  70                  75                  80
```

```
gac cat atg aag cag cat gac ttt ttc aag agc gcc atg ccc gag ggc    288
Asp His Met Lys Gln His Asp Phe Phe Lys Ser Ala Met Pro Glu Gly
            85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
        100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
                115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys
```

```
<210> SEQ ID NO 58
<211> LENGTH: 243
<212> TYPE: PRT
<213> ORGANISM: Artificial Sequence
<220> FEATURE:
<223> OTHER INFORMATION: Description of Artificial Sequence: Ile(ATT)
      5GFP

<400> SEQUENCE: 58

Met Ile Ile Ile Ile Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125
```

```
Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 59
<211> LENGTH: 732
<212> TYPE: DNA
<213> ORGANISM: Artificial Sequence
<220> FEATURE:
<223> OTHER INFORMATION: Description of Artificial Sequence: Leu(CTA)
      5GFP
<220> FEATURE:
<221> NAME/KEY: CDS
<222> LOCATION: (1)..(732)

<400> SEQUENCE: 59
```

| | | | | | | | | | | | | | | | | |
|---|---|---|---|---|---|---|---|---|---|---|---|---|---|---|---|---|
| atg cta cta cta cta cta agc aag ggc gag gaa ctg ttc act ggc gtg | | | | | | | | | | | | | | | | 48 |
| Met Leu Leu Leu Leu Leu Ser Lys Gly Glu Glu Leu Phe Thr Gly Val | | | | | | | | | | | | | | | | |
| 1 5 10 15 | | | | | | | | | | | | | | | | |
| gtc cca att ctc gtg gaa ctg gat ggc gat gtg aat ggg cac aaa ttt | | | | | | | | | | | | | | | | 96 |
| Val Pro Ile Leu Val Glu Leu Asp Gly Asp Val Asn Gly His Lys Phe | | | | | | | | | | | | | | | | |
| 20 25 30 | | | | | | | | | | | | | | | | |
| tct gtc agc gga gag ggt gaa ggt gat gcc aca tac gga aag ctc acc | | | | | | | | | | | | | | | | 144 |
| Ser Val Ser Gly Glu Gly Glu Gly Asp Ala Thr Tyr Gly Lys Leu Thr | | | | | | | | | | | | | | | | |
| 35 40 45 | | | | | | | | | | | | | | | | |
| ctg aaa ttc atc tgc acc act gga aag ctc cct gtg cca tgg cca aca | | | | | | | | | | | | | | | | 192 |
| Leu Lys Phe Ile Cys Thr Thr Gly Lys Leu Pro Val Pro Trp Pro Thr | | | | | | | | | | | | | | | | |
| 50 55 60 | | | | | | | | | | | | | | | | |
| ctc gtc act acc ttc tct tat ggc gtg cag tgc ttt tcc aga tac cca | | | | | | | | | | | | | | | | 240 |
| Leu Val Thr Thr Phe Ser Tyr Gly Val Gln Cys Phe Ser Arg Tyr Pro | | | | | | | | | | | | | | | | |
| 65 70 75 80 | | | | | | | | | | | | | | | | |
| gac cat atg aag cag cat gac ttt ttc aag agc gcc atg ccc gag ggc | | | | | | | | | | | | | | | | 288 |
| Asp His Met Lys Gln His Asp Phe Phe Lys Ser Ala Met Pro Glu Gly | | | | | | | | | | | | | | | | |
| 85 90 95 | | | | | | | | | | | | | | | | |
| tat gtg cag gag aga acc atc ttt ttc aaa gat gac ggg aac tac aag | | | | | | | | | | | | | | | | 336 |
| Tyr Val Gln Glu Arg Thr Ile Phe Phe Lys Asp Asp Gly Asn Tyr Lys | | | | | | | | | | | | | | | | |
| 100 105 110 | | | | | | | | | | | | | | | | |
| acc cgc gct gaa gtc aag ttc gaa ggt gac acc ctg gtg aat aga atc | | | | | | | | | | | | | | | | 384 |
| Thr Arg Ala Glu Val Lys Phe Glu Gly Asp Thr Leu Val Asn Arg Ile | | | | | | | | | | | | | | | | |
| 115 120 125 | | | | | | | | | | | | | | | | |
| gag ctg aag ggc att gac ttt aag gag gat gga aac att ctc ggc cac | | | | | | | | | | | | | | | | 432 |
| Glu Leu Lys Gly Ile Asp Phe Lys Glu Asp Gly Asn Ile Leu Gly His | | | | | | | | | | | | | | | | |
| 130 135 140 | | | | | | | | | | | | | | | | |
| aag ctg gaa tac aac tat aac tcc cac aat gtg tac atc atg gcc gac | | | | | | | | | | | | | | | | 480 |
| Lys Leu Glu Tyr Asn Tyr Asn Ser His Asn Val Tyr Ile Met Ala Asp | | | | | | | | | | | | | | | | |
| 145 150 155 160 | | | | | | | | | | | | | | | | |
| aag caa aag aat ggc atc aag gtc aac ttc aag atc aga cac aac att | | | | | | | | | | | | | | | | 528 |
| Lys Gln Lys Asn Gly Ile Lys Val Asn Phe Lys Ile Arg His Asn Ile | | | | | | | | | | | | | | | | |

```
                      165                 170                 175
gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                     732
Leu Tyr Lys
```

<210> SEQ ID NO 60
<211> LENGTH: 243
<212> TYPE: PRT
<213> ORGANISM: Artificial Sequence
<220> FEATURE:
<223> OTHER INFORMATION: Description of Artificial Sequence: Leu(CTA)
      5GFP

<400> SEQUENCE: 60

```
Met Leu Leu Leu Leu Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 61
<211> LENGTH: 732
<212> TYPE: DNA
<213> ORGANISM: Artificial Sequence
<220> FEATURE:
<223> OTHER INFORMATION: Description of Artificial Sequence: Leu(CTC) 5GFP
<220> FEATURE:
<221> NAME/KEY: CDS
<222> LOCATION: (1)..(732)

<400> SEQUENCE: 61

| | | | | | | | | | | | | | | | | |
|---|---|---|---|---|---|---|---|---|---|---|---|---|---|---|---|---|
| atg | ctc | ctc | ctc | ctc | ctc | agc | aag | ggc | gag | gaa | ctg | ttc | act | ggc | gtg | 48 |
| Met | Leu | Leu | Leu | Leu | Leu | Ser | Lys | Gly | Glu | Glu | Leu | Phe | Thr | Gly | Val | |
| 1 | | | | 5 | | | | | 10 | | | | | 15 | | |
| gtc | cca | att | ctc | gtg | gaa | ctg | gat | ggc | gat | gtg | aat | ggg | cac | aaa | ttt | 96 |
| Val | Pro | Ile | Leu | Val | Glu | Leu | Asp | Gly | Asp | Val | Asn | Gly | His | Lys | Phe | |
| | | | 20 | | | | | 25 | | | | | 30 | | | |
| tct | gtc | agc | gga | gag | ggt | gaa | ggt | gat | gcc | aca | tac | gga | aag | ctc | acc | 144 |
| Ser | Val | Ser | Gly | Glu | Gly | Glu | Gly | Asp | Ala | Thr | Tyr | Gly | Lys | Leu | Thr | |
| | | 35 | | | | | 40 | | | | | 45 | | | | |
| ctg | aaa | ttc | atc | tgc | acc | act | gga | aag | ctc | cct | gtg | cca | tgg | cca | aca | 192 |
| Leu | Lys | Phe | Ile | Cys | Thr | Thr | Gly | Lys | Leu | Pro | Val | Pro | Trp | Pro | Thr | |
| | 50 | | | | | 55 | | | | | 60 | | | | | |
| ctg | gtc | act | acc | ttc | tct | tat | ggc | gtg | cag | tgc | ttt | tcc | aga | tac | cca | 240 |
| Leu | Val | Thr | Thr | Phe | Ser | Tyr | Gly | Val | Gln | Cys | Phe | Ser | Arg | Tyr | Pro | |
| 65 | | | | | 70 | | | | | 75 | | | | | 80 | |
| gac | cat | atg | aag | cag | cat | gac | ttt | ttc | aag | agc | gcc | atg | ccc | gag | ggc | 288 |
| Asp | His | Met | Lys | Gln | His | Asp | Phe | Phe | Lys | Ser | Ala | Met | Pro | Glu | Gly | |
| | | | | 85 | | | | | 90 | | | | | 95 | | |
| tat | gtg | cag | gag | aga | acc | atc | ttt | ttc | aaa | gat | gac | ggg | aac | tac | aag | 336 |
| Tyr | Val | Gln | Glu | Arg | Thr | Ile | Phe | Phe | Lys | Asp | Asp | Gly | Asn | Tyr | Lys | |
| | | | 100 | | | | | 105 | | | | | 110 | | | |
| acc | cgc | gct | gaa | gtc | aag | ttc | gaa | ggt | gac | acc | ctg | gtg | aat | aga | atc | 384 |
| Thr | Arg | Ala | Glu | Val | Lys | Phe | Glu | Gly | Asp | Thr | Leu | Val | Asn | Arg | Ile | |
| | | 115 | | | | | 120 | | | | | 125 | | | | |
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| | 130 | | | | | 135 | | | | | 140 | | | | | |
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | | 150 | | | | | 155 | | | | | 160 | |
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | | 180 | | | | | 185 | | | | | 190 | | | |
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |
| | | 195 | | | | | 200 | | | | | 205 | | | | |
| cag | tct | gcc | ctg | tct | aaa | gat | ccc | aac | gaa | aag | aga | gac | cac | atg | gtc | 672 |
| Gln | Ser | Ala | Leu | Ser | Lys | Asp | Pro | Asn | Glu | Lys | Arg | Asp | His | Met | Val | |
| | 210 | | | | | 215 | | | | | 220 | | | | | |
| ctg | ctg | gag | ttt | gtg | acc | gct | gct | ggg | atc | aca | cat | ggc | atg | gac | gag | 720 |
| Leu | Leu | Glu | Phe | Val | Thr | Ala | Ala | Gly | Ile | Thr | His | Gly | Met | Asp | Glu | |
| 225 | | | | | 230 | | | | | 235 | | | | | 240 | |
| ctg | tac | aag | tga | | | | | | | | | | | | | 732 |
| Leu | Tyr | Lys | | | | | | | | | | | | | | |

<210> SEQ ID NO 62

```
<211> LENGTH: 243
<212> TYPE: PRT
<213> ORGANISM: Artificial Sequence
<220> FEATURE:
<223> OTHER INFORMATION: Description of Artificial Sequence: Leu(CTC)
      5GFP

<400> SEQUENCE: 62

Met Leu Leu Leu Leu Leu Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 63
<211> LENGTH: 732
<212> TYPE: DNA
<213> ORGANISM: Artificial Sequence
<220> FEATURE:
<223> OTHER INFORMATION: Description of Artificial Sequence: Leu(CTG)
      5GFP
<220> FEATURE:
<221> NAME/KEY: CDS
<222> LOCATION: (1)..(732)

<400> SEQUENCE: 63 atg ctg ctg ctg ctg ctg agc aag ggc gag gaa ctg ttc act ggc gtg      48
Met Leu Leu Leu Leu Leu Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
```

| | | |
|---|---|---|
| ctg aaa ttc atc tgc acc act gga aag ctc cct gtg cca tgg cca aca<br>Leu Lys Phe Ile Cys Thr Thr Gly Lys Leu Pro Val Pro Trp Pro Thr<br>50                          55                      60 | | 192 |
| ctg gtc act acc ttc tct tat ggc gtg cag tgc ttt tcc aga tac cca<br>Leu Val Thr Thr Phe Ser Tyr Gly Val Gln Cys Phe Ser Arg Tyr Pro<br>65                            70                      75                  80 | | 240 |
| gac cat atg aag cag cat gac ttt ttc aag agc gcc atg ccc gag ggc<br>Asp His Met Lys Gln His Asp Phe Phe Lys Ser Ala Met Pro Glu Gly<br>                      85                      90                      95 | | 288 |
| tat gtg cag gag aga acc atc ttt ttc aaa gat gac ggg aac tac aag<br>Tyr Val Gln Glu Arg Thr Ile Phe Phe Lys Asp Asp Gly Asn Tyr Lys<br>                      100                    105                   110 | | 336 |
| acc cgc gct gaa gtc aag ttc gaa ggt gac acc ctg gtg aat aga atc<br>Thr Arg Ala Glu Val Lys Phe Glu Gly Asp Thr Leu Val Asn Arg Ile<br>            115                    120                    125 | | 384 |
| gag ctg aag ggc att gac ttt aag gag gat gga aac att ctc ggc cac<br>Glu Leu Lys Gly Ile Asp Phe Lys Glu Asp Gly Asn Ile Leu Gly His<br>130                     135                    140 | | 432 |
| aag ctg gaa tac aac tat aac tcc cac aat gtg tac atc atg gcc gac<br>Lys Leu Glu Tyr Asn Tyr Asn Ser His Asn Val Tyr Ile Met Ala Asp<br>145                    150                    155                   160 | | 480 |
| aag caa aag aat ggc atc aag gtc aac ttc aag atc aga cac aac att<br>Lys Gln Lys Asn Gly Ile Lys Val Asn Phe Lys Ile Arg His Asn Ile<br>                      165                    170                   175 | | 528 |
| gag gat gga tcc gtg cag ctg gcc gac cat tat caa cag aac act cca<br>Glu Asp Gly Ser Val Gln Leu Ala Asp His Tyr Gln Gln Asn Thr Pro<br>            180                    185                    190 | | 576 |
| atc ggc gac ggc cct gtg ctc ctc cca gac aac cat tac ctg tcc acc<br>Ile Gly Asp Gly Pro Val Leu Leu Pro Asp Asn His Tyr Leu Ser Thr<br>               195                    200                    205 | | 624 |
| cag tct gcc ctg tct aaa gat ccc aac gaa aag aga gac cac atg gtc<br>Gln Ser Ala Leu Ser Lys Asp Pro Asn Glu Lys Arg Asp His Met Val<br>210                     215                    220 | | 672 |
| ctg ctg gag ttt gtg acc gct gct ggg atc aca cat ggc atg gac gag<br>Leu Leu Glu Phe Val Thr Ala Ala Gly Ile Thr His Gly Met Asp Glu<br>225                    230                    235                   240 | | 720 |
| ctg tac aag tga<br>Leu Tyr Lys | | 732 |

<210> SEQ ID NO 64
<211> LENGTH: 243
<212> TYPE: PRT
<213> ORGANISM: Artificial Sequence
<220> FEATURE:
<223> OTHER INFORMATION: Description of Artificial Sequence: Leu(CTG)
    5GFP

<400> SEQUENCE: 64

Met Leu Leu Leu Leu Leu Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

```
Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 65
<211> LENGTH: 732
<212> TYPE: DNA
<213> ORGANISM: Artificial Sequence
<220> FEATURE:
<223> OTHER INFORMATION: Description of Artificial Sequence: Leu(CTT) 5GFP
<220> FEATURE:
<221> NAME/KEY: CDS
<222> LOCATION: (1)..(732)

<400> SEQUENCE: 65

```
atg ctt ctt ctt ctt ctt agc aag ggc gag gaa ctg ttc act ggc gtg      48
Met Leu Leu Leu Leu Leu Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                 70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125
```

```
gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
                195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 66
<211> LENGTH: 243
<212> TYPE: PRT
<213> ORGANISM: Artificial Sequence
<220> FEATURE:
<223> OTHER INFORMATION: Description of Artificial Sequence: Leu(CTT)
      5GFP

<400> SEQUENCE: 66

Met Leu Leu Leu Leu Ser Lys Gly Glu Glu Leu Phe Thr Gly Val
  1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
    65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
    145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
```

```
                195                 200                 205
Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 67
<211> LENGTH: 732
<212> TYPE: DNA
<213> ORGANISM: Artificial Sequence
<220> FEATURE:
<223> OTHER INFORMATION: Description of Artificial Sequence: Leu(TTA)
      5GFP
<220> FEATURE:
<221> NAME/KEY: CDS
<222> LOCATION: (1)..(732)

<400> SEQUENCE: 67 atg tta tta tta tta tta agc aag ggc gag gaa ctg ttc act ggc gtg     48
Met Leu Leu Leu Leu Leu Ser Lys Gly Glu Glu Leu Phe Thr Gly Val
  1               5                  10                  15 gtc cca att ctc gtg gaa ctg gat ggc gat gtg aat ggg cac aaa ttt     96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220
```

```
ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 68
<211> LENGTH: 243
<212> TYPE: PRT
<213> ORGANISM: Artificial Sequence
<220> FEATURE:
<223> OTHER INFORMATION: Description of Artificial Sequence: Leu(TTA) 5GFP

<400> SEQUENCE: 68

```
Met Leu Leu Leu Leu Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 69
<211> LENGTH: 732
<212> TYPE: DNA
<213> ORGANISM: Artificial Sequence
<220> FEATURE:
<223> OTHER INFORMATION: Description of Artificial Sequence: Leu(TTG) 5GFP
<220> FEATURE:
<221> NAME/KEY: CDS
<222> LOCATION: (1)..(732)

<400> SEQUENCE: 69

```
atg ttg ttg ttg ttg ttg agc aag ggc gag gaa ctg ttc act ggc gtg      48
Met Leu Leu Leu Leu Leu Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys
```

<210> SEQ ID NO 70
<211> LENGTH: 243
<212> TYPE: PRT
<213> ORGANISM: Artificial Sequence
<220> FEATURE:
<223> OTHER INFORMATION: Description of Artificial Sequence: Leu(TTG) 5GFP

<400> SEQUENCE: 70

```
Met Leu Leu Leu Leu Leu Ser Lys Gly Glu Glu Leu Phe Thr Gly Val
 1               5                  10                  15

Val Pro Ile Leu Val Glu Leu Asp Gly Asp Val Asn Gly His Lys Phe
```

```
                20                  25                  30
Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
             100                 105                 110

Thr Arg Ala Glu Val Lys Phe Glu Gly Asp Thr Leu Val Asn Arg Ile
         115                 120                 125

Glu Leu Lys Gly Ile Asp Phe Lys Glu Asp Gly Asn Ile Leu Gly His
     130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                 165                 170                 175

Glu Asp Gly Ser Val Gln Leu Ala Asp His Tyr Gln Gln Asn Thr Pro
             180                 185                 190

Ile Gly Asp Gly Pro Val Leu Leu Pro Asp Asn His Tyr Leu Ser Thr
         195                 200                 205

Gln Ser Ala Leu Ser Lys Asp Pro Asn Glu Lys Arg Asp His Met Val
     210                 215                 220

Leu Leu Glu Phe Val Thr Ala Ala Gly Ile Thr His Gly Met Asp Glu
225                 230                 235                 240

Leu Tyr Lys

<210> SEQ ID NO 71
<211> LENGTH: 732
<212> TYPE: DNA
<213> ORGANISM: Artificial Sequence
<220> FEATURE:
<223> OTHER INFORMATION: Description of Artificial Sequence: Lys(AAA)
      5GFP
<220> FEATURE:
<221> NAME/KEY: CDS
<222> LOCATION: (1)..(732)

<400> SEQUENCE: 71 atg aaa aaa aaa aaa aaa agc aag ggc gag gaa ctg ttc act ggc gtg      48
Met Lys Lys Lys Lys Lys Ser Lys Gly Glu Glu Leu Phe Thr Gly Val
  1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
```

-continued

```
                   85                  90                  95
tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys
```

<210> SEQ ID NO 72
<211> LENGTH: 243
<212> TYPE: PRT
<213> ORGANISM: Artificial Sequence
<220> FEATURE:
<223> OTHER INFORMATION: Description of Artificial Sequence: Lys(AAA) 5GFP

<400> SEQUENCE: 72

```
Met Lys Lys Lys Lys Ser Lys Gly Glu Glu Leu Phe Thr Gly Val
 1               5                  10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140
```

-continued

```
Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 73
<211> LENGTH: 732
<212> TYPE: DNA
<213> ORGANISM: Artificial Sequence
<220> FEATURE:
<223> OTHER INFORMATION: Description of Artificial Sequence: Lys(AAG) 5GFP
<220> FEATURE:
<221> NAME/KEY: CDS
<222> LOCATION: (1)..(732)

<400> SEQUENCE: 73

```
atg aag aag aag aag aag agc aag ggc gag gaa ctg ttc act ggc gtg     48
Met Lys Lys Lys Lys Lys Ser Lys Gly Glu Glu Leu Phe Thr Gly Val
1               5                   10                  15 gtc cca att ctc gtg gaa ctg gat ggc gat gtg aat ggg cac aaa ttt     96
Val Pro Ile Leu Val Glu Leu Asp Gly Asp Val Asn Gly His Lys Phe
            20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
        35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
    50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
```

```
                                                                               -continued Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                         732
Leu Tyr Lys
```

<210> SEQ ID NO 74
<211> LENGTH: 243
<212> TYPE: PRT
<213> ORGANISM: Artificial Sequence
<220> FEATURE:
<223> OTHER INFORMATION: Description of Artificial Sequence: Lys(AAG) 5GFP

<400> SEQUENCE: 74

```
Met Lys Lys Lys Lys Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
    65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 75
<211> LENGTH: 732

```
<212> TYPE: DNA
<213> ORGANISM: Artificial Sequence
<220> FEATURE:
<223> OTHER INFORMATION: Description of Artificial Sequence: Phe(TTT)
      5GFP
<220> FEATURE:
<221> NAME/KEY: CDS
<222> LOCATION: (1)..(732)

<400> SEQUENCE: 75 atg ttt ttt ttt ttt ttt agc aag ggc gag gaa ctg ttc act ggc gtg      48
Met Phe Phe Phe Phe Phe Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys <210> SEQ ID NO 76
<211> LENGTH: 243
<212> TYPE: PRT
<213> ORGANISM: Artificial Sequence
```

-continued

```
<220> FEATURE:
<223> OTHER INFORMATION: Description of Artificial Sequence: Phe(TTT)
      5GFP

<400> SEQUENCE: 76

Met Phe Phe Phe Phe Ser Lys Gly Glu Glu Leu Phe Thr Gly Val
1               5                  10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 77
<211> LENGTH: 732
<212> TYPE: DNA
<213> ORGANISM: Artificial Sequence
<220> FEATURE:
<223> OTHER INFORMATION: Description of Artificial Sequence: Phe(TTC)
      5GFP
<220> FEATURE:
<221> NAME/KEY: CDS
<222> LOCATION: (1)..(732)

<400> SEQUENCE: 77 atg ttc ttc ttc ttc ttc agc aag ggc gag gaa ctg ttc act ggc gtg      48
Met Phe Phe Phe Phe Phe Ser Lys Gly Glu Glu Leu Phe Thr Gly Val
1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
            20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
        35                  40                  45
```

| | | |
|---|---|---|
| ctg aaa ttc atc tgc acc act gga aag ctc cct gtg cca tgg cca aca<br>Leu Lys Phe Ile Cys Thr Thr Gly Lys Leu Pro Val Pro Trp Pro Thr<br>50 55 60 | 192 | |
| ctg gtc act acc ttc tct tat ggc gtg cag tgc ttt tcc aga tac cca<br>Leu Val Thr Thr Phe Ser Tyr Gly Val Gln Cys Phe Ser Arg Tyr Pro<br>65 70 75 80 | 240 | |
| gac cat atg aag cag cat gac ttt ttc aag agc gcc atg ccc gag ggc<br>Asp His Met Lys Gln His Asp Phe Phe Lys Ser Ala Met Pro Glu Gly<br>85 90 95 | 288 | |
| tat gtg cag gag aga acc atc ttt ttc aaa gat gac ggg aac tac aag<br>Tyr Val Gln Glu Arg Thr Ile Phe Phe Lys Asp Asp Gly Asn Tyr Lys<br>100 105 110 | 336 | |
| acc cgc gct gaa gtc aag ttc gaa ggt gac acc ctg gtg aat aga atc<br>Thr Arg Ala Glu Val Lys Phe Glu Gly Asp Thr Leu Val Asn Arg Ile<br>115 120 125 | 384 | |
| gag ctg aag ggc att gac ttt aag gag gat gga aac att ctc ggc cac<br>Glu Leu Lys Gly Ile Asp Phe Lys Glu Asp Gly Asn Ile Leu Gly His<br>130 135 140 | 432 | |
| aag ctg gaa tac aac tat aac tcc cac aat gtg tac atc atg gcc gac<br>Lys Leu Glu Tyr Asn Tyr Asn Ser His Asn Val Tyr Ile Met Ala Asp<br>145 150 155 160 | 480 | |
| aag caa aag aat ggc atc aag gtc aac ttc aag atc aga cac aac att<br>Lys Gln Lys Asn Gly Ile Lys Val Asn Phe Lys Ile Arg His Asn Ile<br>165 170 175 | 528 | |
| gag gat gga tcc gtg cag ctg gcc gac cat tat caa cag aac act cca<br>Glu Asp Gly Ser Val Gln Leu Ala Asp His Tyr Gln Gln Asn Thr Pro<br>180 185 190 | 576 | |
| atc ggc gac ggc cct gtg ctc ctc cca gac aac cat tac ctg tcc acc<br>Ile Gly Asp Gly Pro Val Leu Leu Pro Asp Asn His Tyr Leu Ser Thr<br>195 200 205 | 624 | |
| cag tct gcc ctg tct aaa gat ccc aac gaa aag aga gac cac atg gtc<br>Gln Ser Ala Leu Ser Lys Asp Pro Asn Glu Lys Arg Asp His Met Val<br>210 215 220 | 672 | |
| ctg ctg gag ttt gtg acc gct gct ggg atc aca cat ggc atg gac gag<br>Leu Leu Glu Phe Val Thr Ala Ala Gly Ile Thr His Gly Met Asp Glu<br>225 230 235 240 | 720 | |
| ctg tac aag tga<br>Leu Tyr Lys | 732 | |

<210> SEQ ID NO 78
<211> LENGTH: 243
<212> TYPE: PRT
<213> ORGANISM: Artificial Sequence
<220> FEATURE:
<223> OTHER INFORMATION: Description of Artificial Sequence: Phe(TTC)
    5GFP

<400> SEQUENCE: 78

Met Phe Phe Phe Phe Phe Ser Lys Gly Glu Glu Leu Phe Thr Gly Val
1               5                   10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

```
Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 79
<211> LENGTH: 732
<212> TYPE: DNA
<213> ORGANISM: Artificial Sequence
<220> FEATURE:
<223> OTHER INFORMATION: Description of Artificial Sequence: Pro(CCC)
      5GFP
<220> FEATURE:
<221> NAME/KEY: CDS
<222> LOCATION: (1)..(732)

<400> SEQUENCE: 79 atg ccc ccc ccc ccc ccc agc aag ggc gag gaa ctg ttc act ggc gtg    48
Met Pro Pro Pro Pro Pro Ser Lys Gly Glu Glu Leu Phe Thr Gly Val
1               5                   10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
            20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
        35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
    50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
    130                 135                 140
```

```
aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 80
<211> LENGTH: 243
<212> TYPE: PRT
<213> ORGANISM: Artificial Sequence
<220> FEATURE:
<223> OTHER INFORMATION: Description of Artificial Sequence: Pro(CCC)
      5GFP

<400> SEQUENCE: 80

Met Pro Pro Pro Pro Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
```

```
              210                 215                 220
Leu Leu Glu Phe Val Thr Ala Ala Gly Ile Thr His Gly Met Asp Glu
225                 230                 235                 240

Leu Tyr Lys

<210> SEQ ID NO 81
<211> LENGTH: 732
<212> TYPE: DNA
<213> ORGANISM: Artificial Sequence
<220> FEATURE:
<223> OTHER INFORMATION: Description of Artificial Sequence: Pro(CCG)
      5GFP
<220> FEATURE:
<221> NAME/KEY: CDS
<222> LOCATION: (1)..(732)

<400> SEQUENCE: 81 atg ccg ccg ccg ccg ccg agc aag ggc gag gaa ctg ttc act ggc gtg         48
Met Pro Pro Pro Pro Pro Ser Lys Gly Glu Glu Leu Phe Thr Gly Val
1               5                   10                  15 gtc cca att ctc gtg gaa ctg gat ggc gat gtg aat ggg cac aaa ttt         96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc        144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca        192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca        240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc        288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag        336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc        384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac        432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac        480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att        528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca        576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
```

```
                  225                 230                 235                 240 ctg tac aag tga                                                                         732
Leu Tyr Lys <210> SEQ ID NO 82
<211> LENGTH: 243
<212> TYPE: PRT
<213> ORGANISM: Artificial Sequence
<220> FEATURE:
<223> OTHER INFORMATION: Description of Artificial Sequence: Pro(CCG)
      5GFP

<400> SEQUENCE: 82

Met Pro Pro Pro Pro Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 83
<211> LENGTH: 732
<212> TYPE: DNA
<213> ORGANISM: Artificial Sequence
<220> FEATURE:
<223> OTHER INFORMATION: Description of Artificial Sequence: Pro(CCT)
      5GFP
<220> FEATURE:
<221> NAME/KEY: CDS
<222> LOCATION: (1)..(732)

<400> SEQUENCE: 83 atg cct cct cct cct cct agc aag ggc gag gaa ctg ttc act ggc gtg        48
Met Pro Pro Pro Pro Pro Ser Lys Gly Glu Glu Leu Phe Thr Gly Val
```

```
         1               5                   10                  15
gtc cca att ctc gtg gaa ctg gat ggc gat gtg aat ggg cac aaa ttt    96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc   144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca   192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca   240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc   288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag   336
Tyr Val Gln Glu Arg Thr Ile Phe Phe Lys Asp Asp Gly Asn Tyr Lys
             100                 105                 110 acc cgc gct gaa gtc aag ttc gaa ggt gac acc ctg gtg aat aga atc   384
Thr Arg Ala Glu Val Lys Phe Glu Gly Asp Thr Leu Val Asn Arg Ile
         115                 120                 125 gag ctg aag ggc att gac ttt aag gag gat gga aac att ctc ggc cac   432
Glu Leu Lys Gly Ile Asp Phe Lys Glu Asp Gly Asn Ile Leu Gly His
     130                 135                 140 aag ctg gaa tac aac tat aac tcc cac aat gtg tac atc atg gcc gac   480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att   528
Lys Gln Lys Asn Gly Ile Lys Val Asn Phe Lys Ile Arg His Asn Ile
                 165                 170                 175 gag gat gga tcc gtg cag ctg gcc gac cat tat caa cag aac act cca   576
Glu Asp Gly Ser Val Gln Leu Ala Asp His Tyr Gln Gln Asn Thr Pro
             180                 185                 190 atc ggc gac ggc cct gtg ctc ctc cca gac aac cat tac ctg tcc acc   624
Ile Gly Asp Gly Pro Val Leu Leu Pro Asp Asn His Tyr Leu Ser Thr
         195                 200                 205 cag tct gcc ctg tct aaa gat ccc aac gaa aag aga gac cac atg gtc   672
Gln Ser Ala Leu Ser Lys Asp Pro Asn Glu Lys Arg Asp His Met Val
     210                 215                 220 ctg ctg gag ttt gtg acc gct gct ggg atc aca cat ggc atg gac gag   720
Leu Leu Glu Phe Val Thr Ala Ala Gly Ile Thr His Gly Met Asp Glu
225                 230                 235                 240 ctg tac aag tga                                                   732
Leu Tyr Lys <210> SEQ ID NO 84
<211> LENGTH: 243
<212> TYPE: PRT
<213> ORGANISM: Artificial Sequence
<220> FEATURE:
<223> OTHER INFORMATION: Description of Artificial Sequence: Pro(CCT)
      5GFP

<400> SEQUENCE: 84

Met Pro Pro Pro Pro Ser Lys Gly Glu Glu Leu Phe Thr Gly Val
 1               5                   10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
```

-continued

```
                35                  40                  45
Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
210                 215                 220

Leu Leu Glu Phe Val Thr Ala Ala Gly Ile Thr His Gly Met Asp Glu
225                 230                 235                 240

Leu Tyr Lys
```

<210> SEQ ID NO 85
<211> LENGTH: 732
<212> TYPE: DNA
<213> ORGANISM: Artificial Sequence
<220> FEATURE:
<223> OTHER INFORMATION: Description of Artificial Sequence: Pro(CGA)
      5GFP
<220> FEATURE:
<221> NAME/KEY: CDS
<222> LOCATION: (1)..(732)

<400> SEQUENCE: 85

```
atg cga cga cga cga cga agc aag ggc gag gaa ctg ttc act ggc gtg    48
Met Arg Arg Arg Arg Arg Ser Lys Gly Glu Glu Leu Phe Thr Gly Val
  1               5                  10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc   144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca   192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca   240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc   288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag   336
```

```
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 86
<211> LENGTH: 243
<212> TYPE: PRT
<213> ORGANISM: Artificial Sequence
<220> FEATURE:
<223> OTHER INFORMATION: Description of Artificial Sequence: Pro(CGA)
      5GFP

<400> SEQUENCE: 86

Met Arg Arg Arg Arg Ser Lys Gly Glu Glu Leu Phe Thr Gly Val
1               5                   10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160
```

-continued

```
                                Lys Gln Lys Asn Gly Ile Lys Val Asn Phe Lys Ile Arg His Asn Ile
                                                165                 170                 175

Glu Asp Gly Ser Val Gln Leu Ala Asp His Tyr Gln Gln Asn Thr Pro
                                            180                 185                 190

Ile Gly Asp Gly Pro Val Leu Leu Pro Asp Asn His Tyr Leu Ser Thr
                                        195                 200                 205

Gln Ser Ala Leu Ser Lys Asp Pro Asn Glu Lys Arg Asp His Met Val
                                    210                 215                 220

Leu Leu Glu Phe Val Thr Ala Ala Gly Ile Thr His Gly Met Asp Glu
                                225                 230                 235                 240

Leu Tyr Lys

<210> SEQ ID NO 87
<211> LENGTH: 732
<212> TYPE: DNA
<213> ORGANISM: Artificial Sequence
<220> FEATURE:
<223> OTHER INFORMATION: Description of Artificial Sequence: Ser(AGC)
      5GFP
<220> FEATURE:
<221> NAME/KEY: CDS
<222> LOCATION: (1)..(732)

<400> SEQUENCE: 87 atg agc agc agc agc agc agc aag ggc gag gaa ctg ttc act ggc gtg        48
Met Ser Ser Ser Ser Ser Ser Lys Gly Glu Glu Leu Phe Thr Gly Val
  1               5                  10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190
```

```
atc ggc gac ggc cct gtg ctc ctc cca gac aac cat tac ctg tcc acc      624
Ile Gly Asp Gly Pro Val Leu Leu Pro Asp Asn His Tyr Leu Ser Thr
            195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 88
<211> LENGTH: 243
<212> TYPE: PRT
<213> ORGANISM: Artificial Sequence
<220> FEATURE:
<223> OTHER INFORMATION: Description of Artificial Sequence: Ser(AGC) 5GFP

<400> SEQUENCE: 88

```
Met Ser Ser Ser Ser Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 89
<211> LENGTH: 732
<212> TYPE: DNA
<213> ORGANISM: Artificial Sequence
<220> FEATURE:

<223> OTHER INFORMATION: Description of Artificial Sequence: Ser(AGT)
     5GFP
<220> FEATURE:
<221> NAME/KEY: CDS
<222> LOCATION: (1)..(732)

<400> SEQUENCE: 89

```
atg agt agt agt agt agt agc aag ggc gag gaa ctg ttc act ggc gtg      48
Met Ser Ser Ser Ser Ser Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys
```

<210> SEQ ID NO 90
<211> LENGTH: 243
<212> TYPE: PRT
<213> ORGANISM: Artificial Sequence
<220> FEATURE:
<223> OTHER INFORMATION: Description of Artificial Sequence: Ser(AGT)
     5GFP -continued

<400> SEQUENCE: 90

Met Ser Ser Ser Ser Ser Lys Gly Glu Glu Leu Phe Thr Gly Val
1               5                   10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 91
<211> LENGTH: 732
<212> TYPE: DNA
<213> ORGANISM: Artificial Sequence
<220> FEATURE:
<223> OTHER INFORMATION: Description of Artificial Sequence: Ser(TCA)
      5GFP
<220> FEATURE:
<221> NAME/KEY: CDS
<222> LOCATION: (1)..(732)

<400> SEQUENCE: 91

| | | |
|---|---|---|
| atg tca tca tca tca tca agc aag ggc gag gaa ctg ttc act ggc gtg | | 48 |
| Met Ser Ser Ser Ser Ser Lys Gly Glu Glu Leu Phe Thr Gly Val | | |
| 1               5                   10                  15 | | |
| | | |
| gtc cca att ctc gtg gaa ctg gat ggc gat gtg aat ggg cac aaa ttt | | 96 |
| Val Pro Ile Leu Val Glu Leu Asp Gly Asp Val Asn Gly His Lys Phe | | |
|             20                  25                  30 | | |
| | | |
| tct gtc agc gga gag ggt gaa ggt gat gcc aca tac gga aag ctc acc | | 144 |
| Ser Val Ser Gly Glu Gly Glu Gly Asp Ala Thr Tyr Gly Lys Leu Thr | | |
|         35                  40                  45 | | |
| | | |
| ctg aaa ttc atc tgc acc act gga aag ctc cct gtg cca tgg cca aca | | 192 |
| Leu Lys Phe Ile Cys Thr Thr Gly Lys Leu Pro Val Pro Trp Pro Thr | | |
|     50                  55                  60 | | |

```
ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc       624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc       672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag       720
Leu Leu Glu Phe Val Thr Ala Ala Gly Ile Thr His Gly Met Asp Glu
225                 230                 235                 240 ctg tac aag tga                                                       732
Leu Tyr Lys <210> SEQ ID NO 92
<211> LENGTH: 243
<212> TYPE: PRT
<213> ORGANISM: Artificial Sequence
<220> FEATURE:
<223> OTHER INFORMATION: Description of Artificial Sequence: Ser(TCA)
      5GFP

<400> SEQUENCE: 92

Met Ser Ser Ser Ser Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110
```

-continued

```
Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 93
<211> LENGTH: 732
<212> TYPE: DNA
<213> ORGANISM: Artificial Sequence
<220> FEATURE:
<223> OTHER INFORMATION: Description of Artificial Sequence: Ser(TCC)
      5GFP
<220> FEATURE:
<221> NAME/KEY: CDS
<222> LOCATION: (1)..(732)

<400> SEQUENCE: 93

```
atg tcc tcc tcc tcc tcc agc aag ggc gag gaa ctg ttc act ggc gtg      48
Met Ser Ser Ser Ser Ser Ser Lys Gly Glu Glu Leu Phe Thr Gly Val
  1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
```

```
                                                              -continued
145                  150                  155                  160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 94
<211> LENGTH: 243
<212> TYPE: PRT
<213> ORGANISM: Artificial Sequence
<220> FEATURE:
<223> OTHER INFORMATION: Description of Artificial Sequence: Ser(TCC)
      5GFP

<400> SEQUENCE: 94

Met Ser Ser Ser Ser Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
    65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
```

```
                  225                 230                 235                 240

Leu Tyr Lys

<210> SEQ ID NO 95
<211> LENGTH: 732
<212> TYPE: DNA
<213> ORGANISM: Artificial Sequence
<220> FEATURE:
<223> OTHER INFORMATION: Description of Artificial Sequence: Ser(TCG)
      5GFP
<220> FEATURE:
<221> NAME/KEY: CDS
<222> LOCATION: (1)..(732)

<400> SEQUENCE: 95 atg  tcg  tcg  tcg  tcg  tcg  agc  aag  ggc  gag  gaa  ctg  ttc  act  ggc  gtg         48
Met  Ser  Ser  Ser  Ser  Ser  Ser  Lys  Gly  Glu  Glu  Leu  Phe  Thr  Gly  Val
 1                    5                   10                   15 gtc  cca  att  ctc  gtg  gaa  ctg  gat  ggc  gat  gtg  aat  ggg  cac  aaa  ttt         96
Val  Pro  Ile  Leu  Val  Glu  Leu  Asp  Gly  Asp  Val  Asn  Gly  His  Lys  Phe
                20                   25                   30 tct  gtc  agc  gga  gag  ggt  gaa  ggt  gat  gcc  aca  tac  gga  aag  ctc  acc        144
Ser  Val  Ser  Gly  Glu  Gly  Glu  Gly  Asp  Ala  Thr  Tyr  Gly  Lys  Leu  Thr
           35                   40                   45 ctg  aaa  ttc  atc  tgc  acc  act  gga  aag  ctc  cct  gtg  cca  tgg  cca  aca        192
Leu  Lys  Phe  Ile  Cys  Thr  Thr  Gly  Lys  Leu  Pro  Val  Pro  Trp  Pro  Thr
 50                   55                   60 ctg  gtc  act  acc  ttc  tct  tat  ggc  gtg  cag  tgc  ttt  tcc  aga  tac  cca        240
Leu  Val  Thr  Thr  Phe  Ser  Tyr  Gly  Val  Gln  Cys  Phe  Ser  Arg  Tyr  Pro
 65                   70                   75                   80 gac  cat  atg  aag  cag  cat  gac  ttt  ttc  aag  agc  gcc  atg  ccc  gag  ggc        288
Asp  His  Met  Lys  Gln  His  Asp  Phe  Phe  Lys  Ser  Ala  Met  Pro  Glu  Gly
                85                   90                   95 tat  gtg  cag  gag  aga  acc  atc  ttt  ttc  aaa  gat  gac  ggg  aac  tac  aag        336
Tyr  Val  Gln  Glu  Arg  Thr  Ile  Phe  Phe  Lys  Asp  Asp  Gly  Asn  Tyr  Lys
           100                  105                  110 acc  cgc  gct  gaa  gtc  aag  ttc  gaa  ggt  gac  acc  ctg  gtg  aat  aga  atc        384
Thr  Arg  Ala  Glu  Val  Lys  Phe  Glu  Gly  Asp  Thr  Leu  Val  Asn  Arg  Ile
 115                  120                  125 gag  ctg  aag  ggc  att  gac  ttt  aag  gag  gat  gga  aac  att  ctc  ggc  cac        432
Glu  Leu  Lys  Gly  Ile  Asp  Phe  Lys  Glu  Asp  Gly  Asn  Ile  Leu  Gly  His
           130                  135                  140 aag  ctg  gaa  tac  aac  tat  aac  tcc  cac  aat  gtg  tac  atc  atg  gcc  gac        480
Lys  Leu  Glu  Tyr  Asn  Tyr  Asn  Ser  His  Asn  Val  Tyr  Ile  Met  Ala  Asp
145                  150                  155                  160 aag  caa  aag  aat  ggc  atc  aag  gtc  aac  ttc  aag  atc  aga  cac  aac  att        528
Lys  Gln  Lys  Asn  Gly  Ile  Lys  Val  Asn  Phe  Lys  Ile  Arg  His  Asn  Ile
                165                  170                  175 gag  gat  gga  tcc  gtg  cag  ctg  gcc  gac  cat  tat  caa  cag  aac  act  cca        576
Glu  Asp  Gly  Ser  Val  Gln  Leu  Ala  Asp  His  Tyr  Gln  Gln  Asn  Thr  Pro
           180                  185                  190 atc  ggc  gac  ggc  cct  gtg  ctc  ctc  cca  gac  aac  cat  tac  ctg  tcc  acc        624
Ile  Gly  Asp  Gly  Pro  Val  Leu  Leu  Pro  Asp  Asn  His  Tyr  Leu  Ser  Thr
 195                  200                  205 cag  tct  gcc  ctg  tct  aaa  gat  ccc  aac  gaa  aag  aga  gac  cac  atg  gtc        672
Gln  Ser  Ala  Leu  Ser  Lys  Asp  Pro  Asn  Glu  Lys  Arg  Asp  His  Met  Val
           210                  215                  220 ctg  ctg  gag  ttt  gtg  acc  gct  gct  ggg  atc  aca  cat  ggc  atg  gac  gag        720
Leu  Leu  Glu  Phe  Val  Thr  Ala  Ala  Gly  Ile  Thr  His  Gly  Met  Asp  Glu
225                  230                  235                  240 ctg  tac  aag  tga                                                                     732
```

<210> SEQ ID NO 96
<211> LENGTH: 243
<212> TYPE: PRT
<213> ORGANISM: Artificial Sequence
<220> FEATURE:
<223> OTHER INFORMATION: Description of Artificial Sequence: Ser(TCG) 5GFP

<400> SEQUENCE: 96

Met Ser Ser Ser Ser Ser Lys Gly Glu Glu Leu Phe Thr Gly Val
1               5                   10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 97
<211> LENGTH: 732
<212> TYPE: DNA
<213> ORGANISM: Artificial Sequence
<220> FEATURE:
<223> OTHER INFORMATION: Description of Artificial Sequence: Ser(TCT) 5GFP
<220> FEATURE:
<221> NAME/KEY: CDS
<222> LOCATION: (1)..(732)

<400> SEQUENCE: 97 atg tct tct tct tct tct agc aag ggc gag gaa ctg ttc act ggc gtg     48
Met Ser Ser Ser Ser Ser Ser Lys Gly Glu Glu Leu Phe Thr Gly Val
1               5                   10                  15 gtc cca att ctc gtg gaa ctg gat ggc gat gtg aat ggg cac aaa ttt     96

```
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys <210> SEQ ID NO 98
<211> LENGTH: 243
<212> TYPE: PRT
<213> ORGANISM: Artificial Sequence
<220> FEATURE:
<223> OTHER INFORMATION: Description of Artificial Sequence: Ser(TCT)
      5GFP

<400> SEQUENCE: 98

Met Ser Ser Ser Ser Ser Lys Gly Glu Glu Leu Phe Thr Gly Val
  1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
```

-continued

```
         50                  55                  60
Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 99
<211> LENGTH: 732
<212> TYPE: DNA
<213> ORGANISM: Artificial Sequence
<220> FEATURE:
<223> OTHER INFORMATION: Description of Artificial Sequence: Thr(ACA) 5GFP
<220> FEATURE:
<221> NAME/KEY: CDS
<222> LOCATION: (1)..(732)

<400> SEQUENCE: 99

```
atg aca aca aca aca aca agc aag ggc gag gaa ctg ttc act ggc gtg      48
Met Thr Thr Thr Thr Thr Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
                100                 105                 110
```

```
acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 100
<211> LENGTH: 243
<212> TYPE: PRT
<213> ORGANISM: Artificial Sequence
<220> FEATURE:
<223> OTHER INFORMATION: Description of Artificial Sequence: Thr(ACA)
      5GFP

<400> SEQUENCE: 100

Met Thr Thr Thr Thr Thr Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175
```

```
Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys

<210> SEQ ID NO 101
<211> LENGTH: 732
<212> TYPE: DNA
<213> ORGANISM: Artificial Sequence
<220> FEATURE:
<223> OTHER INFORMATION: Description of Artificial Sequence: Thr(ACC)
      5GFP
<220> FEATURE:
<221> NAME/KEY: CDS
<222> LOCATION: (1)..(732)

<400> SEQUENCE: 101
```

| | | | | | | | | | | | | | | | | |
|---|---|---|---|---|---|---|---|---|---|---|---|---|---|---|---|---|
| atg | acc | acc | acc | acc | acc | agc | aag | ggc | gag | gaa | ctg | ttc | act | ggc | gtg | 48 |
| Met | Thr | Thr | Thr | Thr | Thr | Ser | Lys | Gly | Glu | Glu | Leu | Phe | Thr | Gly | Val | |
| 1 | | | | 5 | | | | | 10 | | | | | 15 | | |
| gtc | cca | att | ctc | gtg | gaa | ctg | gat | ggc | gat | gtg | aat | ggg | cac | aaa | ttt | 96 |
| Val | Pro | Ile | Leu | Val | Glu | Leu | Asp | Gly | Asp | Val | Asn | Gly | His | Lys | Phe | |
| | | | | 20 | | | | | 25 | | | | | 30 | | |
| tct | gtc | agc | gga | gag | ggt | gaa | ggt | gat | gcc | aca | tac | gga | aag | ctc | acc | 144 |
| Ser | Val | Ser | Gly | Glu | Gly | Glu | Gly | Asp | Ala | Thr | Tyr | Gly | Lys | Leu | Thr | |
| | | 35 | | | | | 40 | | | | | 45 | | | | |
| ctg | aaa | ttc | atc | tgc | acc | act | gga | aag | ctc | cct | gtg | cca | tgg | cca | aca | 192 |
| Leu | Lys | Phe | Ile | Cys | Thr | Thr | Gly | Lys | Leu | Pro | Val | Pro | Trp | Pro | Thr | |
| | 50 | | | | | 55 | | | | | 60 | | | | | |
| ctg | gtc | act | acc | ttc | tct | tat | ggc | gtg | cag | tgc | ttt | tcc | aga | tac | cca | 240 |
| Leu | Val | Thr | Thr | Phe | Ser | Tyr | Gly | Val | Gln | Cys | Phe | Ser | Arg | Tyr | Pro | |
| 65 | | | | | 70 | | | | | 75 | | | | | 80 | |
| gac | cat | atg | aag | cag | cat | gac | ttt | ttc | aag | agc | gcc | atg | ccc | gag | ggc | 288 |
| Asp | His | Met | Lys | Gln | His | Asp | Phe | Phe | Lys | Ser | Ala | Met | Pro | Glu | Gly | |
| | | | | 85 | | | | | 90 | | | | | 95 | | |
| tat | gtg | cag | gag | aga | acc | atc | ttt | ttc | aaa | gat | gac | ggg | aac | tac | aag | 336 |
| Tyr | Val | Gln | Glu | Arg | Thr | Ile | Phe | Phe | Lys | Asp | Asp | Gly | Asn | Tyr | Lys | |
| | | | 100 | | | | | 105 | | | | | 110 | | | |
| acc | cgc | gct | gaa | gtc | aag | ttc | gaa | ggt | gac | acc | ctg | gtg | aat | aga | atc | 384 |
| Thr | Arg | Ala | Glu | Val | Lys | Phe | Glu | Gly | Asp | Thr | Leu | Val | Asn | Arg | Ile | |
| | | 115 | | | | | 120 | | | | | 125 | | | | |
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| | 130 | | | | | 135 | | | | | 140 | | | | | |
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | | 150 | | | | | 155 | | | | | 160 | |
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | | 180 | | | | | 185 | | | | | 190 | | | |
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |
| | | 195 | | | | | 200 | | | | | 205 | | | | |

-continued

```
cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 102
<211> LENGTH: 243
<212> TYPE: PRT
<213> ORGANISM: Artificial Sequence
<220> FEATURE:
<223> OTHER INFORMATION: Description of Artificial Sequence: Thr(ACC)
      5GFP

<400> SEQUENCE: 102

Met Thr Thr Thr Thr Thr Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 103
<211> LENGTH: 732
<212> TYPE: DNA
<213> ORGANISM: Artificial Sequence
<220> FEATURE:
<223> OTHER INFORMATION: Description of Artificial Sequence: Thr(ACG)
      5GFP
<220> FEATURE:
```

<221> NAME/KEY: CDS
<222> LOCATION: (1)..(732)

<400> SEQUENCE: 103

| | | | | | | | | | | | | | | | | |
|---|---|---|---|---|---|---|---|---|---|---|---|---|---|---|---|---|
| atg | acg | acg | acg | acg | acg | agc | aag | ggc | gag | gaa | ctg | ttc | act | ggc | gtg | 48 |
| Met | Thr | Thr | Thr | Thr | Thr | Ser | Lys | Gly | Glu | Glu | Leu | Phe | Thr | Gly | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtc | cca | att | ctc | gtg | gaa | ctg | gat | ggc | gat | gtg | aat | ggg | cac | aaa | ttt | 96 |
| Val | Pro | Ile | Leu | Val | Glu | Leu | Asp | Gly | Asp | Val | Asn | Gly | His | Lys | Phe | |
| | | | 20 | | | | | 25 | | | | | 30 | | | |

| | | | | | | | | | | | | | | | | |
|---|---|---|---|---|---|---|---|---|---|---|---|---|---|---|---|---|
| tct | gtc | agc | gga | gag | ggt | gaa | ggt | gat | gcc | aca | tac | gga | aag | ctc | acc | 144 |
| Ser | Val | Ser | Gly | Glu | Gly | Glu | Gly | Asp | Ala | Thr | Tyr | Gly | Lys | Leu | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| ctg | aaa | ttc | atc | tgc | acc | act | gga | aag | ctc | cct | gtg | cca | tgg | cca | aca | 192 |
| Leu | Lys | Phe | Ile | Cys | Thr | Thr | Gly | Lys | Leu | Pro | Val | Pro | Trp | Pro | Thr | |
| 50 | | | | | 55 | | | | | 60 | | | | | | |

| | | | | | | | | | | | | | | | | |
|---|---|---|---|---|---|---|---|---|---|---|---|---|---|---|---|---|
| ctg | gtc | act | acc | ttc | tct | tat | ggc | gtg | cag | tgc | ttt | tcc | aga | tac | cca | 240 |
| Leu | Val | Thr | Thr | Phe | Ser | Tyr | Gly | Val | Gln | Cys | Phe | Ser | Arg | Tyr | Pro | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gac | cat | atg | aag | cag | cat | gac | ttt | ttc | aag | agc | gcc | atg | ccc | gag | ggc | 288 |
| Asp | His | Met | Lys | Gln | His | Asp | Phe | Phe | Lys | Ser | Ala | Met | Pro | Glu | Gly | |
| | | | 85 | | | | | 90 | | | | | 95 | | | |

| | | | | | | | | | | | | | | | | |
|---|---|---|---|---|---|---|---|---|---|---|---|---|---|---|---|---|
| tat | gtg | cag | gag | aga | acc | atc | ttt | ttc | aaa | gat | gac | ggg | aac | tac | aag | 336 |
| Tyr | Val | Gln | Glu | Arg | Thr | Ile | Phe | Phe | Lys | Asp | Asp | Gly | Asn | Tyr | Lys | |
| | | 100 | | | | | 105 | | | | | 110 | | | | |

| | | | | | | | | | | | | | | | | |
|---|---|---|---|---|---|---|---|---|---|---|---|---|---|---|---|---|
| acc | cgc | gct | gaa | gtc | aag | ttc | gaa | ggt | gac | acc | ctg | gtg | aat | aga | atc | 384 |
| Thr | Arg | Ala | Glu | Val | Lys | Phe | Glu | Gly | Asp | Thr | Leu | Val | Asn | Arg | Ile | |
| | | | 115 | | | | | 120 | | | | | 125 | | | |

| | | | | | | | | | | | | | | | | |
|---|---|---|---|---|---|---|---|---|---|---|---|---|---|---|---|---|
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| 130 | | | | | 135 | | | | | 140 | | | | | | |

| | | | | | | | | | | | | | | | | |
|---|---|---|---|---|---|---|---|---|---|---|---|---|---|---|---|---|
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |
| | | | 195 | | | | | 200 | | | | | 205 | | | |

| | | | | | | | | | | | | | | | | |
|---|---|---|---|---|---|---|---|---|---|---|---|---|---|---|---|---|
| cag | tct | gcc | ctg | tct | aaa | gat | ccc | aac | gaa | aag | aga | gac | cac | atg | gtc | 672 |
| Gln | Ser | Ala | Leu | Ser | Lys | Asp | Pro | Asn | Glu | Lys | Arg | Asp | His | Met | Val | |
| | | 210 | | | | | 215 | | | | | 220 | | | | |

| | | | | | | | | | | | | | | | | |
|---|---|---|---|---|---|---|---|---|---|---|---|---|---|---|---|---|
| ctg | ctg | gag | ttt | gtg | acc | gct | gct | ggg | atc | aca | cat | ggc | atg | gac | gag | 720 |
| Leu | Leu | Glu | Phe | Val | Thr | Ala | Ala | Gly | Ile | Thr | His | Gly | Met | Asp | Glu | |
| 225 | | | | 230 | | | | | 235 | | | | | 240 | | |

| | | | | |
|---|---|---|---|---|
| ctg | tac | aag | tga | 732 |
| Leu | Tyr | Lys | | |

<210> SEQ ID NO 104
<211> LENGTH: 243
<212> TYPE: PRT
<213> ORGANISM: Artificial Sequence
<220> FEATURE:
<223> OTHER INFORMATION: Description of Artificial Sequence: Thr(ACG) 5GFP

<400> SEQUENCE: 104

-continued

```
Met Thr Thr Thr Thr Thr Ser Lys Gly Glu Glu Leu Phe Thr Gly Val
  1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
             100                 105                 110

Thr Arg Ala Glu Val Lys Phe Glu Gly Asp Thr Leu Val Asn Arg Ile
         115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 105
<211> LENGTH: 732
<212> TYPE: DNA
<213> ORGANISM: Artificial Sequence
<220> FEATURE:
<223> OTHER INFORMATION: Description of Artificial Sequence: Thr(ACT) 5GFP
<220> FEATURE:
<221> NAME/KEY: CDS
<222> LOCATION: (1)..(732)

<400> SEQUENCE: 105

```
atg act act act act act agc aag ggc gag gaa ctg ttc act ggc gtg      48
Met Thr Thr Thr Thr Thr Ser Lys Gly Glu Glu Leu Phe Thr Gly Val
  1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80
```

```
gac cat atg aag cag cat gac ttt ttc aag agc gcc atg ccc gag ggc    288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys <210> SEQ ID NO 106
<211> LENGTH: 243
<212> TYPE: PRT
<213> ORGANISM: Artificial Sequence
<220> FEATURE:
<223> OTHER INFORMATION: Description of Artificial Sequence: Thr(ACT)
      5GFP

<400> SEQUENCE: 106

Met Thr Thr Thr Thr Thr Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125
```

```
Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 107
<211> LENGTH: 732
<212> TYPE: DNA
<213> ORGANISM: Artificial Sequence
<220> FEATURE:
<223> OTHER INFORMATION: Description of Artificial Sequence: Trp(TGG)
      5GFP
<220> FEATURE:
<221> NAME/KEY: CDS
<222> LOCATION: (1)..(732)

<400> SEQUENCE: 107 atg tgg tgg tgg tgg tgg agc aag ggc gag gaa ctg ttc act ggc gtg    48
Met Trp Trp Trp Trp Trp Ser Lys Gly Glu Glu Leu Phe Thr Gly Val
 1               5                  10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc   144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca   192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca   240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc   288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag   336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc   384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac   432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac   480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att   528
```

```
                                                    -continued

Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys
```

<210> SEQ ID NO 108
<211> LENGTH: 243
<212> TYPE: PRT
<213> ORGANISM: Artificial Sequence
<220> FEATURE:
<223> OTHER INFORMATION: Description of Artificial Sequence: Trp(TGG) 5GFP

<400> SEQUENCE: 108

```
Met Trp Trp Trp Trp Trp Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 109
<211> LENGTH: 732
<212> TYPE: DNA
<213> ORGANISM: Artificial Sequence
<220> FEATURE:
<223> OTHER INFORMATION: Description of Artificial Sequence: Tyr(TAT) 5GFP
<220> FEATURE:
<221> NAME/KEY: CDS
<222> LOCATION: (1)..(732)

<400> SEQUENCE: 109

| | | |
|---|---|---|
| atg tat tat tat tat tat agc aag ggc gag gaa ctg ttc act ggc gtg<br>Met Tyr Tyr Tyr Tyr Tyr Ser Lys Gly Glu Glu Leu Phe Thr Gly Val<br>1                        5                      10                   15 | | 48 |
| gtc cca att ctc gtg gaa ctg gat ggc gat gtg aat ggg cac aaa ttt<br>Val Pro Ile Leu Val Glu Leu Asp Gly Asp Val Asn Gly His Lys Phe<br>                   20                      25                      30 | | 96 |
| tct gtc agc gga gag ggt gaa ggt gat gcc aca tac gga aag ctc acc<br>Ser Val Ser Gly Glu Gly Glu Gly Asp Ala Thr Tyr Gly Lys Leu Thr<br>           35                      40                      45 | | 144 |
| ctg aaa ttc atc tgc acc act gga aag ctc cct gtg cca tgg cca aca<br>Leu Lys Phe Ile Cys Thr Thr Gly Lys Leu Pro Val Pro Trp Pro Thr<br> 50                      55                      60 | | 192 |
| ctg gtc act acc ttc tct tat ggc gtg cag tgc ttt tcc aga tac cca<br>Leu Val Thr Thr Phe Ser Tyr Gly Val Gln Cys Phe Ser Arg Tyr Pro<br>65                      70                      75                   80 | | 240 |
| gac cat atg aag cag cat gac ttt ttc aag agc gcc atg ccc gag ggc<br>Asp His Met Lys Gln His Asp Phe Phe Lys Ser Ala Met Pro Glu Gly<br>                   85                      90                      95 | | 288 |
| tat gtg cag gag aga acc atc ttt ttc aaa gat gac ggg aac tac aag<br>Tyr Val Gln Glu Arg Thr Ile Phe Phe Lys Asp Asp Gly Asn Tyr Lys<br>           100                     105                     110 | | 336 |
| acc cgc gct gaa gtc aag ttc gaa ggt gac acc ctg gtg aat aga atc<br>Thr Arg Ala Glu Val Lys Phe Glu Gly Asp Thr Leu Val Asn Arg Ile<br>         115                     120                     125 | | 384 |
| gag ctg aag ggc att gac ttt aag gag gat gga aac att ctc ggc cac<br>Glu Leu Lys Gly Ile Asp Phe Lys Glu Asp Gly Asn Ile Leu Gly His<br> 130                      135                     140 | | 432 |
| aag ctg gaa tac aac tat aac tcc cac aat gtg tac atc atg gcc gac<br>Lys Leu Glu Tyr Asn Tyr Asn Ser His Asn Val Tyr Ile Met Ala Asp<br>145                    150                     155                   160 | | 480 |
| aag caa aag aat ggc atc aag gtc aac ttc aag atc aga cac aac att<br>Lys Gln Lys Asn Gly Ile Lys Val Asn Phe Lys Ile Arg His Asn Ile<br>                   165                     170                   175 | | 528 |
| gag gat gga tcc gtg cag ctg gcc gac cat tat caa cag aac act cca<br>Glu Asp Gly Ser Val Gln Leu Ala Asp His Tyr Gln Gln Asn Thr Pro<br>           180                     185                     190 | | 576 |
| atc ggc gac ggc cct gtg ctc ctc cca gac aac cat tac ctg tcc acc<br>Ile Gly Asp Gly Pro Val Leu Leu Pro Asp Asn His Tyr Leu Ser Thr<br>         195                     200                     205 | | 624 |
| cag tct gcc ctg tct aaa gat ccc aac gaa aag aga gac cac atg gtc<br>Gln Ser Ala Leu Ser Lys Asp Pro Asn Glu Lys Arg Asp His Met Val<br> 210                      215                     220 | | 672 |
| ctg ctg gag ttt gtg acc gct gct ggg atc aca cat ggc atg gac gag<br>Leu Leu Glu Phe Val Thr Ala Ala Gly Ile Thr His Gly Met Asp Glu<br>225                    230                     235                   240 | | 720 |
| ctg tac aag tga<br>Leu Tyr Lys | | 732 |

-continued

```
<210> SEQ ID NO 110
<211> LENGTH: 243
<212> TYPE: PRT
<213> ORGANISM: Artificial Sequence
<220> FEATURE:
<223> OTHER INFORMATION: Description of Artificial Sequence: Tyr(TAT)
      5GFP

<400> SEQUENCE: 110

Met Tyr Tyr Tyr Tyr Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 111
<211> LENGTH: 732
<212> TYPE: DNA
<213> ORGANISM: Artificial Sequence
<220> FEATURE:
<223> OTHER INFORMATION: Description of Artificial Sequence: Tyr(TAC)
      5GFP
<220> FEATURE:
<221> NAME/KEY: CDS
<222> LOCATION: (1)..(732)

<400> SEQUENCE: 111 atg tac tac tac tac tac agc aag ggc gag gaa ctg ttc act ggc gtg      48
Met Tyr Tyr Tyr Tyr Tyr Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30
```

|  |  |
|---|---|
| tct gtc agc gga gag ggt gaa ggt gat gcc aca tac gga aag ctc acc<br>Ser Val Ser Gly Glu Gly Glu Gly Asp Ala Thr Tyr Gly Lys Leu Thr<br>35 40 45 | 144 |
| ctg aaa ttc atc tgc acc act gga aag ctc cct gtg cca tgg cca aca<br>Leu Lys Phe Ile Cys Thr Thr Gly Lys Leu Pro Val Pro Trp Pro Thr<br>50 55 60 | 192 |
| ctg gtc act acc ttc tct tat ggc gtg cag tgc ttt tcc aga tac cca<br>Leu Val Thr Thr Phe Ser Tyr Gly Val Gln Cys Phe Ser Arg Tyr Pro<br>65 70 75 80 | 240 |
| gac cat atg aag cag cat gac ttt ttc aag agc gcc atg ccc gag ggc<br>Asp His Met Lys Gln His Asp Phe Phe Lys Ser Ala Met Pro Glu Gly<br>85 90 95 | 288 |
| tat gtg cag gag aga acc atc ttt ttc aaa gat gac ggg aac tac aag<br>Tyr Val Gln Glu Arg Thr Ile Phe Phe Lys Asp Asp Gly Asn Tyr Lys<br>100 105 110 | 336 |
| acc cgc gct gaa gtc aag ttc gaa ggt gac acc ctg gtg aat aga atc<br>Thr Arg Ala Glu Val Lys Phe Glu Gly Asp Thr Leu Val Asn Arg Ile<br>115 120 125 | 384 |
| gag ctg aag ggc att gac ttt aag gag gat gga aac att ctc ggc cac<br>Glu Leu Lys Gly Ile Asp Phe Lys Glu Asp Gly Asn Ile Leu Gly His<br>130 135 140 | 432 |
| aag ctg gaa tac aac tat aac tcc cac aat gtg tac atc atg gcc gac<br>Lys Leu Glu Tyr Asn Tyr Asn Ser His Asn Val Tyr Ile Met Ala Asp<br>145 150 155 160 | 480 |
| aag caa aag aat ggc atc aag gtc aac ttc aag atc aga cac aac att<br>Lys Gln Lys Asn Gly Ile Lys Val Asn Phe Lys Ile Arg His Asn Ile<br>165 170 175 | 528 |
| gag gat gga tcc gtg cag ctg gcc gac cat tat caa cag aac act cca<br>Glu Asp Gly Ser Val Gln Leu Ala Asp His Tyr Gln Gln Asn Thr Pro<br>180 185 190 | 576 |
| atc ggc gac ggc cct gtg ctc ctc cca gac aac cat tac ctg tcc acc<br>Ile Gly Asp Gly Pro Val Leu Leu Pro Asp Asn His Tyr Leu Ser Thr<br>195 200 205 | 624 |
| cag tct gcc ctg tct aaa gat ccc aac gaa aag aga gac cac atg gtc<br>Gln Ser Ala Leu Ser Lys Asp Pro Asn Glu Lys Arg Asp His Met Val<br>210 215 220 | 672 |
| ctg ctg gag ttt gtg acc gct gct ggg atc aca cat ggc atg gac gag<br>Leu Leu Glu Phe Val Thr Ala Ala Gly Ile Thr His Gly Met Asp Glu<br>225 230 235 240 | 720 |
| ctg tac aag tga<br>Leu Tyr Lys | 732 |

```
<210> SEQ ID NO 112
<211> LENGTH: 243
<212> TYPE: PRT
<213> ORGANISM: Artificial Sequence
<220> FEATURE:
<223> OTHER INFORMATION: Description of Artificial Sequence: Tyr(TAC)
      5GFP

<400> SEQUENCE: 112
```

Met Tyr Tyr Tyr Tyr Ser Lys Gly Glu Glu Leu Phe Thr Gly Val
1               5                   10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro

-continued

```
                65                  70                  75                  80
Asp His Met Lys Gln His Asp Phe Phe Lys Ser Ala Met Pro Glu Gly
                    85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
                115                 120                 125

Glu Leu Lys Gly Ile Asp Phe Lys Glu Asp Gly Asn Ile Leu Gly His
            130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
                180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
210                 215                 220

Leu Leu Glu Phe Val Thr Ala Ala Gly Ile Thr His Gly Met Asp Glu
225                 230                 235                 240

Leu Tyr Lys
```

<210> SEQ ID NO 113
<211> LENGTH: 732
<212> TYPE: DNA
<213> ORGANISM: Artificial Sequence
<220> FEATURE:
<223> OTHER INFORMATION: Description of Artificial Sequence: Val(GTA)
      5GFP
<220> FEATURE:
<221> NAME/KEY: CDS
<222> LOCATION: (1)..(732)

<400> SEQUENCE: 113

```
atg gta gta gta gta gta agc aag ggc gag gaa ctg ttc act ggc gtg      48
Met Val Val Val Val Val Ser Lys Gly Glu Glu Leu Phe Thr Gly Val
  1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                     85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
                100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
            115                 120                 125
```

| | | | | | | | | | | | | | | | | |
|---|---|---|---|---|---|---|---|---|---|---|---|---|---|---|---|---|
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| | 130 | | | | 135 | | | | | 140 | | | | | | |
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | | 150 | | | | | 155 | | | | | 160 | |
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | | 180 | | | | | 185 | | | | | 190 | | | |
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |
| | | 195 | | | | | 200 | | | | | 205 | | | | |
| cag | tct | gcc | ctg | tct | aaa | gat | ccc | aac | gaa | aag | aga | gac | cac | atg | gtc | 672 |
| Gln | Ser | Ala | Leu | Ser | Lys | Asp | Pro | Asn | Glu | Lys | Arg | Asp | His | Met | Val | |
| 210 | | | | | 215 | | | | | 220 | | | | | | |
| ctg | ctg | gag | ttt | gtg | acc | gct | gct | ggg | atc | aca | cat | ggc | atg | gac | gag | 720 |
| Leu | Leu | Glu | Phe | Val | Thr | Ala | Ala | Gly | Ile | Thr | His | Gly | Met | Asp | Glu | |
| 225 | | | | 230 | | | | | 235 | | | | | 240 | | |
| ctg | tac | aag | tga | | | | | | | | | | | | | 732 |
| Leu | Tyr | Lys | | | | | | | | | | | | | | |

<210> SEQ ID NO 114
<211> LENGTH: 243
<212> TYPE: PRT
<213> ORGANISM: Artificial Sequence
<220> FEATURE:
<223> OTHER INFORMATION: Description of Artificial Sequence: Val(GTA)
    5GFP

<400> SEQUENCE: 114

Met Val Val Val Val Ser Lys Gly Glu Glu Leu Phe Thr Gly Val
 1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

-continued

```
Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 115
<211> LENGTH: 732
<212> TYPE: DNA
<213> ORGANISM: Artificial Sequence
<220> FEATURE:
<223> OTHER INFORMATION: Description of Artificial Sequence: Val(GTC)
      5GFP
<220> FEATURE:
<221> NAME/KEY: CDS
<222> LOCATION: (1)..(732)

<400> SEQUENCE: 115 atg gtc gtc gtc gtc agc aag ggc gag gaa ctg ttc act ggc gtg        48
Met Val Val Val Val Ser Lys Gly Glu Glu Leu Phe Thr Gly Val
 1               5                  10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
```

```
                 210                 215                 220
ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 116
<211> LENGTH: 243
<212> TYPE: PRT
<213> ORGANISM: Artificial Sequence
<220> FEATURE:
<223> OTHER INFORMATION: Description of Artificial Sequence: Val(GTC)
      5GFP

<400> SEQUENCE: 116

Met Val Val Val Val Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 117
<211> LENGTH: 732
<212> TYPE: DNA
<213> ORGANISM: Artificial Sequence
<220> FEATURE:
<223> OTHER INFORMATION: Description of Artificial Sequence: Val(GTG)
      5GFP
<220> FEATURE:
<221> NAME/KEY: CDS
<222> LOCATION: (1)..(732)
```

```
<400> SEQUENCE: 117 atg gtg gtg gtg gtg gtg agc aag ggc gag gaa ctg ttc act ggc gtg      48
Met Val Val Val Val Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys <210> SEQ ID NO 118
<211> LENGTH: 243
<212> TYPE: PRT
<213> ORGANISM: Artificial Sequence
<220> FEATURE:
<223> OTHER INFORMATION: Description of Artificial Sequence: Val(GTG)
      5GFP

<400> SEQUENCE: 118

Met Val Val Val Val Ser Lys Gly Glu Glu Leu Phe Thr Gly Val
 1               5                  10                  15
```

-continued

```
Val Pro Ile Leu Val Glu Leu Asp Gly Asp Val Asn Gly His Lys Phe
             20                  25                  30
Ser Val Ser Gly Glu Gly Gly Asp Ala Thr Tyr Gly Lys Leu Thr
         35                  40                  45
Leu Lys Phe Ile Cys Thr Thr Gly Lys Leu Pro Val Pro Trp Pro Thr
 50                  55                  60
Leu Val Thr Thr Phe Ser Tyr Gly Val Gln Cys Phe Ser Arg Tyr Pro
 65                  70                  75                  80
Asp His Met Lys Gln His Asp Phe Phe Lys Ser Ala Met Pro Glu Gly
                 85                  90                  95
Tyr Val Gln Glu Arg Thr Ile Phe Phe Lys Asp Asp Gly Asn Tyr Lys
             100                 105                 110
Thr Arg Ala Glu Val Lys Phe Glu Gly Asp Thr Leu Val Asn Arg Ile
         115                 120                 125
Glu Leu Lys Gly Ile Asp Phe Lys Glu Asp Gly Asn Ile Leu Gly His
 130                 135                 140
Lys Leu Glu Tyr Asn Tyr Asn Ser His Asn Val Tyr Ile Met Ala Asp
145                 150                 155                 160
Lys Gln Lys Asn Gly Ile Lys Val Asn Phe Lys Ile Arg His Asn Ile
                 165                 170                 175
Glu Asp Gly Ser Val Gln Leu Ala Asp His Tyr Gln Gln Asn Thr Pro
             180                 185                 190
Ile Gly Asp Gly Pro Val Leu Leu Pro Asp Asn His Tyr Leu Ser Thr
         195                 200                 205
Gln Ser Ala Leu Ser Lys Asp Pro Asn Glu Lys Arg Asp His Met Val
 210                 215                 220
Leu Leu Glu Phe Val Thr Ala Ala Gly Ile Thr His Gly Met Asp Glu
225                 230                 235                 240
Leu Tyr Lys
```

<210> SEQ ID NO 119
<211> LENGTH: 732
<212> TYPE: DNA
<213> ORGANISM: Artificial Sequence
<220> FEATURE:
<223> OTHER INFORMATION: Description of Artificial Sequence: Val(GTT) 5GFP
<220> FEATURE:
<221> NAME/KEY: CDS
<222> LOCATION: (1)..(732)

<400> SEQUENCE: 119

```
atg gtt gtt gtt gtt gtt agc aag ggc gag gaa ctg ttc act ggc gtg      48
Met Val Val Val Val Val Ser Lys Gly Glu Glu Leu Phe Thr Gly Val
  1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
```

-continued

```
Asp His Met Lys Gln His Asp Phe Phe Lys Ser Ala Met Pro Glu Gly
             85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 120
<211> LENGTH: 243
<212> TYPE: PRT
<213> ORGANISM: Artificial Sequence
<220> FEATURE:
<223> OTHER INFORMATION: Description of Artificial Sequence: Val(GTT) 5GFP

<400> SEQUENCE: 120

```
Met Val Val Val Val Ser Lys Gly Glu Glu Leu Phe Thr Gly Val
  1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140
```

```
Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
            165                 170                 175

Glu Asp Gly Ser Val Gln Leu Ala Asp His Tyr Gln Gln Asn Thr Pro
        180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 121
<211> LENGTH: 732
<212> TYPE: DNA
<213> ORGANISM: Artificial Sequence
<220> FEATURE:
<223> OTHER INFORMATION: Description of Artificial Sequence: Stop(TAA)
      5GFP
<220> FEATURE:
<221> NAME/KEY: CDS
<222> LOCATION: (1)..(732)

<400> SEQUENCE: 121 atg taa taa taa taa taa agc aag ggc gag gaa ctg ttc act ggc gtg        48
Met                     Ser Lys Gly Glu Glu Leu Phe Thr Gly Val
1                         5                  10 gtc cca att ctc gtg gaa ctg gat ggc gat gtg aat ggg cac aaa ttt        96
Val Pro Ile Leu Val Glu Leu Asp Gly Asp Val Asn Gly His Lys Phe
            15                  20                  25 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
        30                  35                  40 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
    45                  50                  55 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
60                  65                  70                  75 gac cat atg aag cag cat gac ttt ttc aag agc gcc atg ccc gag ggc       288
Asp His Met Lys Gln His Asp Phe Phe Lys Ser Ala Met Pro Glu Gly
            80                  85                  90 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
        95                 100                 105 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
    110                 115                 120 gag ctg aag ggc att gac ttt aag gag gat gga aac att ctc ggc cac       432
Glu Leu Lys Gly Ile Asp Phe Lys Glu Asp Gly Asn Ile Leu Gly His
125                 130                 135 aag ctg gaa tac aac tat aac tcc cac aat gtg tac atc atg gcc gac       480
Lys Leu Glu Tyr Asn Tyr Asn Ser His Asn Val Tyr Ile Met Ala Asp
140                 145                 150                 155 aag caa aag aat ggc atc aag gtc aac ttc aag atc aga cac aac att       528
Lys Gln Lys Asn Gly Ile Lys Val Asn Phe Lys Ile Arg His Asn Ile
            160                 165                 170
```

```
gag gat gga tcc gtg cag ctg gcc gac cat tat caa cag aac act cca      576
Glu Asp Gly Ser Val Gln Leu Ala Asp His Tyr Gln Gln Asn Thr Pro
            175                 180                 185 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        190                 195                 200 cag tct gcc ctg tct aaa gat ccc aac gaa aag aga gac cac atg gtc      672
Gln Ser Ala Leu Ser Lys Asp Pro Asn Glu Lys Arg Asp His Met Val
    205                 210                 215 ctg ctg gag ttt gtg acc gct gct ggg atc aca cat ggc atg gac gag      720
Leu Leu Glu Phe Val Thr Ala Ala Gly Ile Thr His Gly Met Asp Glu
220                 225                 230                 235 ctg tac aag tga                                                      732
Leu Tyr Lys <210> SEQ ID NO 122
<211> LENGTH: 732
<212> TYPE: DNA
<213> ORGANISM: Artificial Sequence
<220> FEATURE:
<223> OTHER INFORMATION: Description of Artificial Sequence: Stop(TAG)
      5GFP
<220> FEATURE:
<221> NAME/KEY: CDS
<222> LOCATION: (1)..(732)

<400> SEQUENCE: 122 atg tag tag tag tag tag agc aag ggc gag gaa ctg ttc act ggc gtg       48
Met                     Ser Lys Gly Glu Glu Leu Phe Thr Gly Val
1                        5                  10 gtc cca att ctc gtg gaa ctg gat ggc gat gtg aat ggg cac aaa ttt       96
Val Pro Ile Leu Val Glu Leu Asp Gly Asp Val Asn Gly His Lys Phe
         15                  20                  25 tct gtc agc gga gag ggt gaa ggt gat gcc aca tac gga aag ctc acc      144
Ser Val Ser Gly Glu Gly Glu Gly Asp Ala Thr Tyr Gly Lys Leu Thr
        30                  35                  40 ctg aaa ttc atc tgc acc act gga aag ctc cct gtg cca tgg cca aca      192
Leu Lys Phe Ile Cys Thr Thr Gly Lys Leu Pro Val Pro Trp Pro Thr
    45                  50                  55 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
60                  65                  70                  75 gac cat atg aag cag cat gac ttt ttc aag agc gcc atg ccc gag ggc      288
Asp His Met Lys Gln His Asp Phe Phe Lys Ser Ala Met Pro Glu Gly
                80                  85                  90 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
             95                 100                 105 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        110                 115                 120 gag ctg aag ggc att gac ttt aag gag gat gga aac att ctc ggc cac      432
Glu Leu Lys Gly Ile Asp Phe Lys Glu Asp Gly Asn Ile Leu Gly His
    125                 130                 135 aag ctg gaa tac aac tat aac tcc cac aat gtg tac atc atg gcc gac      480
Lys Leu Glu Tyr Asn Tyr Asn Ser His Asn Val Tyr Ile Met Ala Asp
140                 145                 150                 155 aag caa aag aat ggc atc aag gtc aac ttc aag atc aga cac aac att      528
Lys Gln Lys Asn Gly Ile Lys Val Asn Phe Lys Ile Arg His Asn Ile
                160                 165                 170 gag gat gga tcc gtg cag ctg gcc gac cat tat caa cag aac act cca      576
Glu Asp Gly Ser Val Gln Leu Ala Asp His Tyr Gln Gln Asn Thr Pro
```

```
                       175                 180                 185
atc ggc gac ggc cct gtg ctc ctc cca gac aac cat tac ctg tcc acc          624
Ile Gly Asp Gly Pro Val Leu Leu Pro Asp Asn His Tyr Leu Ser Thr
            190                 195                 200 cag tct gcc ctg tct aaa gat ccc aac gaa aag aga gac cac atg gtc          672
Gln Ser Ala Leu Ser Lys Asp Pro Asn Glu Lys Arg Asp His Met Val
    205                 210                 215 ctg ctg gag ttt gtg acc gct gct ggg atc aca cat ggc atg gac gag          720
Leu Leu Glu Phe Val Thr Ala Ala Gly Ile Thr His Gly Met Asp Glu
220                 225                 230                 235 ctg tac aag tga                                                          732
Leu Tyr Lys <210> SEQ ID NO 123
<211> LENGTH: 732
<212> TYPE: DNA
<213> ORGANISM: Artificial Sequence
<220> FEATURE:
<223> OTHER INFORMATION: Description of Artificial Sequence: Stop(TGA)
      5GFP
<220> FEATURE:
<221> NAME/KEY: CDS
<222> LOCATION: (1)..(732)

<400> SEQUENCE: 123 atg tga tga tga tga tga agc aag ggc gag gaa ctg ttc act ggc gtg          48
Met                     Ser Lys Gly Glu Glu Leu Phe Thr Gly Val
1                         5                  10 gtc cca att ctc gtg gaa ctg gat ggc gat gtg aat ggg cac aaa ttt          96
Val Pro Ile Leu Val Glu Leu Asp Gly Asp Val Asn Gly His Lys Phe
            15                  20                  25 tct gtc agc gga gag ggt gaa ggt gat gcc aca tac gga aag ctc acc          144
Ser Val Ser Gly Glu Gly Glu Gly Asp Ala Thr Tyr Gly Lys Leu Thr
        30                  35                  40 ctg aaa ttc atc tgc acc act gga aag ctc cct gtg cca tgg cca aca          192
Leu Lys Phe Ile Cys Thr Thr Gly Lys Leu Pro Val Pro Trp Pro Thr
    45                  50                  55 ctg gtc act acc ttc tct tat ggc gtg cag tgc ttt tcc aga tac cca          240
Leu Val Thr Thr Phe Ser Tyr Gly Val Gln Cys Phe Ser Arg Tyr Pro
60                  65                  70                  75 gac cat atg aag cag cat gac ttt ttc aag agc gcc atg ccc gag ggc          288
Asp His Met Lys Gln His Asp Phe Phe Lys Ser Ala Met Pro Glu Gly
            80                  85                  90 tat gtg cag gag aga acc atc ttt ttc aaa gat gac ggg aac tac aag          336
Tyr Val Gln Glu Arg Thr Ile Phe Phe Lys Asp Asp Gly Asn Tyr Lys
        95                 100                 105 acc cgc gct gaa gtc aag ttc gaa ggt gac acc ctg gtg aat aga atc          384
Thr Arg Ala Glu Val Lys Phe Glu Gly Asp Thr Leu Val Asn Arg Ile
    110                 115                 120 gag ctg aag ggc att gac ttt aag gag gat gga aac att ctc ggc cac          432
Glu Leu Lys Gly Ile Asp Phe Lys Glu Asp Gly Asn Ile Leu Gly His
125                 130                 135 aag ctg gaa tac aac tat aac tcc cac aat gtg tac atc atg gcc gac          480
Lys Leu Glu Tyr Asn Tyr Asn Ser His Asn Val Tyr Ile Met Ala Asp
140                 145                 150                 155 aag caa aag aat ggc atc aag gtc aac ttc aag atc aga cac aac att          528
Lys Gln Lys Asn Gly Ile Lys Val Asn Phe Lys Ile Arg His Asn Ile
            160                 165                 170 gag gat gga tcc gtg cag ctg gcc gac cat tat caa cag aac act cca          576
Glu Asp Gly Ser Val Gln Leu Ala Asp His Tyr Gln Gln Asn Thr Pro
        175                 180                 185
```

```
atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        190                 195                 200 cag tct gcc ctg tct aaa gat ccc aac gaa aag aga gac cac atg gtc      672
Gln Ser Ala Leu Ser Lys Asp Pro Asn Glu Lys Arg Asp His Met Val
205                 210                 215 ctg ctg gag ttt gtg acc gct gct ggg atc aca cat ggc atg gac gag      720
Leu Leu Glu Phe Val Thr Ala Ala Gly Ile Thr His Gly Met Asp Glu
220                 225                 230                 235 ctg tac aag tga                                                       732
Leu Tyr Lys <210> SEQ ID NO 124
<211> LENGTH: 717
<212> TYPE: DNA
<213> ORGANISM: Artificial Sequence
<220> FEATURE:
<223> OTHER INFORMATION: Description of Artificial Sequence: GFP
      humanized control
<220> FEATURE:
<221> NAME/KEY: CDS
<222> LOCATION: (1)..(717)

<400> SEQUENCE: 124 atg agc aag ggc gag gaa ctg ttc act ggc gtg gtc cca att ctc gtg       48
Met Ser Lys Gly Glu Glu Leu Phe Thr Gly Val Val Pro Ile Leu Val
1               5                   10                  15 gaa ctg gat ggc gat gtg aat ggg cac aaa ttt tct gtc agc gga gag       96
Glu Leu Asp Gly Asp Val Asn Gly His Lys Phe Ser Val Ser Gly Glu
                20                  25                  30 ggt gaa ggt gat gcc aca tac gga aag ctc acc ctg aaa ttc atc tgc      144
Gly Glu Gly Asp Ala Thr Tyr Gly Lys Leu Thr Leu Lys Phe Ile Cys
            35                  40                  45 acc act gga aag ctc cct gtg cca tgg cca aca ctg gtc act acc ttc      192
Thr Thr Gly Lys Leu Pro Val Pro Trp Pro Thr Leu Val Thr Thr Phe
        50                  55                  60 tct tat ggc gtg cag tgc ttt tcc aga tac cca gac cat atg aag cag      240
Ser Tyr Gly Val Gln Cys Phe Ser Arg Tyr Pro Asp His Met Lys Gln
65                  70                  75                  80 cat gac ttt ttc aag agc gcc atg ccc gag ggc tat gtg cag gag aga      288
His Asp Phe Phe Lys Ser Ala Met Pro Glu Gly Tyr Val Gln Glu Arg
                85                  90                  95 acc atc ttt ttc aaa gat gac ggg aac tac aag acc cgc gct gaa gtc      336
Thr Ile Phe Phe Lys Asp Asp Gly Asn Tyr Lys Thr Arg Ala Glu Val
            100                 105                 110 aag ttc gaa ggt gac acc ctg gtg aat aga atc gag ctg aag ggc att      384
Lys Phe Glu Gly Asp Thr Leu Val Asn Arg Ile Glu Leu Lys Gly Ile
        115                 120                 125 gac ttt aag gag gat gga aac att ctc ggc cac aag ctg gaa tac aac      432
Asp Phe Lys Glu Asp Gly Asn Ile Leu Gly His Lys Leu Glu Tyr Asn
130                 135                 140 tat aac tcc cac aat gtg tac atc atg gcc gac aag caa aag aat ggc      480
Tyr Asn Ser His Asn Val Tyr Ile Met Ala Asp Lys Gln Lys Asn Gly
145                 150                 155                 160 atc aag gtc aac ttc aag atc aga cac aac att gag gat gga tcc gtg      528
Ile Lys Val Asn Phe Lys Ile Arg His Asn Ile Glu Asp Gly Ser Val
                165                 170                 175 cag ctg gcc gac cat tat caa cag aac act cca atc ggc gac ggc cct      576
Gln Leu Ala Asp His Tyr Gln Gln Asn Thr Pro Ile Gly Asp Gly Pro
            180                 185                 190 gtg ctc ctc cca gac aac cat tac ctg tcc acc cag tct gcc ctg tct      624
Val Leu Leu Pro Asp Asn His Tyr Leu Ser Thr Gln Ser Ala Leu Ser
```

```
          195                 200                 205
aaa gat ccc aac gaa aag aga gac cac atg gtc ctg ctg gag ttt gtg      672
Lys Asp Pro Asn Glu Lys Arg Asp His Met Val Leu Leu Glu Phe Val
    210                 215                 220 acc gct gct ggg atc aca cat ggc atg gac gag ctg tac aag tga          717
Thr Ala Ala Gly Ile Thr His Gly Met Asp Glu Leu Tyr Lys
225                 230                 235

<210> SEQ ID NO 125
<211> LENGTH: 238
<212> TYPE: PRT
<213> ORGANISM: Artificial Sequence
<220> FEATURE:
<223> OTHER INFORMATION: Description of Artificial Sequence: GFP
      humanized control

<400> SEQUENCE: 125

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 126
<211> LENGTH: 54
<212> TYPE: DNA
<213> ORGANISM: Artificial Sequence
<220> FEATURE:
<223> OTHER INFORMATION: Description of Artificial Sequence: Ala(GCA)5
      primer

<400> SEQUENCE: 126
cggggtacca tggcagcagc agcagcaagc aagggcgagg aactgttcac tggc        54
```

<210> SEQ ID NO 127
<211> LENGTH: 54
<212> TYPE: DNA
<213> ORGANISM: Artificial Sequence
<220> FEATURE:
<223> OTHER INFORMATION: Description of Artificial Sequence: Ala(GCC)5
      primer

<400> SEQUENCE: 127
cggggtacca tggccgccgc cgccgccagc aagggcgagg aactgttcac tggc         54

<210> SEQ ID NO 128
<211> LENGTH: 54
<212> TYPE: DNA
<213> ORGANISM: Artificial Sequence
<220> FEATURE:
<223> OTHER INFORMATION: Description of Artificial Sequence: Ala(GCG)5
      primer

<400> SEQUENCE: 128
cggggtacca tggcggcggc ggcggcgagc aagggcgagg aactgttcac tggc         54

<210> SEQ ID NO 129
<211> LENGTH: 54
<212> TYPE: DNA
<213> ORGANISM: Artificial Sequence
<220> FEATURE:
<223> OTHER INFORMATION: Description of Artificial Sequence: Ala(GCT)5
      primer

<400> SEQUENCE: 129
cggggtacca tggctgctgc tgctgctagc aagggcgagg aactgttcac tggc         54

<210> SEQ ID NO 130
<211> LENGTH: 54
<212> TYPE: DNA
<213> ORGANISM: Artificial Sequence
<220> FEATURE:
<223> OTHER INFORMATION: Description of Artificial Sequence: Arg(AGA)5
      primer

<400> SEQUENCE: 130
cggggtacca tgagaagaag aagaagaagc aagggcgagg aactgttcac tggc         54

<210> SEQ ID NO 131
<211> LENGTH: 54
<212> TYPE: DNA
<213> ORGANISM: Artificial Sequence
<220> FEATURE:
<223> OTHER INFORMATION: Description of Artificial Sequence: Arg(AGG)5
      primer

<400> SEQUENCE: 131
cggggtacca tgaggaggag gaggaggagc aagggcgagg aactgttcac tggc         54

<210> SEQ ID NO 132
<211> LENGTH: 54
<212> TYPE: DNA
<213> ORGANISM: Artificial Sequence
<220> FEATURE:
<223> OTHER INFORMATION: Description of Artificial Sequence: Arg(CGA)5
      primer

<400> SEQUENCE: 132
cggggtacca tgcgacgacg acgacgaagc aagggcgagg aactgttcac tggc         54

<210> SEQ ID NO 133
<211> LENGTH: 54
<212> TYPE: DNA
<213> ORGANISM: Artificial Sequence
<220> FEATURE:
<223> OTHER INFORMATION: Description of Artificial Sequence: Arg(CGC)5
      primer

<400> SEQUENCE: 133
cggggtacca tgcgccgccg ccgccgcagc aagggcgagg aactgttcac tggc         54

<210> SEQ ID NO 134
<211> LENGTH: 54
<212> TYPE: DNA
<213> ORGANISM: Artificial Sequence
<220> FEATURE:
<223> OTHER INFORMATION: Description of Artificial Sequence: Arg(CGG)5
      primer

<400> SEQUENCE: 134
cggggtacca tgcggcggcg gcggcggagc aagggcgagg aactgttcac tggc         54

<210> SEQ ID NO 135
<211> LENGTH: 54
<212> TYPE: DNA
<213> ORGANISM: Artificial Sequence
<220> FEATURE:
<223> OTHER INFORMATION: Description of Artificial Sequence: arg(CGT)5
      primer

<400> SEQUENCE: 135
cggggtacca tgcgtcgtcg tcgtcgtagc aagggcgagg aactgttcac tggc         54

<210> SEQ ID NO 136
<211> LENGTH: 54
<212> TYPE: DNA
<213> ORGANISM: Artificial Sequence
<220> FEATURE:
<223> OTHER INFORMATION: Description of Artificial Sequence: Asn(AAC)5
      primer

<400> SEQUENCE: 136
cggggtacca tgaacaacaa caacaacagc aagggcgagg aactgttcac tggc         54

<210> SEQ ID NO 137
<211> LENGTH: 54
<212> TYPE: DNA
<213> ORGANISM: Artificial Sequence
<220> FEATURE:
<223> OTHER INFORMATION: Description of Artificial Sequence: Asn(AAT)5
      primer

<400> SEQUENCE: 137
cggggtacca tgaataataa taataatagc aagggcgagg aactgttcac tggc         54

<210> SEQ ID NO 138
<211> LENGTH: 54
<212> TYPE: DNA
<213> ORGANISM: Artificial Sequence
<220> FEATURE:
<223> OTHER INFORMATION: Description of Artificial Sequence: Asp(GAC)5
      primer

<400> SEQUENCE: 138
cggggtacca tggacgacga cgacgacagc aagggcgagg aactgttcac tggc         54

<210> SEQ ID NO 139
<211> LENGTH: 54

```
<212> TYPE: DNA
<213> ORGANISM: Artificial Sequence
<220> FEATURE:
<223> OTHER INFORMATION: Description of Artificial Sequence: Asp(GAT)5
      primer

<400> SEQUENCE: 139
cggggtacca tggatgatga tgatgatagc aagggcgagg aactgttcac tggc          54

<210> SEQ ID NO 140
<211> LENGTH: 54
<212> TYPE: DNA
<213> ORGANISM: Artificial Sequence
<220> FEATURE:
<223> OTHER INFORMATION: Description of Artificial Sequence: Cys(TGC)5
      primer

<400> SEQUENCE: 140
cggggtacca tgtgctgctg ctgctgcagc aagggcgagg aactgttcac tggc          54

<210> SEQ ID NO 141
<211> LENGTH: 54
<212> TYPE: DNA
<213> ORGANISM: Artificial Sequence
<220> FEATURE:
<223> OTHER INFORMATION: Description of Artificial Sequence: Cys(TGT)5
      primer

<400> SEQUENCE: 141
cggggtacca tgtgttgttg ttgttgtagc aagggcgagg aactgttcac tggc          54

<210> SEQ ID NO 142
<211> LENGTH: 54
<212> TYPE: DNA
<213> ORGANISM: Artificial Sequence
<220> FEATURE:
<223> OTHER INFORMATION: Description of Artificial Sequence: Gln(CAA)5
      primer

<400> SEQUENCE: 142
cggggtacca tgcaacaaca acaacaaagc aagggcgagg aactgttcac tggc          54

<210> SEQ ID NO 143
<211> LENGTH: 54
<212> TYPE: DNA
<213> ORGANISM: Artificial Sequence
<220> FEATURE:
<223> OTHER INFORMATION: Description of Artificial Sequence: Gln(CAG)5
      primer

<400> SEQUENCE: 143
cggggtacca tgcagcagca gcagcagagc aagggcgagg aactgttcac tggc          54

<210> SEQ ID NO 144
<211> LENGTH: 54
<212> TYPE: DNA
<213> ORGANISM: Artificial Sequence
<220> FEATURE:
<223> OTHER INFORMATION: Description of Artificial Sequence: Glu(GAA)5
      primer

<400> SEQUENCE: 144
cggggtacca tggaagaaga agaagaaagc aagggcgagg aactgttcac tggc          54

<210> SEQ ID NO 145
<211> LENGTH: 54
<212> TYPE: DNA
```

```
<213> ORGANISM: Artificial Sequence
<220> FEATURE:
<223> OTHER INFORMATION: Description of Artificial Sequence: Glu(GAG)5
      primer

<400> SEQUENCE: 145
cggggtacca tggaggagga ggaggagagc aagggcgagg aactgttcac tggc          54

<210> SEQ ID NO 146
<211> LENGTH: 54
<212> TYPE: DNA
<213> ORGANISM: Artificial Sequence
<220> FEATURE:
<223> OTHER INFORMATION: Description of Artificial Sequence: Gly(GGA)5
      primer

<400> SEQUENCE: 146
cggggtacca tgggaggagg aggaggaagc aagggcgagg aactgttcac tggc          54

<210> SEQ ID NO 147
<211> LENGTH: 54
<212> TYPE: DNA
<213> ORGANISM: Artificial Sequence
<220> FEATURE:
<223> OTHER INFORMATION: Description of Artificial Sequence: Gly(GGC)5
      primer

<400> SEQUENCE: 147
cggggtacca tgggcggcgg cggcggcagc aagggcgagg aactgttcac tggc          54

<210> SEQ ID NO 148
<211> LENGTH: 54
<212> TYPE: DNA
<213> ORGANISM: Artificial Sequence
<220> FEATURE:
<223> OTHER INFORMATION: Description of Artificial Sequence: Gly(GGG)5
      primer

<400> SEQUENCE: 148
cggggtacca tgggggggggg ggggggagc aagggcgagg aactgttcac tggc          54

<210> SEQ ID NO 149
<211> LENGTH: 54
<212> TYPE: DNA
<213> ORGANISM: Artificial Sequence
<220> FEATURE:
<223> OTHER INFORMATION: Description of Artificial Sequence: Gly(GGT)5
      primer

<400> SEQUENCE: 149
cggggtacca tgggtggtgg tggtggtagc aagggcgagg aactgttcac tggc          54

<210> SEQ ID NO 150
<211> LENGTH: 54
<212> TYPE: DNA
<213> ORGANISM: Artificial Sequence
<220> FEATURE:
<223> OTHER INFORMATION: Description of Artificial Sequence: His(CAC)5
      primer

<400> SEQUENCE: 150
cggggtacca tgcaccacca ccaccacagc aagggcgagg aactgttcac tggc          54

<210> SEQ ID NO 151
<211> LENGTH: 54
<212> TYPE: DNA
<213> ORGANISM: Artificial Sequence
```

```
<220> FEATURE:
<223> OTHER INFORMATION: Description of Artificial Sequence: His(CAT)5
      primer

<400> SEQUENCE: 151
cggggtacca tgcatcatca tcatcatagc aagggcgagg aactgttcac tggc         54

<210> SEQ ID NO 152
<211> LENGTH: 54
<212> TYPE: DNA
<213> ORGANISM: Artificial Sequence
<220> FEATURE:
<223> OTHER INFORMATION: Description of Artificial Sequence: Ile(ATA)5
      primer

<400> SEQUENCE: 152
cggggtacca tgataataat aataataagc aagggcgagg aactgttcac tggc         54

<210> SEQ ID NO 153
<211> LENGTH: 54
<212> TYPE: DNA
<213> ORGANISM: Artificial Sequence
<220> FEATURE:
<223> OTHER INFORMATION: Description of Artificial Sequence: Ile(ATC)5
      primer

<400> SEQUENCE: 153
cggggtacca tgatcatcat catcatcagc aagggcgagg aactgttcac tggc         54

<210> SEQ ID NO 154
<211> LENGTH: 54
<212> TYPE: DNA
<213> ORGANISM: Artificial Sequence
<220> FEATURE:
<223> OTHER INFORMATION: Description of Artificial Sequence: Ile(ATT)5
      primer

<400> SEQUENCE: 154
cggggtacca tgattattat tattattagc aagggcgagg aactgttcac tggc         54

<210> SEQ ID NO 155
<211> LENGTH: 54
<212> TYPE: DNA
<213> ORGANISM: Artificial Sequence
<220> FEATURE:
<223> OTHER INFORMATION: Description of Artificial Sequence: Leu(CTA)5
      primer

<400> SEQUENCE: 155
cggggtacca tgctactact actactaagc aagggcgagg aactgttcac tggc         54

<210> SEQ ID NO 156
<211> LENGTH: 54
<212> TYPE: DNA
<213> ORGANISM: Artificial Sequence
<220> FEATURE:
<223> OTHER INFORMATION: Description of Artificial Sequence: Leu(CTC)5
      primer

<400> SEQUENCE: 156
cggggtacca tgctcctcct cctcctcagc aagggcgagg aactgttcac tggc         54

<210> SEQ ID NO 157
<211> LENGTH: 54
<212> TYPE: DNA
<213> ORGANISM: Artificial Sequence
<220> FEATURE:
```

<223> OTHER INFORMATION: Description of Artificial Sequence: Leu(CTG)5
      primer

<400> SEQUENCE: 157
cggggtacca tgctgctgct gctgctgagc aagggcgagg aactgttcac tggc          54

<210> SEQ ID NO 158
<211> LENGTH: 54
<212> TYPE: DNA
<213> ORGANISM: Artificial Sequence
<220> FEATURE:
<223> OTHER INFORMATION: Description of Artificial Sequence: Leu(CTT)5
      primer

<400> SEQUENCE: 158
cggggtacca tgcttcttct tcttcttagc aagggcgagg aactgttcac tggc          54

<210> SEQ ID NO 159
<211> LENGTH: 54
<212> TYPE: DNA
<213> ORGANISM: Artificial Sequence
<220> FEATURE:
<223> OTHER INFORMATION: Description of Artificial Sequence: Leu(TTA)5
      primer

<400> SEQUENCE: 159
cggggtacca tgttattatt attattaagc aagggcgagg aactgttcac tggc          54

<210> SEQ ID NO 160
<211> LENGTH: 54
<212> TYPE: DNA
<213> ORGANISM: Artificial Sequence
<220> FEATURE:
<223> OTHER INFORMATION: Description of Artificial Sequence: Leu(TTG)5
      primer

<400> SEQUENCE: 160
cggggtacca tgttgttgtt gttgttgagc aagggcgagg aactgttcac tggc          54

<210> SEQ ID NO 161
<211> LENGTH: 54
<212> TYPE: DNA
<213> ORGANISM: Artificial Sequence
<220> FEATURE:
<223> OTHER INFORMATION: Description of Artificial Sequence: Lys(AAA)5
      primer

<400> SEQUENCE: 161
cggggtacca tgaaaaaaaa aaaaaaaagc aagggcgagg aactgttcac tggc          54

<210> SEQ ID NO 162
<211> LENGTH: 54
<212> TYPE: DNA
<213> ORGANISM: Artificial Sequence
<220> FEATURE:
<223> OTHER INFORMATION: Description of Artificial Sequence: Lys(AAG)5
      primer

<400> SEQUENCE: 162
cggggtacca tgaagaagaa gaagaagagc aagggcgagg aactgttcac tggc          54

<210> SEQ ID NO 163
<211> LENGTH: 54
<212> TYPE: DNA
<213> ORGANISM: Artificial Sequence
<220> FEATURE:
<223> OTHER INFORMATION: Description of Artificial Sequence: Phe(CTT)5

```
              primer

<400> SEQUENCE: 163
cggggtacca tgcttcttct tcttcttagc aagggcgagg aactgttcac tggc      54

<210> SEQ ID NO 164
<211> LENGTH: 54
<212> TYPE: DNA
<213> ORGANISM: Artificial Sequence
<220> FEATURE:
<223> OTHER INFORMATION: Description of Artificial Sequence: Phe(TTC)5
      primer

<400> SEQUENCE: 164
cggggtacca tgttcttctt cttcttcagc aagggcgagg aactgttcac tggc      54

<210> SEQ ID NO 165
<211> LENGTH: 54
<212> TYPE: DNA
<213> ORGANISM: Artificial Sequence
<220> FEATURE:
<223> OTHER INFORMATION: Description of Artificial Sequence: Pro(CCC)5
      primer

<400> SEQUENCE: 165
cggggtacca tgcccccccc ccccccagc aagggcgagg aactgttcac tggc       54

<210> SEQ ID NO 166
<211> LENGTH: 54
<212> TYPE: DNA
<213> ORGANISM: Artificial Sequence
<220> FEATURE:
<223> OTHER INFORMATION: Description of Artificial Sequence: Pro(CCG)5
      primer

<400> SEQUENCE: 166
cggggtacca tgccgccgcc gccgccgagc aagggcgagg aactgttcac tggc      54

<210> SEQ ID NO 167
<211> LENGTH: 54
<212> TYPE: DNA
<213> ORGANISM: Artificial Sequence
<220> FEATURE:
<223> OTHER INFORMATION: Description of Artificial Sequence: Pro(CCT)5
      primer

<400> SEQUENCE: 167
cggggtacca tgcctcctcc tcctcctagc aagggcgagg aactgttcac tggc      54

<210> SEQ ID NO 168
<211> LENGTH: 54
<212> TYPE: DNA
<213> ORGANISM: Artificial Sequence
<220> FEATURE:
<223> OTHER INFORMATION: Description of Artificial Sequence: Pro(CGA)5
      primer

<400> SEQUENCE: 168
cggggtacca tgcgacgacg acgacgaagc aagggcgagg aactgttcac tggc      54

<210> SEQ ID NO 169
<211> LENGTH: 54
<212> TYPE: DNA
<213> ORGANISM: Artificial Sequence
<220> FEATURE:
<223> OTHER INFORMATION: Description of Artificial Sequence: Ser(AGC)5
      primer
```

```
<400> SEQUENCE: 169
cggggtacca tgagcagcag cagcagcagc aagggcgagg aactgttcac tggc        54

<210> SEQ ID NO 170
<211> LENGTH: 54
<212> TYPE: DNA
<213> ORGANISM: Artificial Sequence
<220> FEATURE:
<223> OTHER INFORMATION: Description of Artificial Sequence: Ser(AGT)5
      primer

<400> SEQUENCE: 170
cggggtacca tgagtagtag tagtagtagc aagggcgagg aactgttcac tggc        54

<210> SEQ ID NO 171
<211> LENGTH: 54
<212> TYPE: DNA
<213> ORGANISM: Artificial Sequence
<220> FEATURE:
<223> OTHER INFORMATION: Description of Artificial Sequence: Ser(TCA)5
      primer

<400> SEQUENCE: 171
cggggtacca tgtcatcatc atcatcaagc aagggcgagg aactgttcac tggc        54

<210> SEQ ID NO 172
<211> LENGTH: 54
<212> TYPE: DNA
<213> ORGANISM: Artificial Sequence
<220> FEATURE:
<223> OTHER INFORMATION: Description of Artificial Sequence: Ser(TCC)5
      primer

<400> SEQUENCE: 172
cggggtacca tgtcctcctc ctcctccagc aagggcgagg aactgttcac tggc        54

<210> SEQ ID NO 173
<211> LENGTH: 54
<212> TYPE: DNA
<213> ORGANISM: Artificial Sequence
<220> FEATURE:
<223> OTHER INFORMATION: Description of Artificial Sequence: Ser(TCG)5
      primer

<400> SEQUENCE: 173
cggggtacca tgtcgtcgtc gtcgtcgagc aagggcgagg aactgttcac tggc        54

<210> SEQ ID NO 174
<211> LENGTH: 54
<212> TYPE: DNA
<213> ORGANISM: Artificial Sequence
<220> FEATURE:
<223> OTHER INFORMATION: Description of Artificial Sequence: Ser(TCT)5
      primer

<400> SEQUENCE: 174
cggggtacca tgtcttcttc ttcttctagc aagggcgagg aactgttcac tggc        54

<210> SEQ ID NO 175
<211> LENGTH: 54
<212> TYPE: DNA
<213> ORGANISM: Artificial Sequence
<220> FEATURE:
<223> OTHER INFORMATION: Description of Artificial Sequence: Thr(ACA)5
      primer
```

```
<400> SEQUENCE: 175
cggggtacca tgacaacaac aacaacaagc aagggcgagg aactgttcac tggc          54

<210> SEQ ID NO 176
<211> LENGTH: 54
<212> TYPE: DNA
<213> ORGANISM: Artificial Sequence
<220> FEATURE:
<223> OTHER INFORMATION: Description of Artificial Sequence: Thr(ACC)5
      primer

<400> SEQUENCE: 176
cggggtacca tgaccaccac caccaccagc aagggcgagg aactgttcac tggc          54

<210> SEQ ID NO 177
<211> LENGTH: 54
<212> TYPE: DNA
<213> ORGANISM: Artificial Sequence
<220> FEATURE:
<223> OTHER INFORMATION: Description of Artificial Sequence: Thr(ACG)5
      primer

<400> SEQUENCE: 177
cggggtacca tgacgacgac gacgacgagc aagggcgagg aactgttcac tggc          54

<210> SEQ ID NO 178
<211> LENGTH: 54
<212> TYPE: DNA
<213> ORGANISM: Artificial Sequence
<220> FEATURE:
<223> OTHER INFORMATION: Description of Artificial Sequence: Thr(ACT)5
      primer

<400> SEQUENCE: 178
cggggtacca tgactactac tactactagc aagggcgagg aactgttcac tggc          54

<210> SEQ ID NO 179
<211> LENGTH: 54
<212> TYPE: DNA
<213> ORGANISM: Artificial Sequence
<220> FEATURE:
<223> OTHER INFORMATION: Description of Artificial Sequence: Trp(TGG)5
      primer

<400> SEQUENCE: 179
cggggtacca tgtggtggtg gtggtggagc aagggcgagg aactgttcac tggc          54

<210> SEQ ID NO 180
<211> LENGTH: 54
<212> TYPE: DNA
<213> ORGANISM: Artificial Sequence
<220> FEATURE:
<223> OTHER INFORMATION: Description of Artificial Sequence: Tyr(TAT)5
      primer

<400> SEQUENCE: 180
cggggtacca tgtattatta ttattatagc aagggcgagg aactgttcac tggc          54

<210> SEQ ID NO 181
<211> LENGTH: 54
<212> TYPE: DNA
<213> ORGANISM: Artificial Sequence
<220> FEATURE:
<223> OTHER INFORMATION: Description of Artificial Sequence: Val(GTA)5
      primer

<400> SEQUENCE: 181
```

```
cggggtacca tggtagtagt agtagtaagc aagggcgagg aactgttcac tggc        54
```

<210> SEQ ID NO 182
<211> LENGTH: 54
<212> TYPE: DNA
<213> ORGANISM: Artificial Sequence
<220> FEATURE:
<223> OTHER INFORMATION: Description of Artificial Sequence: Val(GTC)5
      primer

<400> SEQUENCE: 182

```
cggggtacca tggtcgtcgt cgtcgtcagc aagggcgagg aactgttcac tggc        54
```

<210> SEQ ID NO 183
<211> LENGTH: 54
<212> TYPE: DNA
<213> ORGANISM: Artificial Sequence
<220> FEATURE:
<223> OTHER INFORMATION: Description of Artificial Sequence: Val(GTG)5
      primer

<400> SEQUENCE: 183

```
cggggtacca tggtggtggt ggtggtgagc aagggcgagg aactgttcac tggc        54
```

<210> SEQ ID NO 184
<211> LENGTH: 54
<212> TYPE: DNA
<213> ORGANISM: Artificial Sequence
<220> FEATURE:
<223> OTHER INFORMATION: Description of Artificial Sequence: Val(GTT)5
      primer

<400> SEQUENCE: 184

```
cggggtacca tggttgttgt tgttgttagc aagggcgagg aactgttcac tggc        54
```

<210> SEQ ID NO 185
<211> LENGTH: 33
<212> TYPE: DNA
<213> ORGANISM: Artificial Sequence
<220> FEATURE:
<223> OTHER INFORMATION: Description of Artificial Sequence: 3'
      oligonucleotide common primer

<400> SEQUENCE: 185

```
ccggaattct cacttgtaca ggtggtccat gcc                              33
```